United States Patent
Gillanders et al.

(10) Patent No.: US 12,319,720 B2
(45) Date of Patent: Jun. 3, 2025

(54) NEOANTIGEN VACCINES FOR TRIPLE NEGATIVE BREAST CANCER

(71) Applicant: Washington University, St. Louis, MO (US)

(72) Inventors: William Gillanders, St. Louis, MO (US); Ted Hansen, North Potomac, MD (US); S. Peter Goedegebuure, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/823,937

(22) Filed: Aug. 31, 2022

(65) Prior Publication Data
US 2023/0145121 A1 May 11, 2023

Related U.S. Application Data

(60) Provisional application No. 63/239,312, filed on Aug. 31, 2021.

(51) Int. Cl.
| | |
|---|---|
| *C07K 14/47* | (2006.01) |
| *A61K 39/00* | (2006.01) |
| *A61P 35/00* | (2006.01) |
| *C12N 15/85* | (2006.01) |

(52) U.S. Cl.
CPC .......... *C07K 14/4748* (2013.01); *A61P 35/00* (2018.01); *C07K 14/47* (2013.01); *C12N 15/85* (2013.01); *A61K 39/00* (2013.01); *C07K 2319/00* (2013.01); *C12N 2800/107* (2013.01)

(58) Field of Classification Search
None
See application file for complete search history.

(56) References Cited

U.S. PATENT DOCUMENTS

| | | | |
|---|---|---|---|
| 2009/0221682 A1* | 9/2009 | Maithal | C07K 14/57563 536/23.5 |
| 2017/0253633 A1* | 9/2017 | Mahr | C07K 16/18 |
| 2019/0381160 A1 | 12/2019 | Petit et al. | |

FOREIGN PATENT DOCUMENTS

| | | | | |
|---|---|---|---|---|
| WO | WO 2011/110953 | * | 9/2011 | .......... C07K 14/435 |
| WO | 2018102585 A1 | | 6/2018 | |
| WO | 2021046466 A1 | | 3/2021 | |

OTHER PUBLICATIONS

Bhattacharya et al., Plos One 12(3): e0171355. https://doi.org/10.1371/journal.pone.0171355; 22 pages total (Year: 2017).*
Fenton et al., Medicinal Chemistry Research (2020) 29:1133-1146 (Year: 2020).*
Moody et al., Curr Opin Endocrinol Diabetes Obes 2016, 23:38-47 (Year: 2016).*
Lehman et al., PLoS ONE (2016), 11(6): e0157368 doi: 10.1371/journal.pone.0157368 (Year: 2016).*
Alexander et al. (2002) A decaepitope polypeptide primes for multiple CD8+ IFN-gamma and Th lymphocyte responses: evaluation of multiepitope polypeptides as a mode for vaccine delivery. J Immunol. vol. 168, No. 12, pp. 6189-6198.
Aslakson et al. (1992) Selective events in the metastatic process defined by analysis of the sequential dissemination of subpopulations of a mouse mammary tumor. Cancer Res. vol. 52, No. 6, pp. 1399-1405.
Bijker et al. (2007) CD8+ CTL priming by exact peptide epitopes in incomplete Freund's adjuvant induces a vanishing CTL response, whereas long peptides induce sustained CTL reactivity. J Immunol. vol. 179, No. 8, pp. 5033-5040.
Bins et al. (2005) A rapid and potent DNA vaccination strategy defined by in vivo monitoring of antigen expression. Nat Med. vol. 11, No. 8, pp. 899-904.
Carreno et al. (2015) Cancer immunotherapy. A dendritic cell vaccine increases the breadth and diversity of melanoma neoantigen-specific T cells. Science. vol. 348, No. 6236, pp. 803-808.
Dantuma et al. (2000) Short-lived green fluorescent proteins for quantifying ubiquitin/proteasome-dependent proteolysis in living cells. Nat Biotechnol. vol. 18, No. 5, pp. 538-543.
Davis et al. (1993) DNA-based immunization induces continuous secretion of hepatitis B surface antigen and high levels of circulating antibody. Hum Mol Genet. vol. 2, No. 11, pp. 1847-1851.
Duperret et al. (2019) A synthetic DNA, multi-neoantigen vaccine drives predominately MHC class I CD8(+) T-cell responses, impacting tumor challenge. Cancer Immunol Res. vol. 7, No. 2, pp. 174-182.
Ewens et al. (2005) Distant metastasis from subcutaneously grown E0771 medullary breast adenocarcinoma. Anticancer Res. vol. 25, No. 6B, pp. 3905-3915.
Ferraro et al. (2011) Clinical applications of DNA vaccines: current progress. Clin Infect Dis. vol. 53, No. 3, pp. 296-302.
Fynan et al. (1993) DNA vaccines: protective immunizations by parenteral, mucosal, and gene-gun inoculations. Proc Natl Acad Sci U S A. vol. 90, No. 24, pp. 11478-11482.
Gubin et al. (2014) Checkpoint blockade cancer immunotherapy targets tumour-specific mutant antigens. Nature. vol. 515, No. 7528, pp. 577-581.
Hilf et al. (2019) Actively personalized vaccination trial for newly diagnosed glioblastoma. Nature. vol. 565, No. 7738, pp. 240-245.
Hundal et al. (2016) pVAC-Seq: a genome-guided in silico approach to identifying tumor neoantigens. Genome Med. vol. 8, No. 11, 11 pages.
Hundal et al. (2020) pVACtools: a computational toolkit to identify and visualize cancer neoantigens. Cancer Immunol Res. vol. 8, No. 3, pp. 409-420.

(Continued)

Primary Examiner — Christina M Borgeest

(57) ABSTRACT

The present disclosure is directed to compositions and methods of treating Triple Negative Breast Cancer (TNBC) in a human subject. A method of treating TNBC in a human subject includes administering a therapeutically effective amount of a neoantigen vaccine composition comprising a fusion protein comprising at least one TNBC-associated neoantigen epitope joined to a mutant ubiquitin protein, or a nucleic acid molecule encoding such a protein.

4 Claims, 53 Drawing Sheets
Specification includes a Sequence Listing.

(56) References Cited

OTHER PUBLICATIONS

Johnson et al. (1992) Ubiquitin as a degradation signal. EMBO J. vol. 11, No. 2, pp. 497-505.
Johnson et al. (1995) A proteolytic pathway that recognizes ubiquitin as a degradation signal. J Biol Chem. vol. 270, No. 29, pp. 17442-17456.
Jurtz et al. (2017) NetMHCpan-4.0: improved peptide-MHC class I interaction predictions integrating eluted ligand and peptide binding affinity data. J Immunol. vol. 199, No. 9, pp. 3360-3368.
Keskin et al. (2019) Neoantigen vaccine generates intratumoral T cell responses in phase Ib glioblastoma trial. Nature. vol. 565, No. 7738, pp. 234-239.
Kim et al. (2008) Ubiquitin signals autophagic degradation of cytosolic proteins and peroxisomes. Proc Natl Acad Sci U S A. vol. 105, No. 52, pp. 20567-20574.
Kim et al. (2010) Single-chain HLA-A2 Mhc trimers that incorporate an immundominant peptide elicit protective T cell immunity against lethal West Nile virus infection. J Immunol. vol. 184, No. 8, pp. 4423-4430.
Kreiter et al. (2012) Targeting the tumor mutanome for personalized vaccination therapy. Oncoimmunology. vol. 1, No. 5, pp. 768-769.
Kutzler et al. (2008) DNA vaccines: ready for prime time? Nat Rev Genet. vol. 9, No. 10, pp. 776-788.
Lelekakis et al. (1999) A novel orthotopic model of breast cancer metastasis to bone. Clin Exp Metastasis. vol. 17, No. 2, pp. 163-170.
Levy et al. (2007) A melanoma multiepitope polypeptide induces specific CD8+ T-cell response. Cell Immunol. vol. 250, No. 1-2, pp. 24-30.
Li et al. (2010) Engineering superior DNA vaccines: MHC class I single chain trimers bypass antigen processing and enhance the immune response to low affinity antigens. Vaccine. vol. 28, No. 8, pp. 1911-1918.
Li et al. (2011) Cancer genome sequencing and its implications for personalized cancer vaccines. Cancers (Basel). vol. 3, No. 4, pp. 4191-4211.
Li et al. (2017) Preclinical and clinical development of neoantigen vaccines. Ann Oncol. vol. 28, suppl_12, pp. xii11- xii17.
Li et al. (Apr. 2021) Optimized polyepitope neoantigen DNA vaccines elicit neoantigen—specific immune responses in preclinical models and in clinical translation. Genome Medicine. vol. 13, 56, 13 pages.
Lybarger et al. (2003) Virus subversion of the MHC class I peptide-loading complex. Immunity. vol. 18, No. 1, pp. 121-130.
Matsushita et al. (2012) Cancer exome analysis reveals a T-cell-dependent mechanism of cancer immunoediting. Nature. vol. 482, No. 7385, pp. 400-404.
Neisig et al. (1995) Major differences in transporter associated with antigen presentation (TAP)-dependent translocation of MHC class I-presentable peptides and the effect of flanking sequences. J Immunol. vol. 154, No. 3, pp. 1273-1279.
Ott et al. (2017) An immunogenic personal neoantigen vaccine for patients with melanoma. Nature. vol. 547, No. 7662, pp. 217-221.
Pascolo et al. (1997) HLA-A2.1-restricted education and cytolytic activity of CD8(+) T lymphocytes from beta2 microglobulin (beta2m) HLA-A2.1 monochain transgenic H-2Db beta2m double knockout mice. J Exp Med. vol. 185, No. 12, pp. 2043-2051.
Ribas et al. (2018) Cancer immunotherapy using checkpoint blockade. Science. vol. 359, No. 6382, pp. 1350-1355.
Rizvi et al. (2015) Cancer immunology. Mutational landscape determines sensitivity to PD-1 blockade in non-small cell lung cancer. Science. vol. 348, No. 6230, pp. 124-128.
Rock et al. (1999) Degradation of cell proteins and the generation of MHC class I-presented peptides. Annu Rev Immunol. vol. 17, No. 1, pp. 739-779.
Sahin et al. (2017) Personalized RNA mutanome vaccines mobilize poly-specific therapeutic immunity against cancer. Nature. vol. 547, No. 7662, pp. 222-226.
Snell et al. (1948) Tumor immunity in mice, induced with lyophilized tissue, as influenced by tumor strain, host strain, source of tissue, and dosage. Cancer Res. vol. 8, No. 9, pp. 429-437.
Tang et al. (1992) Genetic immunization is a simple method for eliciting an immune response. Nature. vol. 356, No. 6365, pp. 152-154.
Topalian et al. (2015) Immune checkpoint blockade: a common denominator approach to cancer therapy. Cancer Cell. vol. 27, No. 4, pp. 450-461.
Ulmer et al. (1993) Heterologous protection against influenza by injection of DNA encoding a viral protein. Science. vol. 259, No. 5102, pp. 1745-1749.
Varshavsky (1997) The N-end rule pathway of protein degradation. Genes Cells. vol. 2, No. 1, pp. 13-28.
Velders et al. (2001) Defined flanking spacers and enhanced proteolysis is essential for eradication of established tumors by an epitope string DNA vaccine. J Immunol. vol. 166, No. 9, pp. 5366-5373.
Wang et al. (2013) Decoupling the role of ubiquitination for the dislocation versus degradation of major histocompatibility complex (MHC) class I proteins during endoplasmic reticulum-associated degradation(ERAD). J Biol Chem. vol. 288, No. 32, pp. 23295-23306.
Washington University in St. Louis (2020) BioProject PRJNA685845. Sequence Read Archive (SRA). https://www.ncbi.nlm.nih.gov/bioproject/?term=PRJNA685845. Accessed Jul. 13, 2023. 1 page.
Wei et al. (2018) Fundamental mechanisms of immune checkpoint blockade therapy. Cancer Discov. vol. 8, No. 9, pp. 1069-1086.
Zhang et al. (2017) Breast cancer neoantigens can induce CD8+ T-cell responses and antitumor immunity. Cancer Immunol Res. vol. 5, No. 7, pp. 516-523.

* cited by examiner

| Patient ID | Age | Race | Stage | Treatment Neoadjuvant | Treatment Adjuvant | No. of epitopes in vaccine | Neoantigen Immune Response Baseline | Neoantigen Immune Response After Vaccine | Recurrence after vaccine (Y/N) |
|---|---|---|---|---|---|---|---|---|---|
| BRC45 | 68 | AA | CT1N1M0 | TC | RT | 7 | 0 | 2 | N |
| BRC78 | 33 | White | CT1N1M0 | ACT | RT/GC | 7 | 0 | 2 | N |
| BRC10 | 61 | AA | CT2N0M0 | TC | RT | 10 | 1 | 2 | N |
| BRC18 | 36 | White | CT2-3N0M0 | ACT | Metformin | 10 | 2 | 3 | N |
| BRC93 | 54 | White | CT2N1M0 | ACTP | RT/Capecitabine | 10 | 2 | 5 | N |
| BRC73 | 63 | White | CT2N0M0 | ACTP | RT | 8 | 3 | 0 | Y |
| BRC16 | 60 | AA | CT3N0M0 | TC | Capecitabine | 7 | 0 | 0 | N |
| BRC80 | 69 | White | CT2N1M0 | TC | RT/Capecitabine | 4 | 0 | 1 | Y |
| BRC77 | 43 | White | T3N1M0 | TC | RT | 6 | 0 | 1 | N |
| BRC56 | 38 | White | T3N0M0 | ACTP | RT | 10 | 1 | 3 | N |
| BRC19 | 53 | AA | CT2N0M0 | TC | RT | 11 | 1 | 1 | N |
| BRC64 | 52 | AA | CT3N1M0 | ACT | RT | 10 | 0 | 4 | N |
| BRC65 | 51 | White | CT2N1M0 | ACT | RT/Capecitabine | 4 | 2 | 4 | N |
| BRC58 | 53 | White | CT2N1M0 | TP | RT | 20 | 1 | 4 | N |
| BRC98 | 49 | White | CT2N3M0 | TP | RT | 16 | 0 | 1 | N |
| BRC46 | 68 | AA | CT2N1M0 | TP | RT/EC | 20 | 1 | 2 | N |
| BRC08 | 56 | White | CT2N0M0 | TP | RT | 14 | 2 | 2 | N |
| BRC06 | 50 | White | CT2N0M0 | TC | AC | 20 | 3 | 3 | N |

FIG. 2C

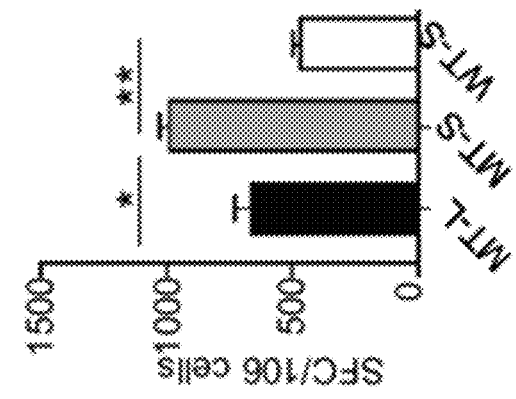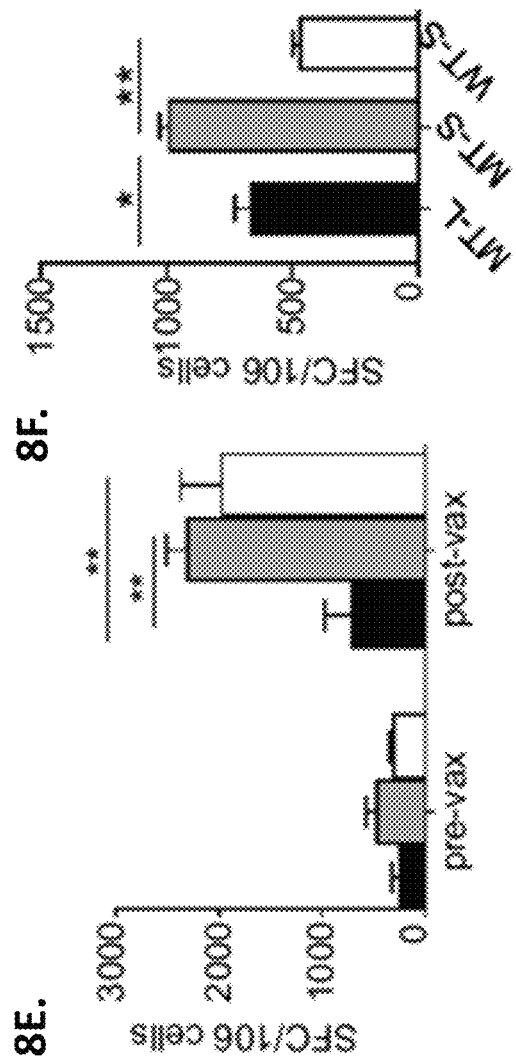
FIGS. 8D-8F

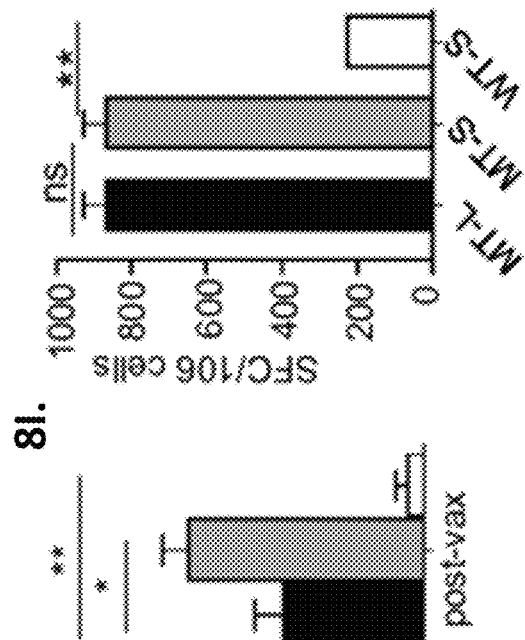
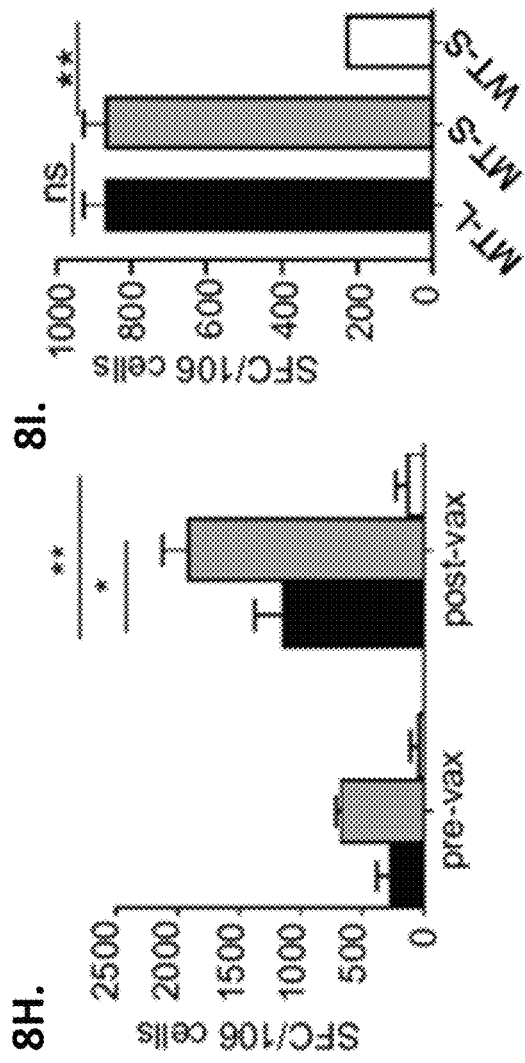
FIGS. 8G-8I

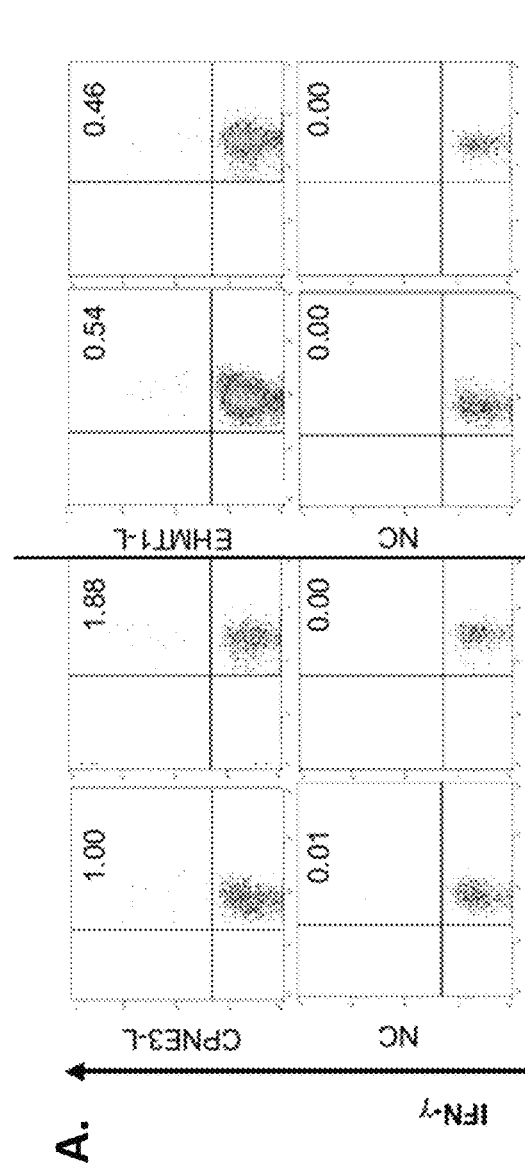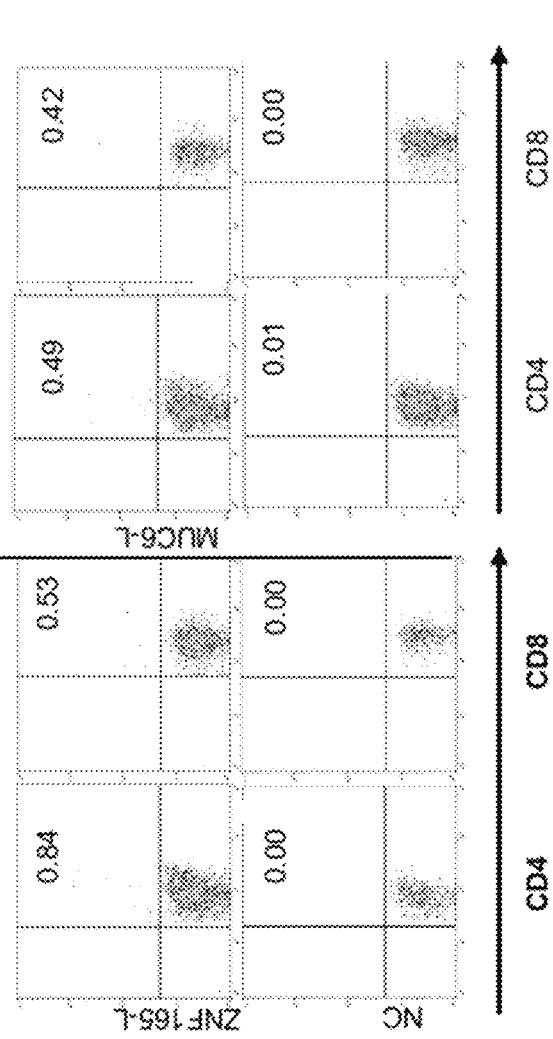
FIGS. 10A-10D

NEOANTIGEN VACCINES FOR TRIPLE NEGATIVE BREAST CANCER

CROSS-REFERENCE TO RELATED APPLICATION

This application claims the benefit of U.S. Provisional Application No. 63/239,312 filed Aug. 31, 2021.

GOVERNMENT SUPPORT CLAUSE

This invention was made with government support under CA009621, CA196510, CA091842, and CA240983 awarded by the National Institutes of Health. The government has certain rights in the invention.

SEQUENCE LISTING

The contents of the electronic sequence listing (42194-12_updated_sequence_listing.xml; Size: 32,000 bytes; Date of Creation: Jan. 30, 2023) is herein incorporated by reference in its entirety.

FIELD OF THE DISCLOSURE

The field of the disclosure relates generally to neoantigen vaccines and their use in cancer treatment. More specifically, the disclosure relates to identification of Triple Negative Breast Cancer (TNBC) neoantigens, design and optimization of neoantigen vaccine candidates, and synthesis of neoantigen vaccines for improved treatment of TNBC.

BACKGROUND OF THE DISCLOSURE

Cancer neoantigens are mutant proteins/amino acid sequences expressed in tumors that can be recognized by the immune system. Cancer sequencing and related bioinformatics technologies have revolutionized the ability to rapidly identify cancer neoantigens. Disclosed herein is one of the first preclinical studies to apply an immunogenomics approach to neoantigen identification. It has been demonstrated that cancer neoantigens are important targets of cancer immunoediting and established the initial proof of concept that cancer exome sequencing and epitope prediction algorithms can be used to identify cancer neoantigens. In subsequent preclinical studies, it was demonstrated that neoantigen vaccines can induce neoantigen-specific CD8 and CD4 T cell responses and antitumor immunity. Other investigators used similar strategies in the mouse tumor models MC-38 (colon cancer) and TRAMP-C1 (prostate cancer). The first report of a neoantigen vaccine strategy in humans demonstrated that neoantigen dendritic cell vaccines are capable of generating neoantigen-specific T cell responses in human melanoma patients. Two previous studies confirmed the potential of neoantigen vaccines in treating melanoma patients using neoantigen synthetic long peptide and RNA neoantigen vaccine approaches, respectively. More recent studies have evaluated the importance of neoantigen vaccines in glioblastoma.

Triple-negative breast cancer (TNBC) lacks expression of estrogen receptor, progesterone receptor and HER2. TNBC is associated with an aggressive clinical course, and there are no targeted therapies available. There is strong rationale to target cancer neoantigens in TNBC. First, TNBC is a mutationally complex breast cancer subtype. The relative abundance of somatic mutations in TNBC suggests that neoantigens that can be targeted by neoantigen vaccine therapy are more likely to be present. Second, tumor infiltrating lymphocytes (TILs) are more common in TNBC, and TILs are associated with improved outcome in TNBC following adjuvant, or neoadjuvant chemotherapy. The association between TILs and improved outcome in TNBC highlights the importance of the adaptive immune system in the response to therapy. Third, several recent studies of chemotherapy combined with immune checkpoint inhibition in TNBC suggest that a percentage of patients with TNBC will benefit from combination immunotherapy with durable responses noted. Although these studies are promising, highly effective treatment of TNBC remains an unmet clinical need. Accordingly, there is a need for improved and target-specific TNBC treatment.

SUMMARY

One aspect of the disclosure is a fusion protein comprising at least one triple negative breast cancer (TNBC)-associated neoantigen epitope joined to a mutant ubiquitin protein. In certain aspects, the ubiquitin may comprise a mutation that enhances antigenic processing of the fusion protein. In certain aspects, the ubiquitin may comprise a mutation, which may be a deletion mutation, an insertion mutation or a substitution mutation, that prevents de-ubiquination of the fusion protein. In certain aspects, the mutation may be at a position corresponding to G76 of SEQ ID NO:1. In certain aspects, the mutation may comprise a G76V mutation, or a substitution of a valine, leucine or isoleucine for a glycine at a position corresponding to position 76 of SEQ ID NO:1. In certain aspects, the mutant ubiquitin may comprise an amino acid sequence at least 90%, at least 95% or at least 97% identical to SEQ ID NO:1, wherein the amino acid at the position corresponding at position 76 of SEQ ID NO:1 is a valine, leucine or isoleucine. In certain aspects, the mutant ubiquitin may comprise SEQ ID NO:1. In certain aspects, the at least one TNBC-associated neoantigen epitope may be from a protein selected from the group consisting of tumor protein 53 (TP53), SRY-box transcription factor 17 (Sox17), lysine methyltransferase 2d (KMT2D), Phosphoinositide-3-Kinase Regulatory Subunit 1 (PIK3R1), Euchromatic Histone Lysine Methyltransferase 1 (EHMT1), Euchromatic Histone Lysine Methyltransferase 1 (EHMT1), Mucin 6, Oligomeric Mucus/Gel-Forming (Much), Zinc Finger Protein 165 (ZNF165), Copine 3 (CPNE3), Transmembrane Protein 101 (TMEM101), pantothenate kinase 3 (PanK3), plekho1 1, Exocyst Complex Component 4 (EXOC4), Leucine Rich Repeat Containing 27 (LRRC27), exportin 4 (Xpo4), Pttg1, Nei Like DNA Glycosylase 3 (Neil3), Hist1 h3e protein, Protein Kinase AMP-Activated Non-Catalytic Subunit Gamma 1 (Prkg1), Mitogen-Activated Protein Kinase Kinase Kinase 6 (Map3k6), BC057079, Met.I851, Alanyl-TRNA Synthetase 2, Mitochondrial (AARS2), Dynein Cytoplasmic 1 Heavy Chain 1 (Dync1h1), Deltex E3 Ubiquitin Ligase 2 (DTX2), PML-RARA Regulated Adaptor Molecule 1 (PRAM1), Centromere Protein F (Cenpf), glycerol kinase (GyK), G-protein-coupled receptor family C, member 5, group A (Gprc5a), Inositol 1,4,5-Trisphosphate Receptor Interacting Protein (ITPRIP), zinc finger protein 142 (Zfp142), DExH-Box Helicase 58 (Dhx58), isochorismatase domain containing 2a (Isoc2a), Gen1 Holliday Junction 5' Flap Endonuclease (Gen1), Glycosylphosphatidylinositol Specific Phospholipase D1 (GPLD1), Immunoglobulin Superfamily Member 9 (Igsf9), Leukotriene A4 Hydrolase (Lta4h), Glutaminyl-tRNA synthetase (Qars), Protein Disulfide Isomerase Family A Member 5 (PDIA5), TBC1 Domain Family Member 22A (TBC1D22A), GDNF Inducible Zinc Finger Protein 1 (GZF1), Transient Receptor Potential Cation Channel Subfamily C Member 4 Associated Protein (TRPC4AP), Polycomb Group Ring Finger 2 (PCGF2), Caseinolytic Mitochondrial Matrix Peptidase Chaperone Subunit B (CLPB), Signal Induced Proliferation Associated 1 Like 3 (SIPA1L3), TBC1 Domain Family Member 20 (TBC1D20), Succinate Dehydrogenase Complex Flavoprotein Subunit A (SDHA), Coiled-Coil Domain Containing 6 (CCDc6), Laminin Subunit Alpha 5 (Lama5), Sacsin Molecular Chaperone (Sacs), and Zinc Finger Protein 611 (ZNF611). The at least one TNBC-associated neoantigen epitope may comprise an epitope corresponding to an epitope disclosed herein. In certain aspects, the at least one TNBC-associated neoantigen epitope may comprise an epitope corresponding to an epitope represented by a sequence selected from the group consisting of SEQ ID NOS:2-20, SEQ ID NO:25-36, and SEQ ID NOS:55-96. The at least one TNBC-associated neoantigen epitope may comprise an amino acid sequence at least 95% identical to a sequence selected from the group consisting of SEQ ID NOS:2-20, SEQ ID NO:25-36, and SEQ ID NOS:55-96, wherein the at least one TNBC-associated neoantigen epitope maintains the altered amino acid, relative to the wild-type sequence, which may be the bolded amino acid within the epitope as shown in Table 1, Table 2, Table 3, or as illustrated by the arrow in FIGS. 3A, 3C, 3E, 3G, 3I, 3K or FIG. 8A, 8D, 8G, or 8J. In certain aspects, the at least one TNBC-associated neoantigen epitope may comprise an amino acid sequence selected from the group consisting of SEQ ID NOS:2-20, SEQ ID NO:25-36, and SEQ ID NOS: 55-96.

In certain aspect, the fusion protein may comprise a plurality of TNBC-associated neoantigen epitopes, which may be joined to one another to form a polyepitope protein that is joined to the mutant ubiquitin protein. The mutant ubiquitin protein may be joined to the amino-terminal end or the carboxyl end of the polyepitope protein. In such aspects, each epitope of the plurality of epitopes may be, independently, from a protein selected from the group consisting of TP53, Sox17, KMT2D, PIK3R1, EHMT1, Much, ZNF165, CPNE3, TMEM101, PanK3, plekho1 1, EXOC4, LRRC27, Xpo4, Pttg1, Neil3, Hist1 h3e, Prkg1, Map3k6, BC057079, Met.I851, Alanyl-TRNA Synthetase 2, Mitochondrial (AARS2), Dync1h1, DTX2, PRAM1, Cenpf, GyK, Gprc5a, ITPRIP, Zfp142, Dhx58, Isoc2a, Gen1, GPLD1, Igsf9, Lta4h, Qars, PDIA5, TBC1D22A, GZF1, TRPC4AP, PCGF2, CLPB, SIPA1L3, TBC1D20, SDHA, CCDc6, Lama5, Sacs, and ZNF611. In certain aspects, each epitope of the plurality of epitopes may comprise an epitope corresponding to an epitope disclosed herein. In certain aspects, each epitope of the plurality of epitopes may comprise an epitope corresponding to an epitope represented by a sequence selected from the group consisting of SEQ ID NOS:2-20, SEQ ID NO:25-36, and SEQ ID NOS:55-96. In certain aspects, each epitope of the plurality of epitopes may comprise an amino acid sequence at least 95% identical to a sequence selected from the group consisting of SEQ ID NOS:2-20, SEQ ID NO:25-36, and SEQ ID NOS:55-96, wherein the epitope comprises the bolded amino acid within the epitope as shown in Table 1, Table 2, Table 3, or as illustrated by the arrow in FIGS. 3A, 3C, 3E, 3G, 3I, 3K or FIG. 8A, 8D, 8G, or 8J. In certain aspects, each epitope of the plurality of epitopes comprises an amino acid sequence selected from the group consisting of SEQ ID NOS:2-20, SEQ ID NO:25-36, and SEQ ID NOS:55-96.

One aspect of the disclosure is a nucleic acid molecule comprising a nucleic acid sequence encoding a fusion protein of the disclosure.

One aspect of the disclosure is a vector comprising a nucleic acid molecule of the disclosure. The vector may be a plasmid or a viral vector (e.g., an adeno-associated virus vector). The vector may be an expression vector, and the nucleic acid sequence may be operably linked to a promoter that may drive expression of the nucleic acid sequence.

One aspect of the disclosure is a composition comprising a fusion protein of the disclosure, a nucleic acid molecule of the disclosure, or a vector of the disclosure. The composition may comprise a physiologically compatible excipient, and may be a vaccine vector.

One aspect of the disclosure is a kit comprising a fusion protein of the disclosure, a nucleic acid molecule of the disclosure, a vector of the disclosure, or a vaccine composition of the disclosure.

One aspect of the disclosure is a vaccine composition comprising a fusion protein comprising at least one TNBC-associated neoantigen epitope and at least one mutant ubiquitin protein, or a nucleic acid molecule encoding such a fusion protein. The at least one TNBC-associated neoantigen epitope may be selected from the TNBC-associated neoantigen epitopes of the present disclosure, the at least one TNBC-associated neoantigen epitope may comprise a TNBC-associated neoantigen polyepitope, the at least one mutant ubiquitin tag may be fused to an N-terminus of the at least one TNBC-associated neoantigen epitope, and/or the at least one mutant ubiquitin protein may comprise a G76V mutation.

One aspect of the disclosure is a method of treating Triple Negative Breast Cancer (TNBC) in an individual, the method comprising administering a therapeutically effective amount of a fusion protein of the disclosure, a nucleic acid molecule of the disclosure, a vector of the disclosure, or a vaccine composition of the disclosure. Administration may occur following TNBC tumor removal surgery and/or neoadjuvant treatment such as chemotherapy. In certain aspects, the method may comprise administering a checkpoint inhibitor, which may be a PD-1 or PD-L1 inhibitor.

One aspect of the disclosure is a method of protecting an individual against Triple Negative Breast Cancer (TNBC), the method comprising administering a therapeutically effective amount of a fusion protein of the disclosure, a nucleic acid molecule of the disclosure, a vector of the disclosure, or a vaccine composition of the disclosure.

One aspect is a method of treating Triple Negative Breast Cancer (TNBC) in a human subject, the method comprising administering a therapeutically effective amount of a neoantigen DNA vaccine composition comprising a nucleic acid molecule encoding a fusion protein comprising at least one TNBC-associated neoantigen epitope and at least one mutant ubiquitin tag. Administration may follow TNBC tumor removal surgery, and/or neoadjuvant chemotherapy. In certain aspects, the at least one TNBC-associated neoantigen epitope may be identified from at least one TNBC tumor sample removed during the TNBC tumor removal surgery, and the at least one TNBC-associated neoantigen epitope may be identified based on exome sequencing and RNA sequencing of the at least one TNBC tumor sample.

One aspect is a fusion protein of the disclosure, a nucleic acid molecule of the disclosure, a vector of the disclosure, or a vaccine of the disclosure, for use in protecting an individual against Triple Negative Breast Cancer (TNBC).

One aspect is a fusion protein of the disclosure, a nucleic acid molecule of the disclosure, a vector of the disclosure, or a vaccine of the disclosure, for use in treating an individual for Triple Negative Breast Cancer (TNBC).

BRIEF DESCRIPTION OF THE DRAWINGS

The embodiments described herein may be better understood by referring to the following description in conjunction with the accompanying drawings.

FIGS. 2A-2C are exemplary embodiments of generation and validation of a personal, polyepitope DNA neoantigen vaccine for TNBC patients in accordance with the present disclosure. FIG. 2A shows a filtering plot: counts of mutations at each stage of the mutation filtering process. All protein-altering mutations were initially considered, followed by prioritization of those with variants expressed in the RNA, then predicted binding affinities less than 500. The higher final number of mutations represented in the vaccines reflect the decision to relax binding and expression thresholds slightly to identify additional peptides for inclusion in some cases. FIG. 2B shows a waterfall plot: mutational landscape of samples, showing protein-altering mutations in cancer-related genes. Genes are ordered by frequency and colored by alteration type. FIG. 2C shows a table of patient baseline characteristics and immune and clinical responses to neoantigen DNA vaccination.

FIGS. 8A-8L are exemplary embodiments of individual overlapping neoantigens induced immune response after in vitro stimulation of PBMCs collected from polyepitope DNA vaccinated triple negative breast cancer patients in accordance with the present disclosure. Autologous PBMCs were stimulated with pooled candidate neoantigens for 12 days. For each patient, T cell IFN-γ ELISPOT assays against individual overlapping neoantigens, pooled Ops and individual minimum peptide were performed on day 12 by co-culturing stimulated PBMCs overnight with autologous, irradiated PBMCs pulsed with the individual overlapping candidate neoantigens. The sequence of individual overlapping neoantigens from representative patients are listed with the IFN-γ secretion ELISPOT assay against individual overlapping peptides in (FIG. 8A-8C; SEQ ID NO. 25, SEQ ID NO. 26, SEQ ID NO. 27) and (FIG. 8D-8F; SEQ ID NO. 28, SEQ ID NO. 29, SEQ ID NO. 30) for patient BRC19, (FIG. 8G-8I; SEQ ID NO. 31, SEQ ID NO. 32, SEQ ID NO. 33) and (FIG. 8J-8L; SEQ ID NO. 34, SEQ ID NO. 35, SEQ ID NO. 36) BRC08. Different overlapping peptides are indicated in color (black: OP-1; gray: OP-2; white: OP-3). The Negative controls in the ELISPOT assays included responder T cells cultured with no peptide (number of spot-forming cells per 106 cells was 30-150) or irrelevant peptide (number of spot-forming cells per 106 cells was 220-400). The background without peptide was subtracted from the experimental condition in each case. Data are presented as means±SEM (n=2-3 wells per peptide in ELISpot assay) and are representative of three independent experiments. Samples were compared using unpaired, two-tailed Student test (*, P<0.05; **, P<0.01; ns, no significant difference); SFC, spot-forming cells. All T-cell lines originated from 2 wk-post 3rd vax PBMCs; ELISPOT experiments were performed in duplicate or triplicate wells per condition.

FIGS. 10A-10D are exemplary embodiments of IFN-γ secretion based on neoantigen-stimulated T cells from polyepitope DNA vaccinated TNBC patients overlapping peptides in accordance with the present disclosure. Autologous PBMCs were stimulated with pooled candidate neoantigens for 12 days. For each neoantigen that induced mutant peptide-specific immune response, intracellular IFN-γ secretion assays of stimulated T cells against overlapping neoantigens were performed on day 12 by co-culturing stimulated PBMCs overnight with autologous, irradiated PBMCs pulsed with the overlapping peptides or medium only. The flow cytometry data from patient BRC18 (FIG. 10A) and (FIG. 10B), BRC19 (FIG. 10C), and BRC08 (FIG. 10D) are shown.

FIGS. 11A & 11B show schematic DNA constructs encoding eight polyepitope model antigens (peptide sequences listed in Table 4). FIG. 11A: polyepitope P20 and M20 differ only in the position of epitopes pp65 and M1. FIG. 11B: the polyepitope constructs were subcloned into a retroviral vector driven by the MSCV promoter. The HA-tag and IRES-GFP were included to facilitate the in vitro detection of polyepitope protein production. Ub$^{mut}$, a mutated (G76V) ubiquitin. FIGS. 11C & 11D show immunoblot (IB) analysis of the polyepitope proteins. FIG. 11C: HeLa-A2 cells were transduced with indicated polyepitope constructs. Arrowheads indicate the ubiquitinated polyepitope proteins. FIG. 11D: HA/GFP ratio was used to quantify relative levels of polyepitope proteins. Results combined from three independent experiments (mean±SEM) were shown. FIGS. 11E-11G. Presentation of antigens by the transduced HeLa-A2 cells. FIG. 11E shows surface staining of the SVG9/HLA-A2 complexes with a TCR-mimic antibody. Mean fluorescence intensity (MFI) of the SVG9/HLA-A2 signal relative to MFI of the co-expressed GFP (mean±SEM, in triplicates) was shown. FIG. 11F shows specific lysis of transduced HeLa-A2 cells by SVG9-specific cytotoxic T cells was measured by a51 Cr-releasing cytotoxicity assay (E:T=25:1). FIG. 11G shows DNA vaccines induced a G209-specific immune response in HHD II mice was measured by an IFN-γ ELISpot assay (mean±SEM, n=8). These experiments were repeated at least once and representative results were shown. FIG. 11H: Representative dot plots showing SVG9/HLA-A2 tetramer staining of CD8+ spleen cells from the vaccinated HHD II mice. Numbers indicate frequencies in each quadrant. *P<0.05, ***P<0.001, t-test.

FIG. 13A illustrates scheduling of DNA vaccination and anti-PD-L1 treatment. Wild-type female C57BL/6 mice (n=15 per group) were vaccinated by gene gun on days −4, −1, and 2 and challenged with 106 E0771 cells on day 0. Anti-PD-L1 or control antibodies were administered every 3-4 days. FIG. 13B: Tumors were measured with electronic calipers of the longest (L) and perpendicular (W) diagonals. Tumor sizes (mean±SEM) were calculated as (L×W2)/2. Results from one of the three independent experiments were shown. FIG. 13C: In a parallel experiment, tumors were harvested and dissociated to prepare single cell suspension on day 14. TILs were analyzed by Lrrc27/Db dextramer staining and flow cytometry. P=0.0381, one-way ANOVA. FIG. 13D: Tumor-draining lymph nodes (LN) were harvested on day 14. LN cells were used in an IFN-γ ELISpot assay and stimulated with selected MT peptides (8- to 10-mer). FIG. 13E: Spleen cells were harvested from treated tumor-bearing mice on day 26 and used in an IFN-γ ELISpot assay. The studies were repeated once and similar results were obtained. Error bars, SEM. *P<0.05, P<0.01, *P<0.001, t-test.

FIG. 14A. Comparison of IFN-γ ELISpot results (mean±SEM) induced by polyepitope $Ub^{mut}$-E0771 DNA vaccine and SLP vaccine. Wildtype C57BL/6 mice were vaccinated with $Ub^{mut}$-E0771 vaccine or a mixture of three SLPs. The schedule for both platforms was optimized independently. The IFN-γ ELISpot assay was performed on the same day when immune responses are at peak level. The experiment was repeated once and similar results were obtained. FIG. 14B Specificity of DNA vaccine-generated immune response towards neoantigens (MT) over corresponding WT peptides. An IFN-γ ELISpot assay was performed by using 8- to 10-mer MT and WT peptides at different concentrations. Results shown were from one of the two independent experiments. Results generated with high (2.5 μg/ml) and low (10 μg/ml) MT/WT Lrrc27 peptides were also shown. *P<0.05, paired t-test.

FIG. 16A: D3 results showing expression and degradation of polyepitope antigens. FIGS. 16B & 16C: surface expression of WNV SVG9 on HeLa-A2 cells transduced with indicated polyepitope DNA constructs were measured by staining with a TCR-mimic antibody. The expression level was normalized to co-expressed GFP as A2-SVG9/GFP MFI ratio (mean±SEM). FIG. 16D: HeLa-A2 cells transduced with indicated polyepitope constructs were cultured for 2 hours with or without 50 μM of MG132 before subjected to IP. Arrowheads indicate ubiquitinated polyepitope proteins. FIG. 16E: Specific lysis of transduced HeLa-A2 by SVG9-specific T cells as measured by a 51Cr-releasing cytotoxicity assay (E:T=25:1). Target HeLa-A2 cells were transduced with indicated polyepitope constructs. Parental HeLa-A2 cells pulsed with or without SVG9 peptide were used as control. FIG. 16F: DNA vaccines induced immune responses against model antigens in HHD II mice was measured by an IFN-γ ELISpot assay (mean±SEM). The in vitro studies (FIGS. 16A-16E) were repeated at least twice and the in vivo experiment (FIG. 16F) was repeated once. Similar results were obtained. * P<0.05, *** P<0.001, t-test.

FIG. 18A shows 4T1.2 is resistant to anti-PD-L1 monotherapy. 5×105 4T1.2 cells were injected subcutaneously into flanks of Balb/c mice. Starting on day 4, mice were treated with 200 μg of anti-PD-L1 or isotype control antibody (i.p.) every three days for a total of three doses. Tumor sizes were measured with an electronic caliper and calculated as (L×W2)/2. FIG. 18B: Balb/c mice were vaccinated by gene gun with $Ub^{mut}$-4T1.2 or control vector DNA vaccine. Four days following the complete of DNA vaccination, mice were challenged with 106 4T1.2 cells subcutaneously in the flanks. Tumor sizes were measure with an electronic caliper and calculated as L×W. Error bars, SEM. The experiments were repeated once and similar results were obtained.

FIG. 19A shows in vitro peptide-MHC binding assay indicated MT and WT Lrrc27 peptides have equally binding affinity to H-2Db. Control peptide mouse gp100 (EGSRNQDWL) is known to bind weakly to Db. The assay was repeated twice and similar results were obtained. FIG. 19B shows specificity (or cross-reactivity) of immune responses induced by SLP vaccines was assessed by IFNγ ELISpot assay following stimulation with MT or WT peptides. Results from one of the two experiments were shown.

DETAILED DESCRIPTION

Figure 1:
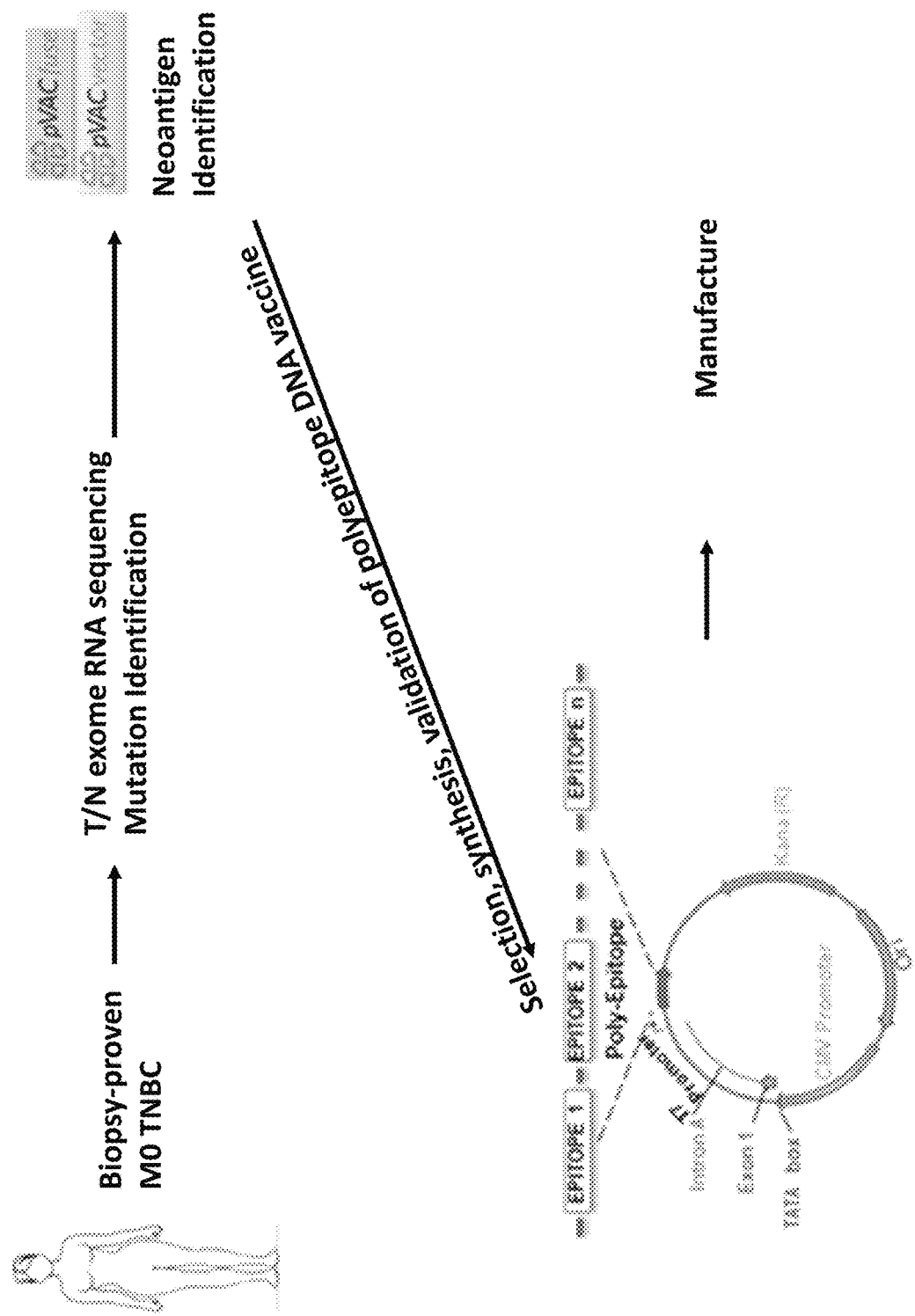
FIG. 1 is an exemplary embodiment of generation and validation of a personal, polyepitope DNA neoantigen vaccine for TNBC patients in accordance with the present disclosure. Somatic mutations were identified by WES of TNBC and germline DNA and their expression confirmed by tumor RNA-seq. Immunizing neoantigens were selected on the basis of HLA binding predictions by pVAC (Methods). Each DNA vaccination will be a 4 mg vaccine administered intramuscularly using a TriGrid electroporation device.

The present disclosure generally relates to methods of protecting an individual against, or treating an individual for, triple negative breast cancer (TNBC) using a neoantigen vaccine. More specifically, the disclosure provides novel neoantigen vaccine compositions in which the components have been stabilized resulting in enhanced antigenic presentation and an improved vaccine response. Stabilization of the vaccine components is achieved through the use of a mutant ubiquitin protein that is fused to at least one TNBC-associated neoantigen epitope. Thus, the present disclosure may generally be practiced by producing a fusion protein comprising a TNBC-associated neoantigen epitope fused to a ubiquitin protein comprising a mutation that stabilizes the fusion protein and enhances antigenic presentation of peptides of the fusion protein, or a nucleic acid molecule encoding such a protein. Such a protein, or nucleic acid encoding such protein, may be administered to an individual to protect them from TNBC or to treat them for TNBC.

Before the present disclosure is further described, it is to be understood that the disclosure is not limited to particular embodiments described, as such may, of course, vary. It is also to be understood that the terminology used herein is for the purpose of describing particular embodiments only, and is not intended to be limiting, since the scope of the present disclosure will be limited only by the claim.

It must be noted that as used herein and in the appended claims, the singular forms "a," "an," and "the" include plural referents unless the context clearly dictates otherwise. For example, a compound refers to one or more compound molecules. As such, the terms "a", "an", "one or more" and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and may also cover other unlisted steps. Similarly, any composition or device that "comprises," "has" or "includes" one or more features is not limited to possessing only those one or more features and may cover other unlisted features.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that vary depending upon the desired properties sought to be obtained by a particular embodiment. In some embodiments, the numerical parameters are be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In embodiments described herein, a nucleic acid is defined as a biopolymer, or large biomolecule, composed of nucleotides linked in a long chain and essential to all known forms of life. Both DNA and RNA are nucleic acids composed of nucleotide chains. Accordingly, a DNA embodiment context may be interchangeable with an RNA embodiment context and vice versa. For example, in some embodiments, the mutant ubiquitin tag is applicable for use in DNA-based vaccines. In other embodiments, the mutant ubiquitin tag is applicable for use in RNA-based vaccines.

Publications disclosed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates, which may need to be independently confirmed. All publications mentioned herein are incorporated herein by reference to disclose and describe the methods and/or materials in connection with which the publications are cited.

Unless defined otherwise, all technical and scientific terms used herein have the same meaning as commonly understood by one of ordinary skill in the art to which the invention belongs. Although any methods and materials similar or equivalent to those described herein can also be used in the practice or testing of the present invention, the preferred methods and materials are now described. Terms and phrases, which are common to the various aspects disclosed herein, are defined below.

One aspect of the disclosure is a fusion protein comprising at least one TNBC-associated neoantigen epitope joined to a mutant ubiquitin protein. As used herein, "neoantigen" refers to an antigen having one or more amino acid modifications compared to the parental antigen. For example, a neoantigen may be a tumor-associated neoantigen, wherein the term "tumor-associated neoantigen" can include a peptide or protein having amino acid modifications due to tumor-specific mutations.

As used herein, "epitope" refers to a portion or fragment of a molecule, such as an antigen, that is recognized by components of the immune system, such as a T cell, particularly when presented in the context of an MHC molecule, B cells, and antibodies. The epitope of a protein, such as a tumor antigen, preferably comprises a continuous or discontinuous portion of said protein and preferably has a length of 5 to 30. In certain aspects, an epitope may comprise a contiguous sequence of an antigen and may be 9, 10, 11, 12, 13, 14, 15, 16, 17, 18, 19, 20, 21, 22, 23, 24, or 25 amino acids in length. In certain aspects, an epitope may comprise a contiguous sequence of an antigen and may be at least 20, 21, 22, 23, 24 or 25 amino acid in length.

As used herein, "ubiquitin" refers to a polypeptide which is ligated to another polypeptide by ubiquitin ligase enzymes. Ubiquitin protein useful for practicing aspects of the disclosure may be from any species of organism. In certain aspects, the ubiquitin is mammalian. In certain aspects, the ubiquitin is human ubiquitin. One example of human ubiquitin is GenBank entry KAI12523438.1

Fusion proteins of the disclosure comprise a mutant ubiquitin protein. Mutant ubiquitin refers to a ubiquitin protein comprising one or more mutations, which may include amino acid deletions, substitutions or insertions. The mutations cause the stability of the fusion protein to be enhanced (i.e., the fusion protein is resistant to de-ubiquination). One example of a sequence of a mutant ubiquitin protein is SEQ ID NO:1. In certain aspects, the mutant ubiquitin comprises a mutation at the position corresponding to position 76 of SEQ ID NO:1. In the present disclosure, the term "corresponding", when used with regard to an amino acid position in a protein, refers to an amino acid position that is in the same general location in the sequence of the protein, as a reference amino acid position in an variant (e.g., allelic variant, a protein from another species) of the protein. For example, wild-type, human ubiquitin (e.g., KAI12523438.1) contains a glycine at position 76. However, due to natural variation (insertions, deletions), the glycine residue in an allelic variant or a ubiquitin protein from other species may be at, for example position 75 or 77. Such a corresponding position may be determined by comparing the sequence surrounding the amino acid position of interest (e.g., position 76). Methods of identifying corresponding amino acid position are known to those in the art.

In certain aspects, the mutant ubiquitin protein comprises an amino acid sequence at least 90%, at least 95%, or at least 97% to SEQ ID NO:1, wherein the amino acid at the position corresponding to amino acid position 76 of SEQ ID NO:1 is a valine, leucine or isoleucine. In certain aspects, the mutant ubiquitin protein comprises SEQ ID NO:1.

The at least one TNBC-associated neoantigen epitope may be from any protein expressed by a TNBC tumor call. In certain aspects, the at least one TNBC-associate neoantigen epitope is from a protein selected from the group consisting of TP53, Sox17, KMT2D, PIK3R1, EHMT1, Much, ZNF165, CPNE3, TMEM101, PanK3, plekho1 1, EXOC4, LRRC27, Xpo4, Pttg1, Neil3, Hist1 h3e, Prkg1, Map3k6, BC057079, Met.I851, Alanyl-TRNA Synthetase 2, Mitochondrial (AARS2), Dync1h1, DTX2, PRAM1, Cenpf, GyK, Gprc5a, ITPRIP, Zfp142, Dhx58, Isoc2a, Gen1, GPLD1, Igsf9, Lta4h, Qars, PDIA5, TBC1D22A, GZF1, TRPC4AP, PCGF2, CLPB, SIPA1L3, TBC1D20, SDHA, CCDc6, Lama5, Sacs, and ZNF611. In certain aspects, the at least one TNBC-associated neoantigen epitope is any TNBC-associated neoantigen epitope disclosed herein. In certain aspects, the at least one TNBC-associated neoantigen epitope is selected from TABLE 1, Table 2, Table 3. In certain aspects, the at least one TNBC-associated neoantigen epitope comprises an epitope represented by a sequence selected from the group consisting of SEQ ID NOS:2-20, SEQ ID NO:25-36, and SEQ ID NOS:55-96. In certain aspects, the at least one TNBC-associated neoantigen epitope comprises an epitope corresponding to an epitope represented by a sequence selected from the group consisting of SEQ ID NOS:2-20, SEQ ID NO:25-36, and SEQ ID NOS:55-96. As used herein, an epitope that corresponds to an epitope represented by an sequence selected from the group consisting of SEQ ID NOS:2-20, SEQ ID NO:25-36, and SEQ ID NOS:55-96 refers to an epitope having an identical, or nearly so (i.e., at least 95%, at least 97%, at least 98%, at least 99% identical) in the corresponding protein from another species. For example, SEQ ID NO:55 represents an epitope from mouse Tmem10. A corresponding epitope may be an epitope having an identical, or nearly identical, sequence from human Tmem10. In certain aspects, the at least one TNBC-associated neoantigen epitope comprises an amino acid sequence at least 95% identical to a sequence selected from the group consisting of SEQ ID NOS:2-20, SEQ ID NO:25-36, and SEQ ID NOS:55-96, wherein the epitope comprises the bolded amino acid within the epitope as shown in Table 1, Table 2, Table 3, or as illustrated by the arrow in FIGS. 3A, 3C, 3E, 3G, 3I, 3K or FIG. 8A, 8D, 8G, or 8J. In certain aspects, the at least one TNBC-associated neoantigen epitope may comprise an amino acid sequence selected from the group consisting of SEQ ID NOS:2-20, SEQ ID NO:25-36, and SEQ ID NOS: 55-96.

In certain aspects of the disclosure, several TNBC-associated neoantigen epitopes may be joined to form a polyepitope protein, which may then be joined to the mutant ubiquitin protein. Thus, in certain aspects, the fusion protein comprises a plurality of TNBC-associated neoantigen epitopes. In certain aspects, each epitope of the plurality of epitopes is, independently, from a protein selected from the group consisting of TP53, Sox17, KMT2D, PIK3R1, EHMT1, Much, ZNF165, CPNE3, TMEM101, PanK3, plekho1 1, EXOC4, LRRC27, Xpo4, Pttg1, Neil3, Hist1 h3e, Prkg1, Map3k6, BC057079, Met.I851, Alanyl-TRNA Synthetase 2, Mitochondrial (AARS2), Dync1h1, DTX2, PRAM1, Cenpf, GyK, Gprc5a, ITPRIP, Zfp142, Dhx58, Isoc2a, Gen1, GPLD1, Igsf9, Lta4h, Qars, PDIA5, TBC1D22A, GZF1, TRPC4AP, PCGF2, CLPB, SIPA1L3, TBC1D20, SDHA, CCDc6, Lama5, Sacs, and ZNF611. In certain aspects, each epitope of the plurality of epitopes comprises an epitope corresponding to an epitope disclosed herein. In certain aspects, each epitope of the plurality of epitopes, independently, comprises an epitope corresponding to an epitope represented by a sequence selected from the group consisting of SEQ ID NOS:2-20, SEQ ID NO:25-36, and SEQ ID NOS:55-96. In certain aspects, each epitope of the plurality of epitopes, independently, comprises an amino acid sequence at least 95% identical to a sequence selected from the group consisting of SEQ ID NOS:2-20, SEQ ID NO:25-36, and SEQ ID NOS:55-96, wherein the epitope comprises the bolded amino acid within the epitope as shown in Table 1, Table 2, Table 3, or as illustrated by the arrow in FIGS. 3A, 3C, 3E, 3G, 3I, 3K or FIG. 8A, 8D, 8G, or 8J. In certain aspects, each epitope of the plurality of epitopes, independently, may comprise an amino acid sequence selected from the group consisting of SEQ ID NOS:2-20, SEQ ID NO:25-36, and SEQ ID NOS:55-96.

One aspect of the disclosure is a nucleic acid molecule comprising a nucleic acid sequence encoding a fusion protein of the disclosure. Such nucleic acid molecules may comprise DNA, RNA, or combinations thereof. Nucleic acid molecules of the disclosure may comprise natural nucleotides (i.e., not modified) or they may comprise modified nucleotides. For example, nucleotides may be modified so that they are more stable and less resistant to degradation.

One aspect of the disclosure is a vector comprising a nucleic acid molecule of the disclosure. Examples of vectors suitable for practicing aspects of the disclosure include, but are not limited to, plasmids and viral vectors such as a cytomegalovirus (CMV) vector, a retrovirus vector, an adenovirus vector, an adeno-associated virus vector, a herpes virus vector, a vaccinia virus vector, a poliovirus vector, a Sindbis virus vector, or any other DNA or RNA virus vector. In certain aspects, a vector may be a pseudotyped lentiviral or retroviral vector. In certain aspects, a vector can be a DNA plasmid. In certain aspects, a vector may be a DNA plasmid comprising viral components and plasmid components to enable nucleic acid molecule delivery and expression. In certain aspects, the vector may be an expression vector that comprises at least one promoter operably linked to the nucleic acid molecule encoding a fusion protein of the disclosure. As used herein, "operably linked" means the promoter is in the correct position and orientation with respect to the nucleic acid such that it controls initiation of RNA polymerase and expression of the nucleic acid molecule encoding a fusion protein of the disclosure.

One aspect of the disclosure is a composition comprising a fusion protein of the disclosure, a nucleic acid molecule encoding a fusion protein of the disclosure of the disclosure, and/or a vector of the disclosure. A composition of the disclosure may comprise a solvent, which may be an aqueous solvent, an organic solvent or mixtures thereof. In certain aspects, a composition of the disclosure may comprise other ingredients, such as, salts, buffers, stabilizing agents and the like. In certain aspects, the composition may comprise a vaccine composition. A vaccine composition of the disclosure refers to a composition comprising a fusion protein of the disclosure, a nucleic acid molecule encoding a fusion protein of the disclosure of the disclosure, and/or a vector of the disclosure, wherein the vaccine composition is intended for administration to an individual for the purpose of eliciting an immune response. Vaccine compositions of the disclosure may be formulated using a carrier. "Carriers" as used herein include pharmaceutically acceptable carriers, excipients, or stabilizers which are nontoxic to the cell or individual being exposed thereto at the dosages and concentrations employed. A "pharmaceutically acceptable carrier" is an excipient that does not interfere with the effectiveness of the biological activity of a composition of the disclosure. Often the physiologically acceptable carrier is an aqueous pH buffered solution. Examples of physiologically acceptable carriers include, but are not limited to, buffers such as phosphate, citrate, and other organic acids, Hanks' solution, Ringer's solution, or physiological saline buffer; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

One aspect of the disclosure is a kit comprising a fusion protein of the disclosure, a nucleic acid molecule encoding a fusion protein of the disclosure of the disclosure, a vector of the disclosure, a composition of the disclosure and/or a vaccine composition of the disclosure. Kits may comprise associated components, such as, but not limited to, cells, cell culture media, buffers, labels, containers, vials, syringes, instructions for using the kit, and the like.

One aspect of the disclosure is a method of protecting an individual from Triple Negative Breast Cancer (TNBC), the method comprising administering to the individual a therapeutically effective amount of a fusion protein of the disclosure of the disclosure, a vector of the disclosure, a composition of the disclosure and/or a vaccine composition of the disclosure.

One aspect of the disclosure is a method of treating Triple Negative Breast Cancer (TNBC) in an individual, the method comprising administering to the individual a therapeutically effective amount of a fusion protein of the disclosure, a vector of the disclosure, a composition of the disclosure and/or a vaccine composition of the disclosure.

One aspect of the disclosure is a method of treating Triple Negative Breast Cancer (TNBC) in an individual, the method comprising administering a therapeutically effective amount of a neoantigen DNA vaccine composition comprising at least one TNBC-associated neoantigen epitope joined to a mutant ubiquitin protein. In such a method, the at least one neoantigen epitope may be identified from a tumor sample from the individual having TNBC. In certain aspects, the at least one neoantigen epitope is identified based on exome sequencing and/or RNA sequencing.

In methods of the disclosure, the dose administered to a subject in a method of the invention can be any dose suitable for treating or preventing TNBC. In conjunction with the present disclosure, those skilled in the art are capable of identifying a dose appropriate for the chosen formulation and method of delivery.

In methods of the disclosure, fusion proteins, nucleic acid molecules, vectors, or compositions, including vaccine compositions, of the invention may be administered by any route suitable for the subject being treated. Such routes of administration include, but are not limited to, injection, including parenteral administration, intravenous, intraperitoneal, intramuscular, and subcutaneous injection, oral administration, transmucosal administration, transdermal administration, topical administration, nasal administration, or ocular administration.

It is known in the art that cancers may be "staged" using a numerical scale that ranges from zero to four, with higher numbers indicating progressively larger and more invasive cancers. In TNBC treatment methods of the disclosure, the TNBC may be at any stage. In certain aspects, the TNBC may be Stage 0. In certain aspects, the TNBC may be Stage 1. In certain aspects, the TNBC may be Stage 2. In certain aspects, the TNBC may be Stage 3. In certain aspects, the TNBC may be Stage 4. Methods of staging TNBC are known to those skilled in the art.

In TNBC treatment methods of the disclosure, the fusion protein, nucleic acid molecule, vector or compositions, including vaccine compositions, of the disclosure may be administered prior to or following TNBC tumor removal. In certain aspects, the fusion protein, nucleic acid molecule, vector or compositions, including vaccine compositions, of the disclosure may be administered prior to or following neoadjuvant therapy. Examples of such neoadjuvant therapies include, but are not limited to chemotherapy, hormone therapy, and radiation therapy.

In certain aspects of TNBC treatment methods of the disclosure, the fusion protein, nucleic acid molecule, vector or compositions, including vaccine compositions, of the disclosure may be administered in conjunction with a check point inhibitor. The check point inhibitor may be administered prior to, at the same time as, or following administration of the fusion protein, nucleic acid molecule, vector or compositions, including vaccine compositions, of the disclosure. Examples of suitable check point inhibitors include, but are not limited to, PD-1 inhibitors, PD-L1 inhibitors, CTLA-4 inhibitors, and LAG-3 inhibitors.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Cancer neoantigens are important targets of cancer immunotherapy. Neoantigen vaccines have the potential to induce highly specific antitumor immune responses with minimal risk of autoimmunity. As disclosed herein, a neoantigen DNA vaccine platform capable of efficiently presenting HLA class I and II epitopes has been developed. To test the safety, feasibility and efficacy of this platform, a phase 1 clinical trial was performed in triple negative breast cancer patients with persistent disease following neoadjuvant chemotherapy.

Expressed genetic alterations in each subject's breast cancer were identified by tumor/normal exome sequencing and tumor RNA sequencing. The pVAC-Seq suite of software tools was used to identify and prioritize cancer neoantigens. Neoantigen DNA vaccines were designed and manufactured at Washington University School of Medicine. Neoantigen DNA vaccines were administered with an electroporation device following completion of standard of care therapy. Safety was measured by clinical and laboratory evaluation. Immune responses were assessed by ELISPOT, flow cytometry and TCR sequencing.

18 subjects received three doses of a neoantigen DNA vaccine. Preferably, vaccine compositions of the present disclosure are each administered in an amount (i.e., a therapeutically effective amount) that is protective or provides a protective effect against TNBC recurrence/progression. The vaccinations were well tolerated with limited adverse events, primarily related to injection site reactions. Neoantigen-specific immune responses were induced in 16/18 patients as measured by ELISPOT and flow cytometry. At a median follow up of 36 months, progression-free survival was observed in 16/18 patients (p=0.033).

Accordingly, as disclosed herein, neoantigen DNA vaccines are safe, feasible, and capable of inducing a neoantigen-specific immune response as supported by evidence of improved disease-free survival compared to historical controls.

In exemplary embodiments, the present disclosure focuses on a neoantigen DNA vaccine strategy. The observation that direct administration of recombinant DNA can generate potent immune responses established the field of DNA vaccines in the early 1990s. Since that time, DNA vaccines have remained an area of intense research interest, and vaccines targeting infectious disease agents and cancers have progressed into clinical trials. The molecular flexibility of the DNA vaccine platform allows targeting of multiple neoantigens using a single polyepitope DNA vaccine. A neoantigen DNA vaccine platform has been designed that allows targeting of multiple cancer neoantigens using a polyepitope insert. This platform also integrates a mutant ubiquitin molecule: $NH_2$-MQIFVKTLTGKTITLEVEPSD-TIENVKAKIQDKEGIP PDQQRLIFAGKQLEDGRTLS-DYNIQKESTLHLVLRLRGV-COOH (SEQ ID NO. 1) in order to promote epitope generation and display, as described in Li et al., *Genome Med.* 13, 56 (2021), which is herein incorporated by reference in its entirety. In the present disclosure, a TriGrid electroporation device was used to administer the neoantigen DNA vaccines. Electroporation dramatically increases DNA uptake by muscle cells, antigen expression, and immunogenicity. Of particular note, electroporation has now been used successfully in non-human primates, with responses at levels previously not observed with other DNA vaccine approaches and similar to or superior to responses induced by live vectors.

Embodiments of the present disclosure describe safety, immunogenicity, and clinical observations of a phase 1 clinical trial of a neoantigen DNA vaccine strategy in the adjuvant setting in patients with persistent TNBC following neoadjuvant chemotherapy (NCT02348320). Significant reduction in the incidence/progression of TNBC is disclosed by the examples and embodiments herein.

Example A

Materials and Methods

Clinical trial. The clinical protocol was reviewed and approved by the Institutional Review Board at Washington University School of Medicine. In order to be eligible for the clinical trial, patients needed to have persistent TNBC following neoadjuvant chemotherapy without evidence of metastatic disease. Patients with evidence of progressive breast cancer or autoimmune disorders were excluded. Subjects enrolled into the protocol provided consent for genome sequencing and dbGaP-based data sharing, and provided germline and tumor DNA samples for sequencing. A total of 35 patients were consented for trial. Subjects were excluded due to complete pathological response after neoadjuvant chemotherapy, DCIS on surgical pathology, insufficient tumor material for DNA sequencing, patient withdrawal, and disease progression. Ultimately 18 subjects received neoantigen DNA vaccines.

All subjects were vaccinated with 4 mg of neoantigen DNA vaccine at Day 1, Day 29±7, and Day 57±7 with at least 21 days between injection days. Each neoantigen DNA vaccine was administered intramuscularly using a TriGrid™ electroporation device (ICHOR Medical Systems, San Diego, CA). Peripheral blood was drawn before, during, and after vaccination. Peripheral blood mononuclear cells (PBMC) were isolated through density centrifugation using Ficoll-Paque PLUS (GE Healthcare Bio-Science AB, Sweden) and cryopreserved as cell suspension with some aliquots as cell pellets. Each subject was followed for at least 12 months. The primary objective of the clinical trial was to evaluate the safety of the neoantigen DNA vaccine strategy. Safety was closely monitored after vaccination with eight or more clinical and laboratory assessments in the first six months of the trial. Toxicity was graded according to the National Cancer Institute Common Terminology Criteria for Adverse Events version 4.0. The secondary objective was to evaluate the immunogenicity of the neoantigen DNA vaccine strategy as measured by ELISPOT analysis and multiparametric flow cytometry, surrogates for CD8 T cell function.

Tissue procurement and nucleic acid isolation. Archival tumor samples were obtained. H&E-stained sections were scored by a pathologist for tumor content and necrosis. Only tissue blocks with over 60% tumor purity were selected. DNA from both tumor tissue and PBMC were extracted using the QIAamp DNA Mini Kit (Qiagen Sciences, Maryland) and RNA was extracted from tumor tissues using the High Pure RNA Paraffin kit (Roche, Indianapolis). DNA and RNA quality were determined using a Nanodrop 2000 and quantitated using a Qubit Fluorometer (Life Technologies, Carlsbad, CA).

Exome sequencing. For each subject, tumor/normal DNA samples were processed for whole exome sequencing. Libraries were prepared using Kapa Biosystems NGS kit and captured using the IDT xGen Exome v1 panel, using the manufacturer recommended procedure. Sequence data were generated as either 2×101 bp or 2×126 bp read pairs on an Illumina HiSeq instrument. DNA sample preparation and sequencing was performed in a CLIA compliant space. Sequence alignment and somatic variant calling was performed as described previously, using an ensemble of callers and stringent filtering, followed by variant effect prediction using VEP.

cDNA-capture sequencing. RNA samples were prepared using the Illumina TruSeq Stranded kit to produce cDNA, followed by cDNA capture with the IDT xGen Exome v1 panel. Both steps followed manufacturer recommended protocols with the exception of skipping the ribodepletion step on samples with low RNA yields (BRC45 and BRC10). Sequencing was performed on an Illumina HiSeq instrument, producing either 2×100 bp or 2×126 bp paired-end reads. Reads were trimmed, aligned with HISAT version 2.0.5 and expression quantified using kallisto version 0.43.1 and transcripts from Ensembl release 95.

HLA Typing. All patients' HLA type was determined by PCR-SSOP (ProImmune, Sarasota, FL) using PBMC.

Neoantigen Identification. The pVACtools pipeline was used to identify and shortlist potential high-affinity neoantigens resulting from somatic missense mutations detected by exome sequencing. Briefly, amino acid substitutions corresponding to each of the coding missense mutations were translated into a 25-mer amino acid FASTA sequence, with up to 12 amino acids flanking the substituted amino acid on each side. For each patient, the 25-mer amino acid sequences were then evaluated through all HLA class I peptide-binding algorithms available in pVACtools to predict high affinity mutated (MT) peptides binding to the patient's HLA alleles. Matching WT sequences were evaluated likewise to calculate differences in binding affinities. Mutant peptides were prioritized by binding affinity (IC50 value <500 nm), sequence coverage, expression (of the transcript and mutant allele), variant allele frequency (preferring clonal variants to subclonal) and whether MHC anchor positions harbored the mutation. This produced a high-confidence list of high affinity HLA class I binding neoantigen candidates for experimental validation.

Neoantigen DNA vaccine design and manufacture. Codon-optimized polyepitope inserts encoding prioritized neoantigens were synthesized by Blue Heron Biotech (Bothell, WA) and subsequently cloned into the pING vector. The DNA sequence for $Ub^{mut}$, a mutated (G76V) ubiquitin (SEQ ID NO. 1) was fused to the N-terminus of the polyepitope construct by standard molecular subcloning. Plasmid DNA was stably expressed in *E. coli* DH5a or similar (Blue Heron) and the transformed bacteria were shipped to the Biologic Therapy Core Facility (BTCF) at Washington University School of Medicine. Bacterial cultures were expanded at the BTCF followed by lysis and DNA extraction. Each DNA vaccine was vialed at a concentration of 2 mg/mL. Before release for administration, each DNA vaccine underwent rigorous product release testing to assure purity and integrity of the vaccine. The ability to transform mammalian cells was also confirmed. The results of the product release tests were documented in a Certificate of Analysis which was reviewed and approved by both the principal investigator and BTCF staff.

Peptides. Peptides for immune monitoring were obtained in lyophilized form at >95% purity (Peptide 2.0 Inc., Chantilly, VA). Peptides were dissolved in sterile water or in 4% DMSO dependent on the amino acid sequence.

In vitro T cell analysis. 200,000 PBMCs were plated in each well of a 96-well round bottom plate with RPMI (with 5% human serum, 10 units/mL Penicillin-Streptomycin, 10 mM HEPES buffer, 2 mM L-glutamine, 1× non-essential amino acid). Pooled overlapping peptides corresponding to prioritized neoantigens were used to stimulate PBMCs at 25 and 50 U/mL IL2 was added every 2 days. Control PBMC were stimulated with peptides corresponding to known viral antigens. On day 12, the peptide specific immune reactivity of the T cells was determined by IFN-γ ELISPOT assay. Cultured T cells were stimulated with peptide-pulsed, irradiated autologous PBMC in the ELISPOT plate followed by 20 hours incubation at 37° C. Developed spots were counted in an ELISPOT reader (C.T.L., Shaker Heights, OH).

Sample preparation and DNA Sequencing for TCR. 200,000 PBMCs were plated in each well of a 96-well round bottom plate with RPMI (with 5% human serum, 10 units/mL Penicillin-Streptomycin, 10 mM HEPES buffer, 2 mM L-glutamine, 1× non-essential amino acid). Peptides with confirmed immunogenicity by ELISPOT assay were used to stimulate PBMCs at 25 μM followed by addition of 50 U/mL IL2 was added every 2 days. Control PBMC were stimulated with non-relevant peptides or medium only. On day 12, cells were harvested and genomic DNA was extracted and purified from cells using the QIAGEN Blood and Tissue Kit (Qiagen, Germantown, MD). TCRβ CDR3 regions were amplified and sequenced using ImmunoSEQ (Adaptive Biotechnologies, Seattle, WA). Data were analyzed with ImmunoSEQ software and GraphPad Prism 9.

Flow cytometry. The following anti-human monoclonal antibodies (mAb) were used for cell surface staining: live/dead AF488 (ThermoFisher Scientific, Waltham, MA), CD4-PerCP-Cy5.5 (clone: RPA-T4), CD8-PE (clone: HIT8a), IFN-gamma-APC (clone B27). All antibodies were obtained from BD Bioscience (San Jose, CA). Samples were analyzed on FACSCalibur Alibur (BD Biosciences, Franklin Lakes, New Jersey, U.S), and data were analyzed using FlowJo software.

Statistical analyses. Samples were compared using an unpaired, two-tailed Student's t-test, unless specified.

Results

Treatment with personalized DNA vaccines is feasible and safe. A total of 35 patients with TNBC consented to the trial. 17 subjects were ineligible for the following reasons: complete pathologic response (n=5), insufficient tumor tissue (n=4), patient preference (n=4), or disease progression (n=4). A neoantigen DNA vaccine was administered to 18 subjects. Neoantigen DNA vaccines were designed and manufactured while subjects underwent adjuvant therapy (FIG. 1). After completion of adjuvant therapy, subjects received three neoantigen DNA vaccinations via electroporation at monthly intervals. In general, vaccination was well-tolerated with only one grade 3 event (hypertension) with most of the grade 2 events related to pain at the injection site (13 events out of 54 total), and grade 1 events related to neck pain or myalgia.

Figure 2A:
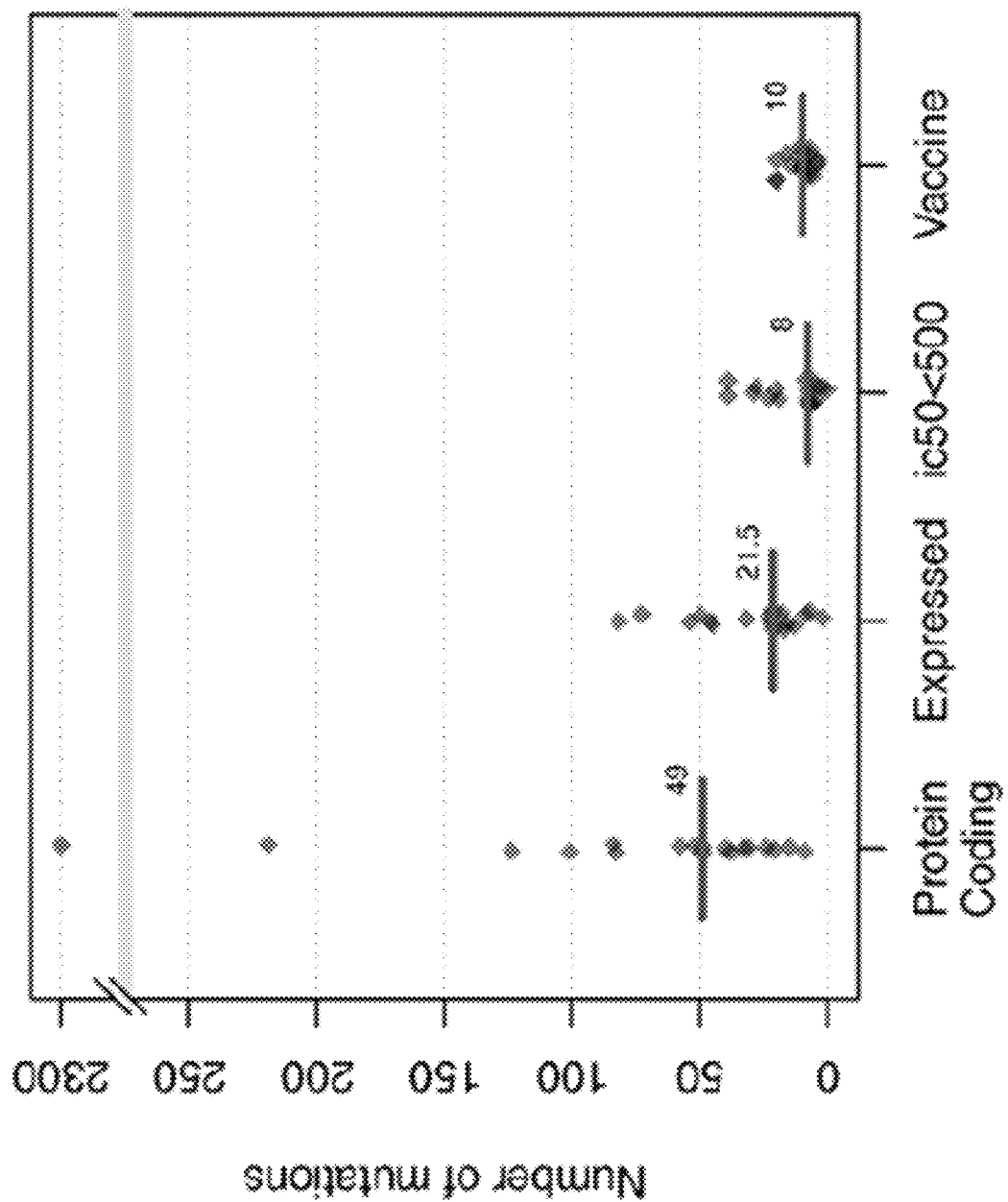
Figure 2B:
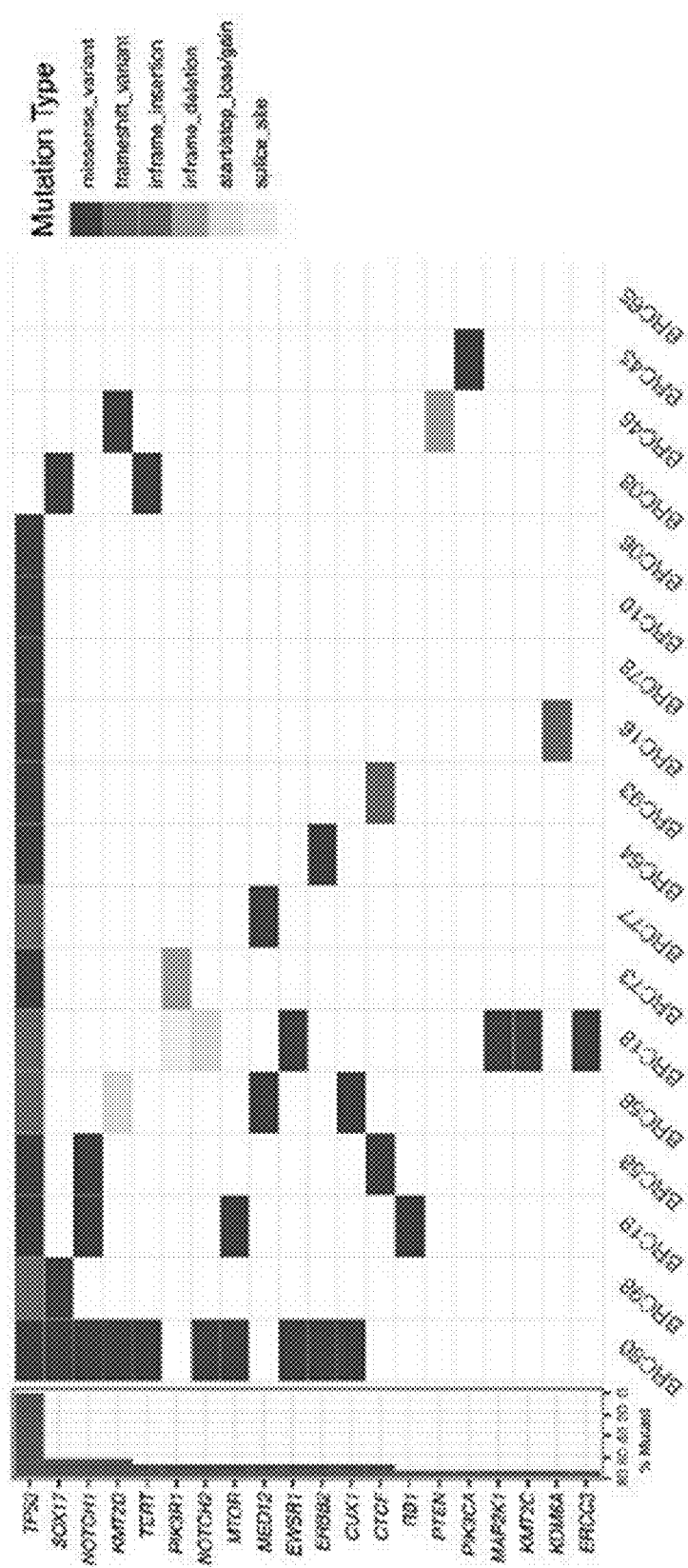
Figures 3A, 3B:
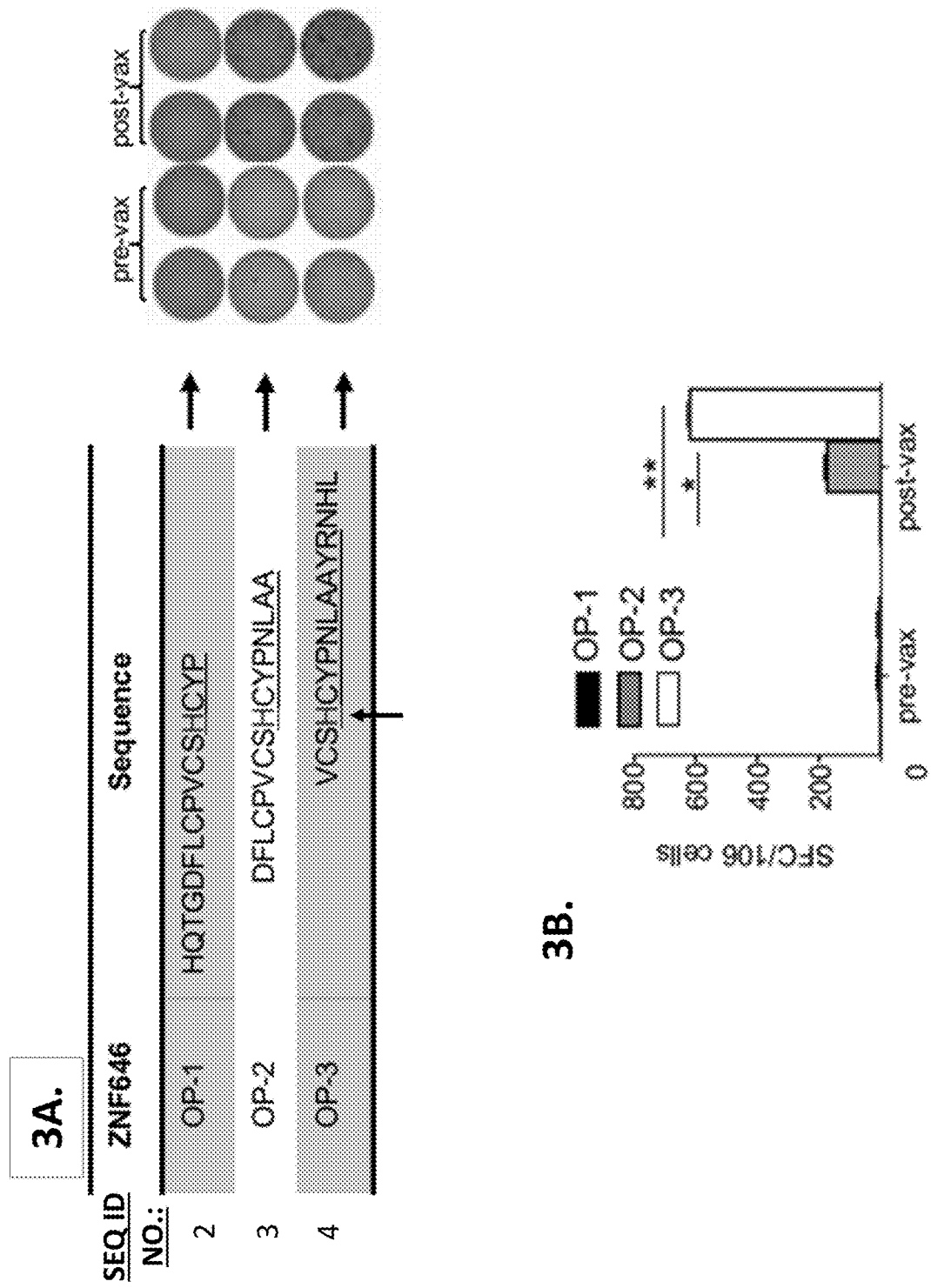
FIGS. 3A-3L are exemplary embodiments of individual overlapping neoantigens induced immune response after in vitro stimulation of PBMCs collected from polyepitope DNA vaccinated triple negative breast cancer patients in accordance with the present disclosure. Autologous PBMCs were stimulated with pooled candidate neoantigens for 12 days. For each patient, T cell IFN-γ ELISPOT assays against individual overlapping neoantigens, pooled Ops and individual minimum peptide were performed on day 12 by co-culturing stimulated PBMCs overnight with autologous, irradiated PBMCs pulsed with the individual overlapping candidate neoantigens. The sequence of individual overlapping neoantigens from representative patients are listed with the IFN-γ secretion ELISPOT assay against individual overlapping peptides in (FIGS. 3A & 3B; SEQ ID NO. 2, SEQ ID NO. 3, SEQ ID NO. 4) and (FIGS. 3C & 3D; SEQ ID NO. 5, SEQ ID NO. 6, SEQ ID NO. 7) for patient BRC45, (FIGS. 3E & 3F; SEQ ID NO. 8, SEQ ID NO. 9, SEQ ID NO. 10) and (FIGS. 3G & 3H; SEQ ID NO. 11, SEQ ID NO. 12, SEQ ID NO. 13) for BRC78, (FIGS. 3I & 3J; SEQ ID NO. 14, SEQ ID NO. 15, SEQ ID NO. 16) and (FIGS. 3K & 3L; SEQ ID NO. 17, SEQ ID NO. 18, SEQ ID NO. 19) for patient BRC18. Different overlapping peptides are indicated in color (black: OP-1; gray: OP-2; white: OP-3). The Negative controls in the ELISPOT assays included responder T cells cultured with no peptide (number of spot-forming cells per 106 cells was 30-150) or irrelevant peptide (number of spot-forming cells per 106 cells was 220-400). The background without peptide was subtracted from the experimental condition in each case. Data are presented as means±SEM (n=2-3 wells per peptide in ELISpot assay) and are representative of three independent experiments. Samples were compared using unpaired, two-tailed Student test (*, P<0.05; **, P<0.01; ns, no significant difference); SFC, spot-forming cells. All T-cell lines originated from 2 wk-post 3rd vax PBMCs; ELISPOT experiments were performed in duplicate or triplicate wells per condition.
Figures 3C, 3D:
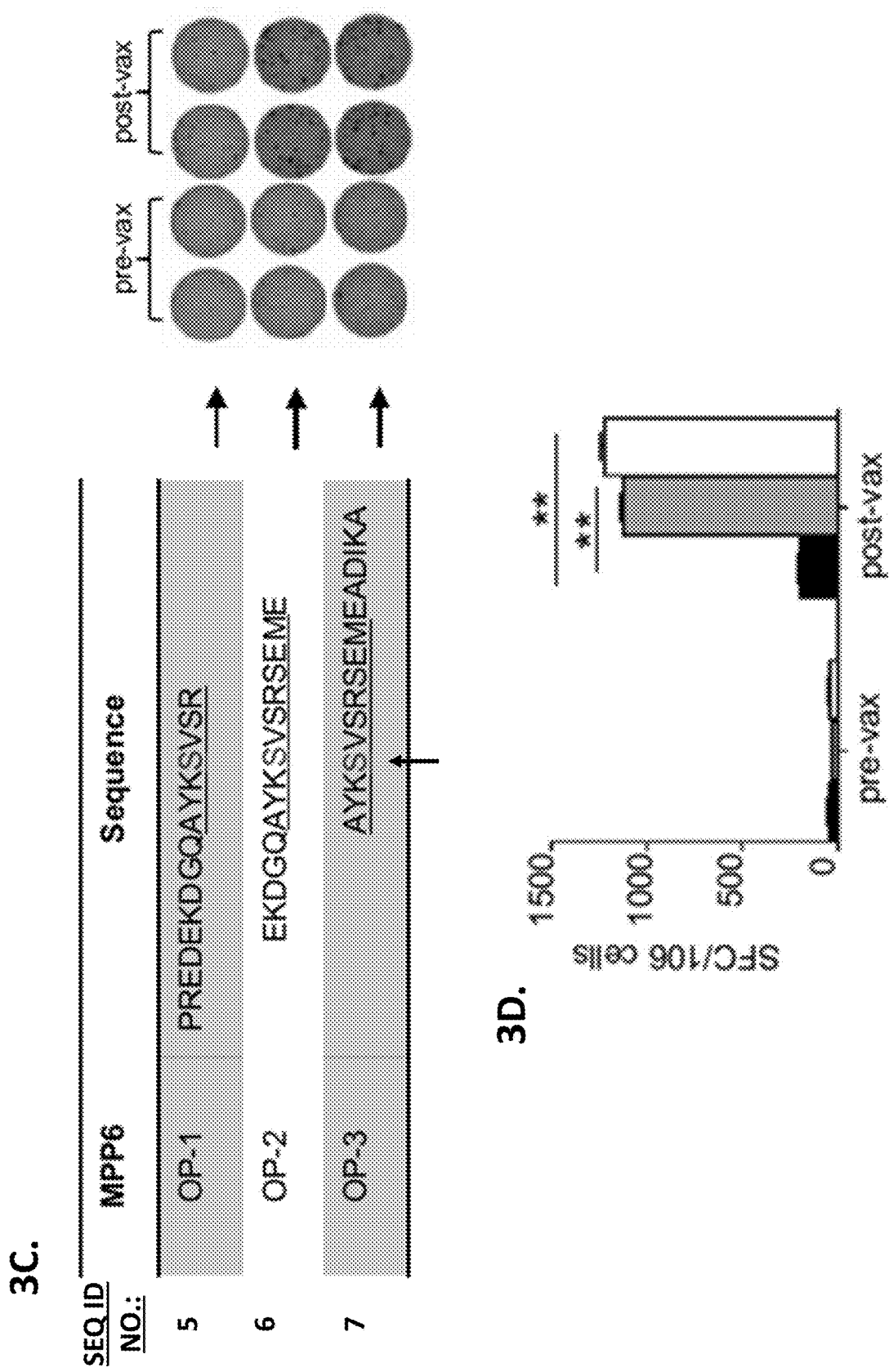
Figures 3E, 3F:
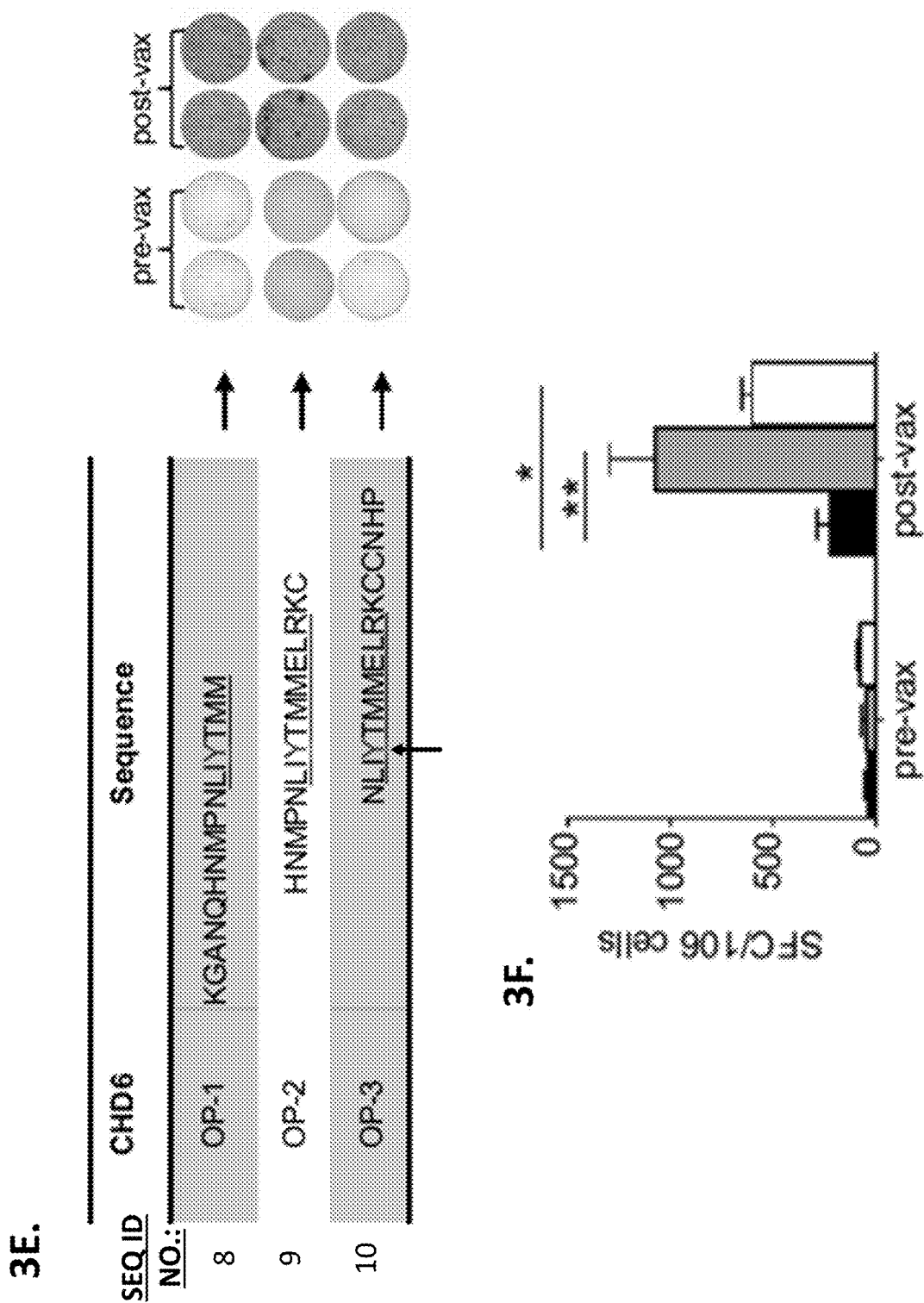
Figure 3G:
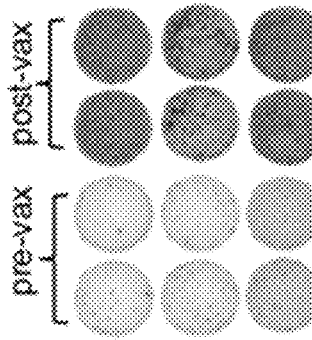
Figure 3H:
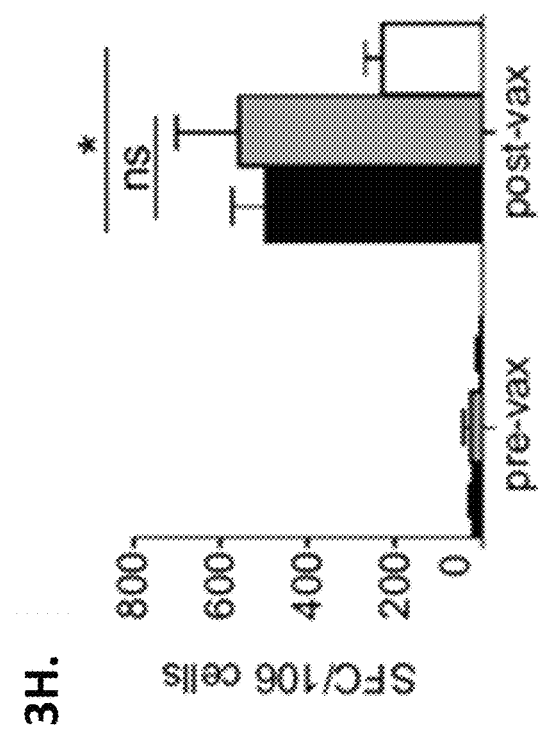
Figures 3I, 3J:
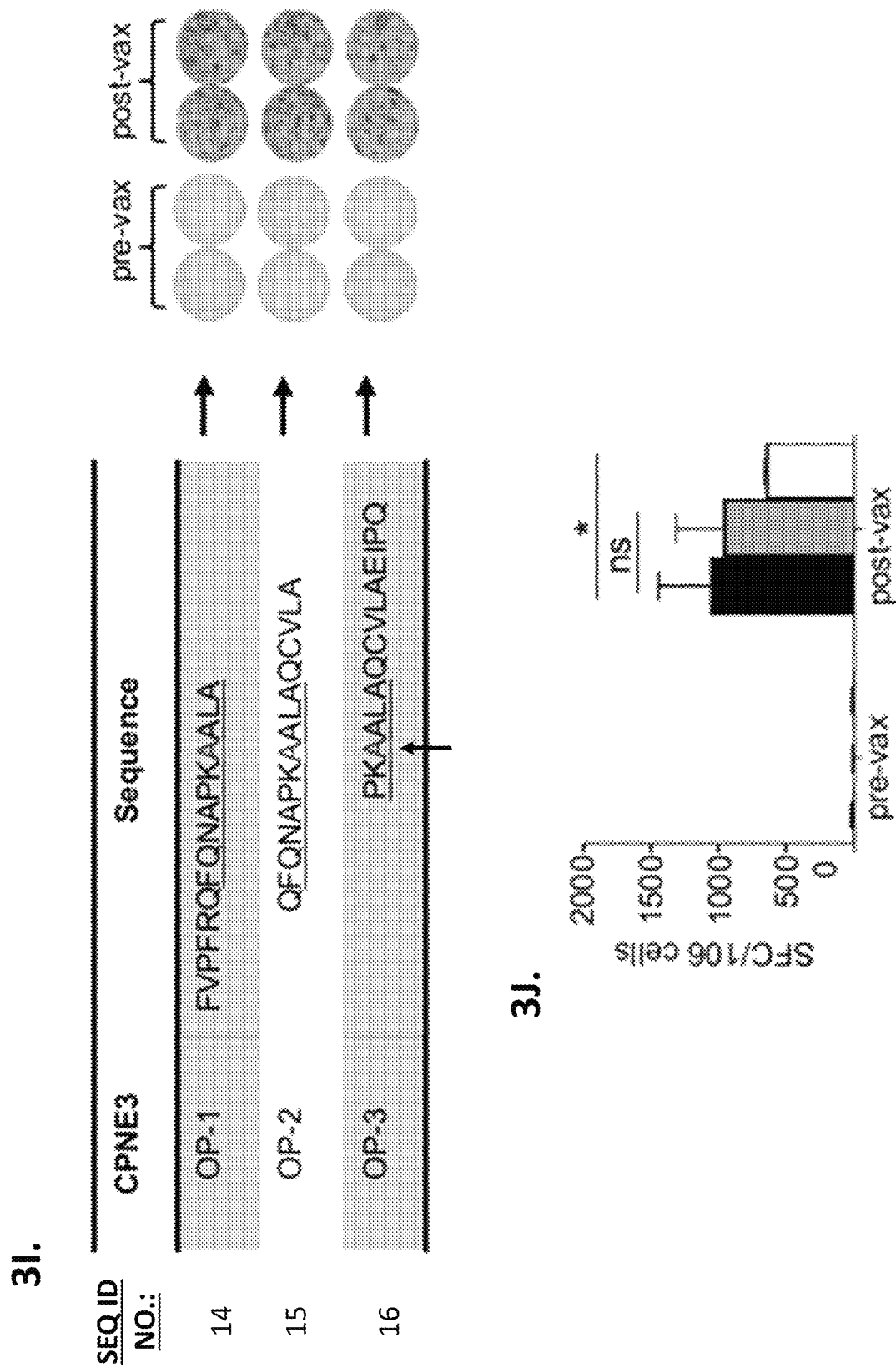
Figures 3K, 3L:
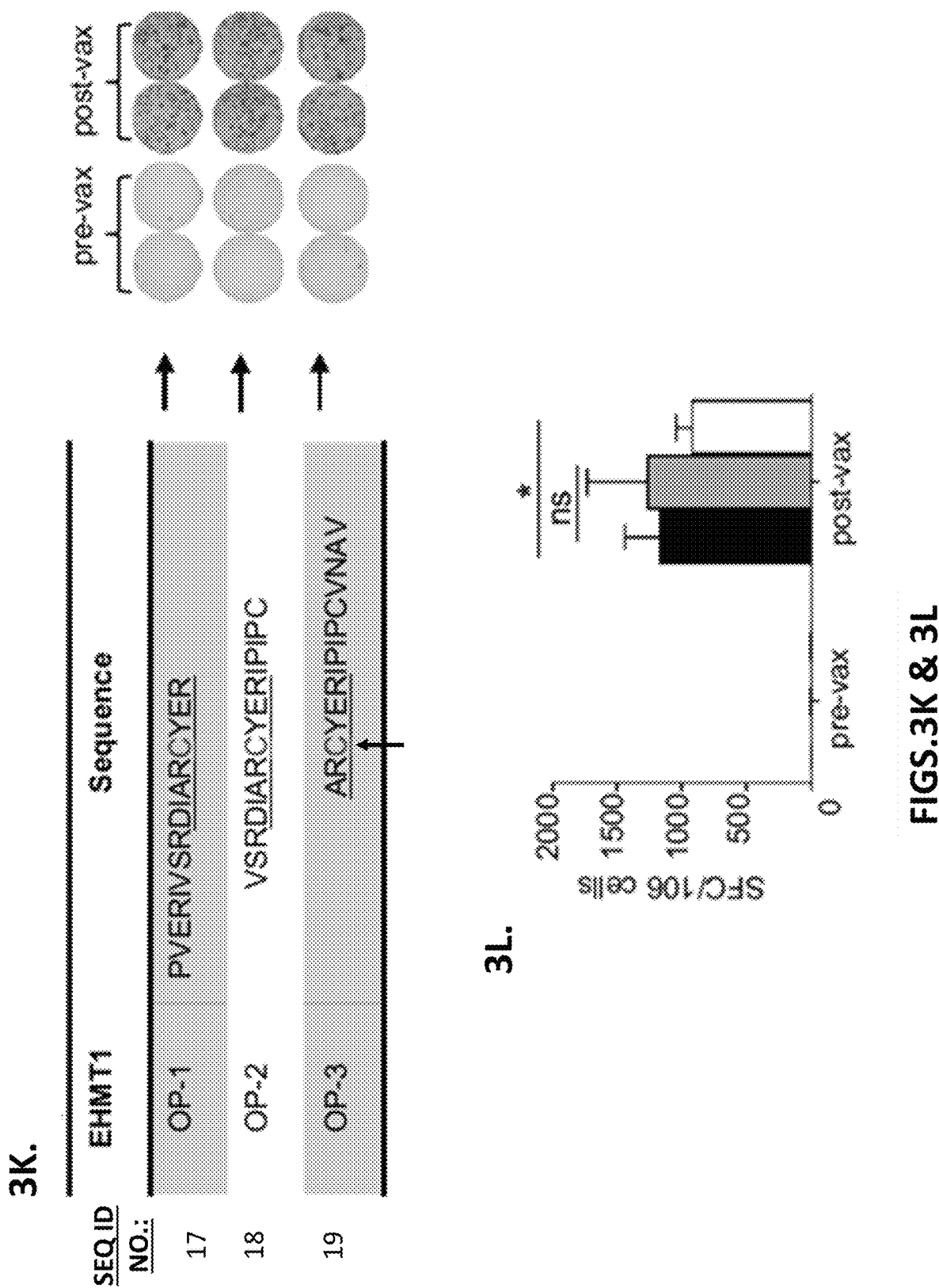
Figure 4A:
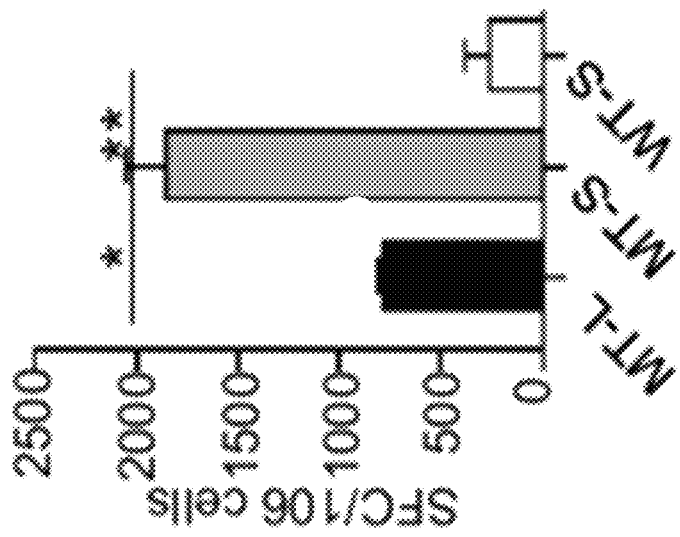
FIGS. 4A-4L are exemplary embodiments of neoantigens induced antigen-specific immune responses after in vitro stimulation of PBMCs collected from polyepitope DNA vaccinated triple negative breast cancer patients in accordance with the present disclosure. To confirm the specificity of the immune response induced by candidate neoantigens, T cell IFN-γ ELISPOT assays were performed on day 12 after 12-day stimulation with pooled mutant overlapping peptides by co-culturing stimulated PBMCs overnight with autologous, irradiated PBMCs pulsed with three pooled overlapping candidate peptides (represent one mutant gene, MT-L), individual mutant minimum (MT-S) peptide, individual wild type peptide (WT-S) and medium only or with non-related peptide as negative control. IFN-γ secretion and from representative patients BRC45 (FIGS. 4A & 4B for ZNF646, FIGS. 4C & 4D for MPP6), BRC78 (FIGS. 4E & 4F for CFTR, FIGS. 4G & 4H for CHD6), BRC18 (FIGS. 4I & 4J for EHMT1 and FIGS. 4K & 4L for CPNE3) against MT-L (black) peptide, MT-S (gray) peptide and WT-S (white) peptide are shown. The Negative controls in the ELISPOT assays included responder T cells cultured with no peptide (number of spot-forming cells per 106 cells was 30-150) or irrelevant peptide (number of spot-forming cells per 106 cells was 220-400). The background without peptide was subtracted from the experimental condition in each case. Data are presented as means±SEM (n=2-3 wells per peptide in ELISpot assay) and are representative of three independent experiments. Samples were compared using unpaired, two-tailed Student test (*, P<0.05; **, P<0.01; ns, no significant difference); SFC, spot-forming cells. All T-cell lines originated from 2 wk-post 3rd vax PBMCs; ELISPOT experiments were performed in duplicate or triplicate wells per condition.
Figure 4B:
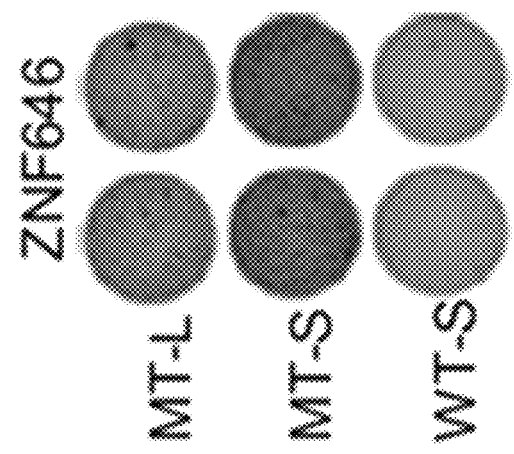
Figures 4C, 4D:
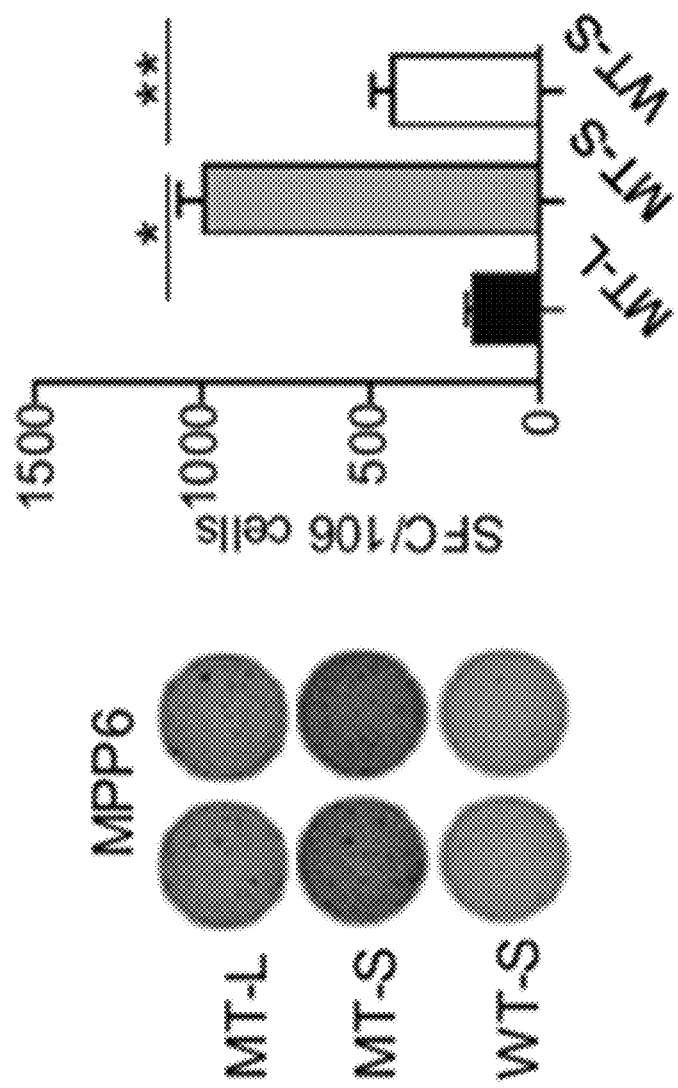
Figure 4E:
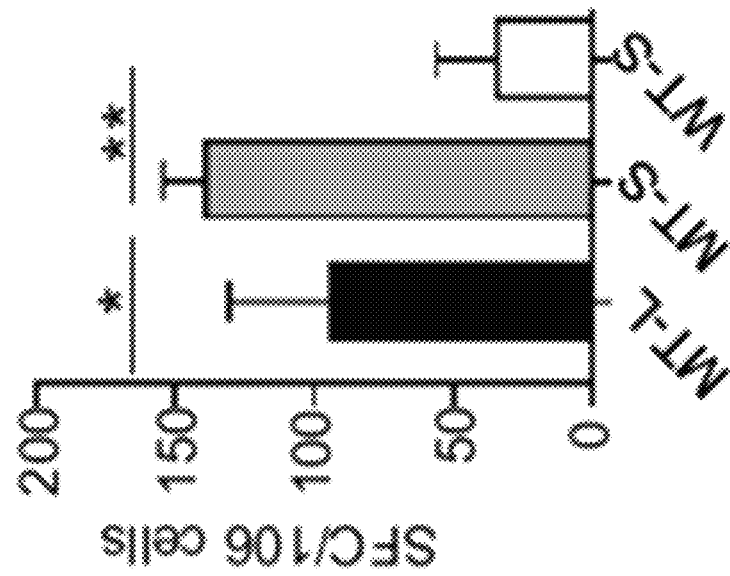
Figure 4F:
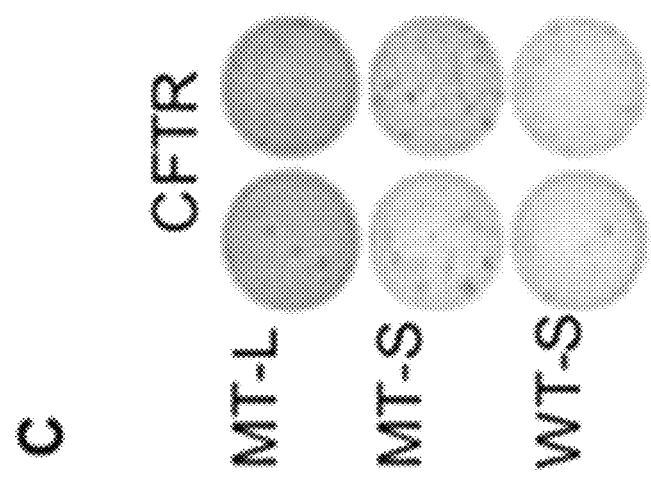
Figures 4G, 4H:
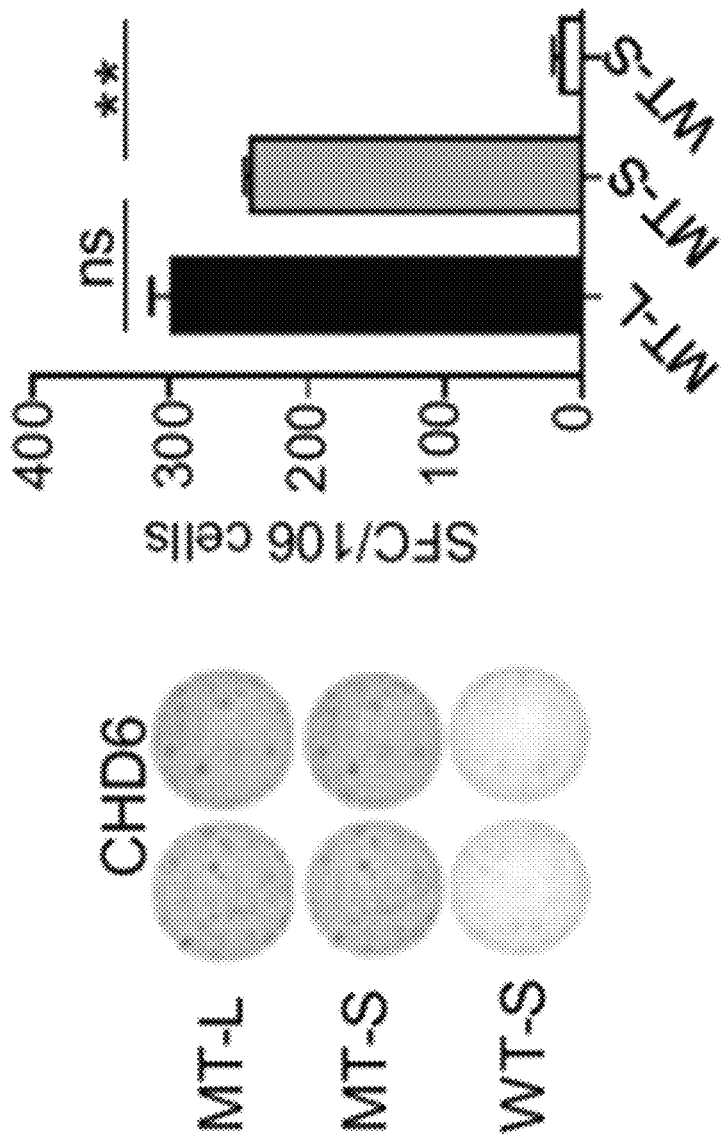
Figure 4I:
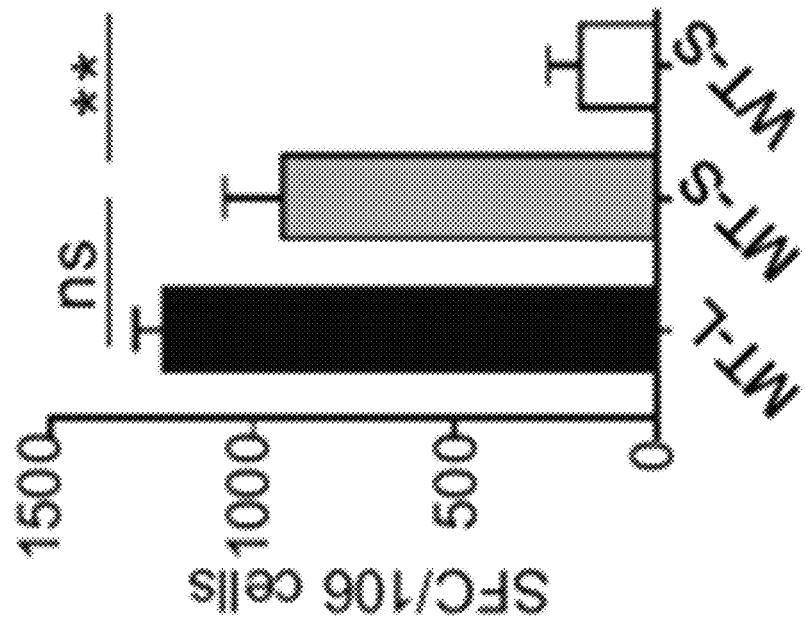
Figure 4J:
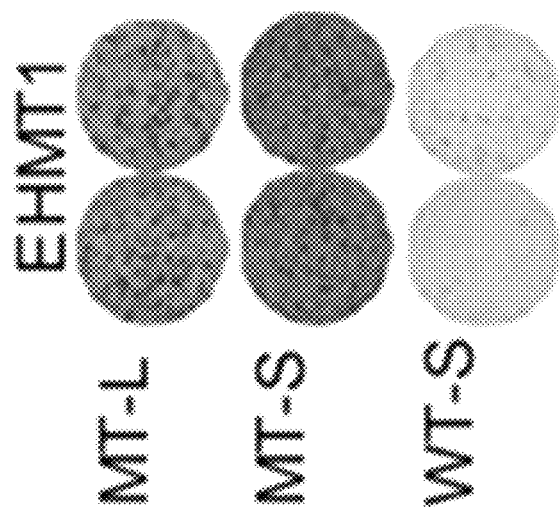
Figure 4K:
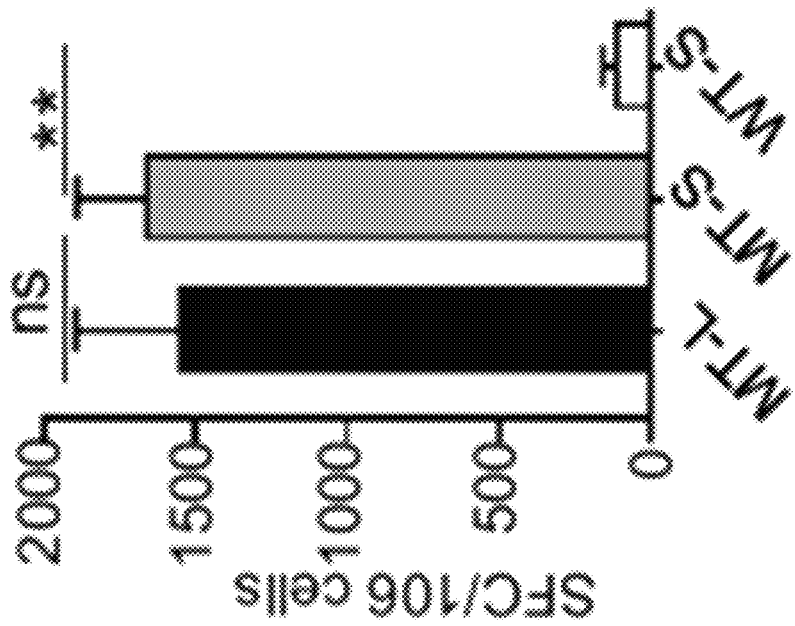
Figure 4L:
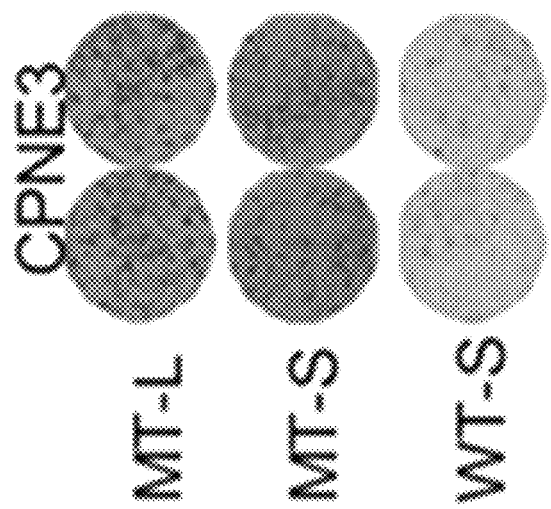
Figure 5A:
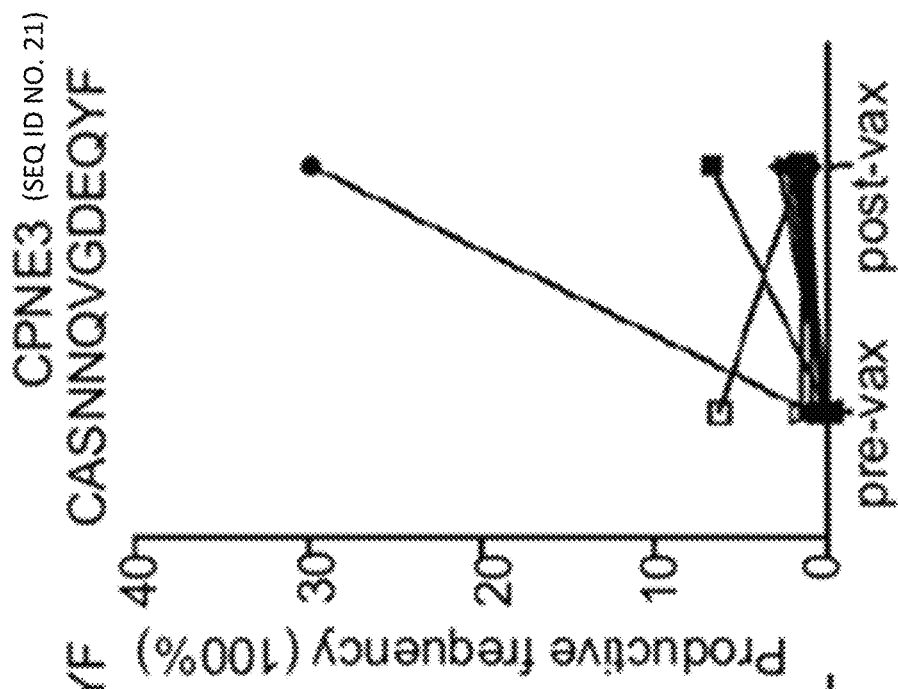
FIGS. 5A-5E are exemplary embodiments of vaccination promotion of a diverse neoantigen-specific T cell repertoire in accordance with the present disclosure. Summary of TCR-b clonotypes identified, using neoantigen-specific TCR-b CDR3 reference libraries in individual minimum stimulated PBMCs obtained before and after vaccination are shown. TCR-b CDR3 region was sequenced for patient BRC78 (FIG. 5A; SEQ ID NO. 20), BRC18 (FIG. 5B; SEQ ID NO. 21 and FIG. 5C; SEQ ID NO. 22), BRC19 (FIG. 5D; SEQ ID NO. 23) and BRC08 (FIG. 5E; SEQ ID NO. 24). Each symbol represents a unique TCR-b sequence and its frequency (%) in pre- and post-vaccine samples; P values are indicated (Wilcoxon signed-rank test).
Figure 5B:
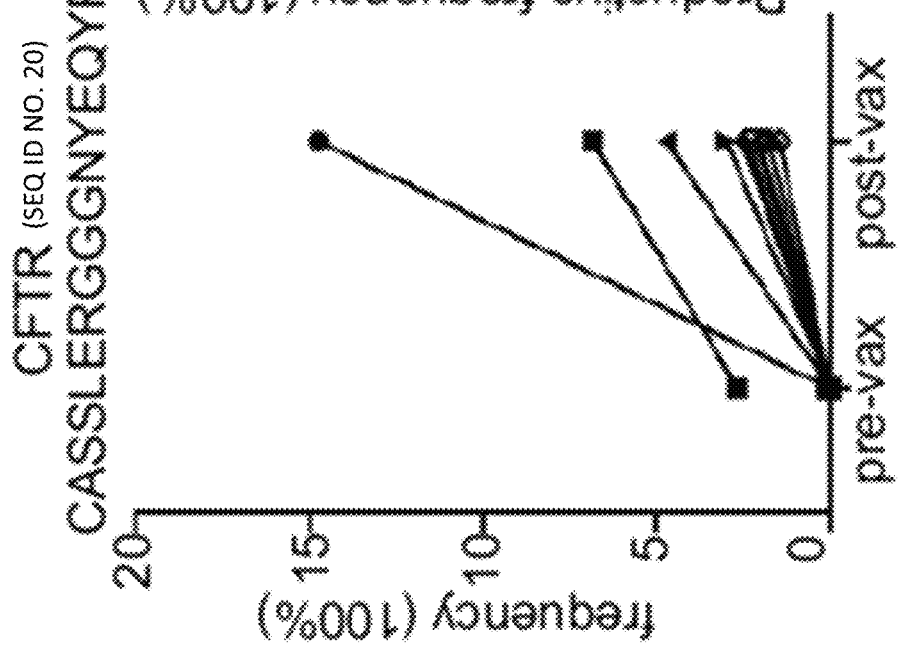
Figures 5C, 5D, 5E:
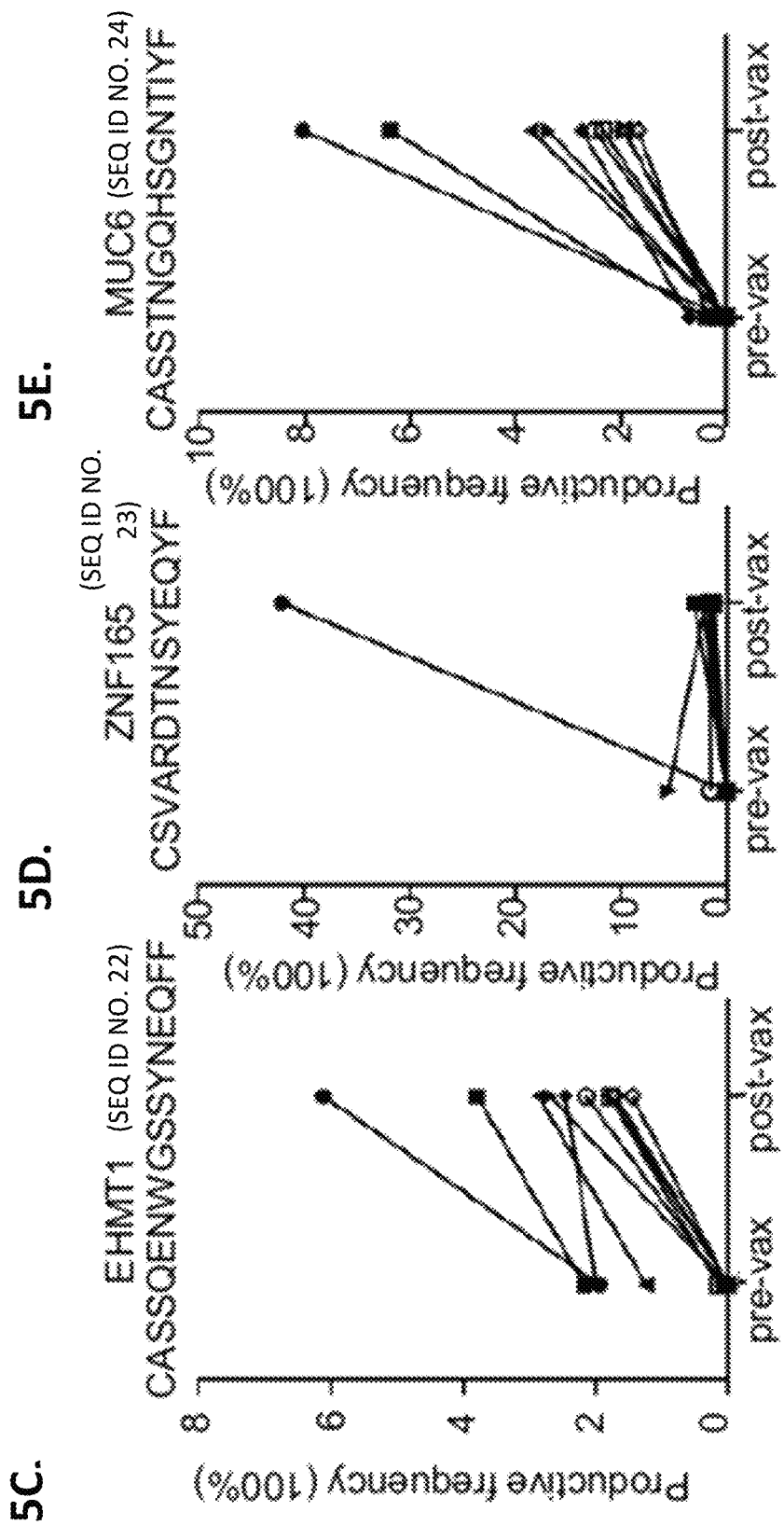

Neoantigen identification and vaccine design. Tumor biopsy (13 patients), surgery tissue (6 patients), and normal cells (PBMC) were subjected to DNA isolation followed by exome sequencing to identify somatic mutations resulting in altered protein/amino acid sequences. Tumor RNA sequencing (using cDNA capture) was used to assess expression of somatic mutations. The pVAC-Seq suite of software tools was used to prioritize candidate neoantigens for inclusion in the neoantigen DNA vaccines. Genetic alterations were prioritized by variant allele frequencies of both DNA and RNA, and predicted binding affinity of the mutant amino acid sequence. Rather than rely on a single prediction algorithm, pVAC-Seq incorporates multiple different prediction algorithms to assess binding, and outputs both a median and best score. Typically, mutant amino acid sequences with a predicted binding score of <500 nM were selected. For those candidates with a missense mutation in one of the HLA anchor positions, the fold change between mutant and wild type peptides was used to prioritize candidates with a fold change >1. The average number of neoantigens included in the neoantigen DNA vaccines was 11 (range 4-20, FIG. 2A, FIG. 2C). 97% of the neoantigens were the result of missense mutations, with the remaining neoantigens being the result of insertion/deletion or frameshift mutations (FIG. 2B). Mutations in TP53 were by far the most common, and neoantigens related to TP53 mutations were present in 14/18 subjects (78%), although the location of the TP53 mutations differed greatly among subjects (FIGS. 2B & 2C). Mutations in other genes that are commonly found in TNBC were much less frequently observed, such as SOX17, KMT2D, and PIK3R1 (<17%). It is noted that the data in FIG. 2B represent genetic alterations; not all genetic alterations were prioritized as neoantigens for inclusion in neoantigen DNA vaccines. No data are shown for patient BRC65, this patient did have a mutation in PIK3CA that was filtered out due to low coverage.

Figure 7:
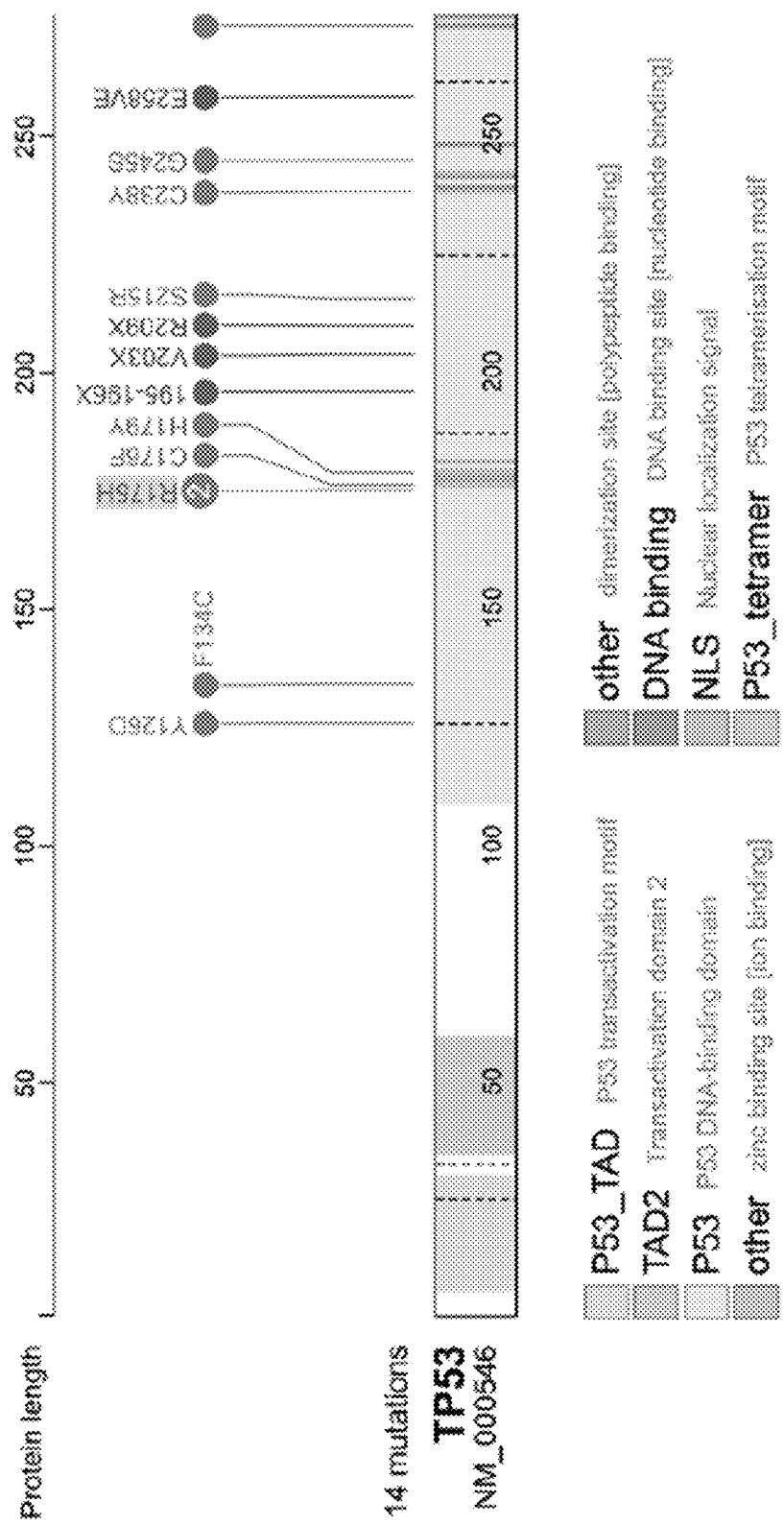
FIG. 7 is an exemplary embodiment of a TP53 lolliplot in accordance with the present disclosure. Mutations occurring within the TP53 gene, with the only recurrent mutation (R175H) indicated by a "2".
Figures 8A, 8B, 8C:
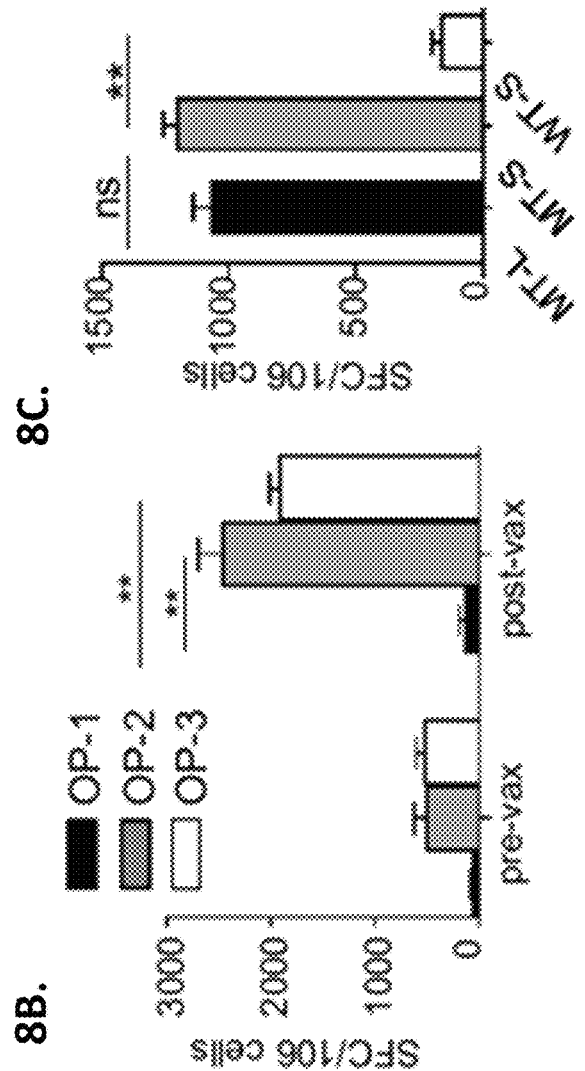
Figures 8J, 8K, 8L:
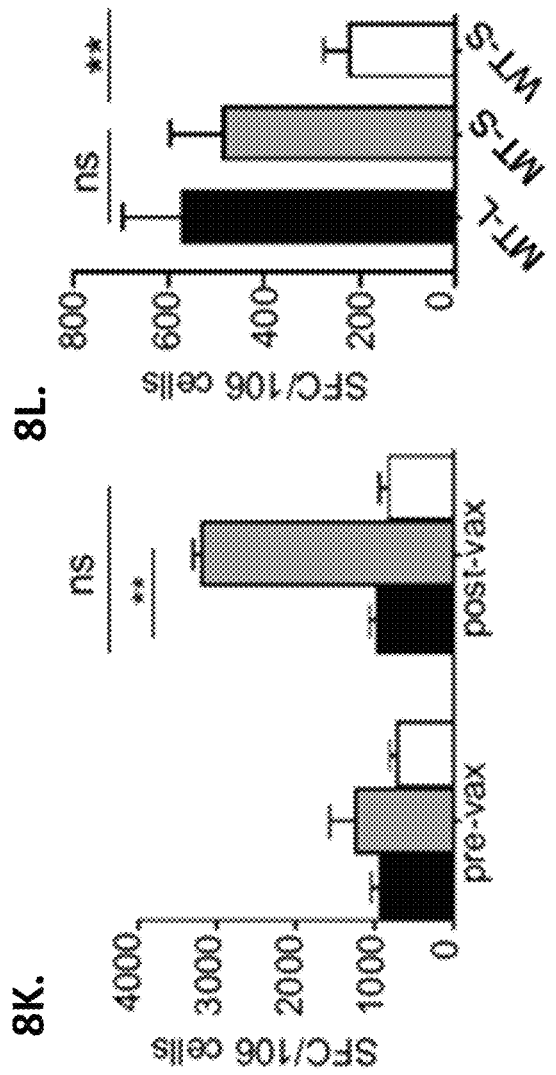
Figure 9A:
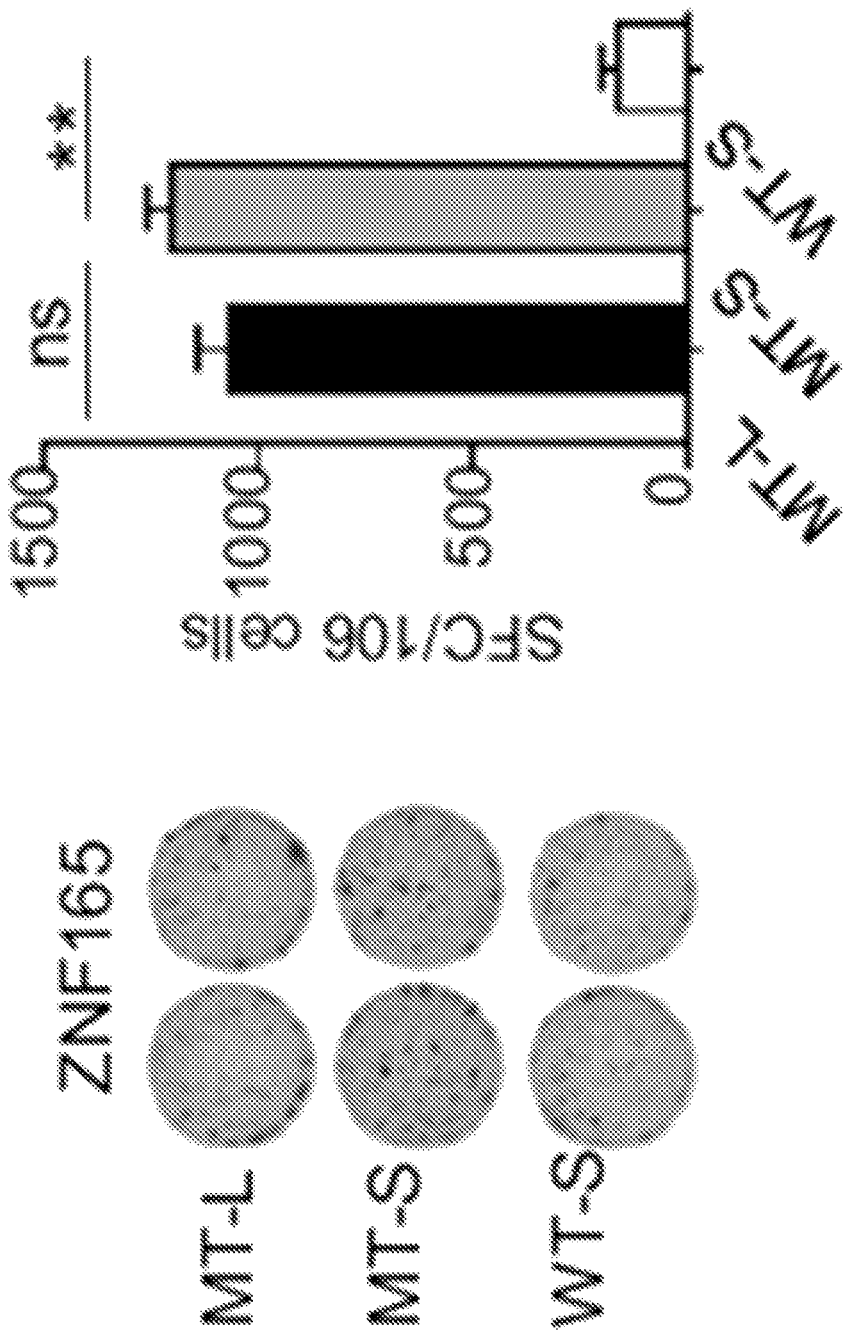
FIGS. 9A-9D are exemplary embodiments of neoantigens induced antigen-specific immune responses after in vitro stimulation of PBMCs collected from polyepitope DNA vaccinated triple negative breast cancer patients in accordance with the present disclosure. To confirm the specificity of the immune response induced by candidate neoantigens, T cell IFN-γ ELISPOT assays were performed on day 12 after 12-day stimulation with pooled mutant overlapping peptides by co-culturing stimulated PBMCs overnight with autologous, irradiated PBMCs pulsed with three pooled overlapping candidate peptides (represent one mutant gene, MT-L), individual mutant minimum (MT-S) peptide, individual wild type peptide (WT-S) and medium only or with non-related peptide as negative control. IFN-γ secretion from representative patients BRC19 (FIG. 9A for ZNF165, FIG. 9B for UBA7) and BRC08 (FIG. 9C for MUC6, FIG. 9D for C11orf52) against MT-L (black) peptide, MT-S (gray) peptide and WT-S (white) peptide are shown. The Negative controls in the ELISPOT assays included responder T cells cultured with no peptide (number of spot-forming cells per 106 cells was 30-150) or irrelevant peptide (number of spot-forming cells per 106 cells was 220-400). The background without peptide was subtracted from the experimental condition in each case. Data are presented as means±SEM (n=2-3 wells per peptide in ELISpot assay) and are representative of three independent experiments. Samples were compared using unpaired, two-tailed Student test (*, P<0.05; **, P<0.01; ns, no significant difference); SFC, spot-forming cells. All T-cell lines originated from 2 wk-post 3rd vax PBMCs; ELISPOT experiments were performed in duplicate or triplicate wells per condition.
Figure 9B:
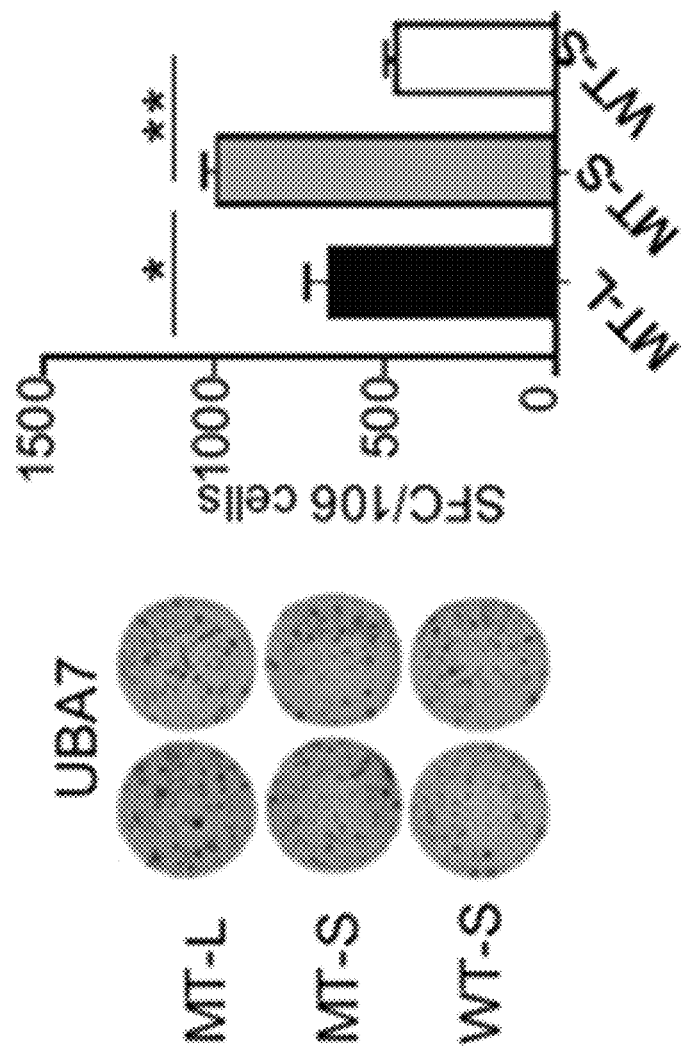
Figure 9C:
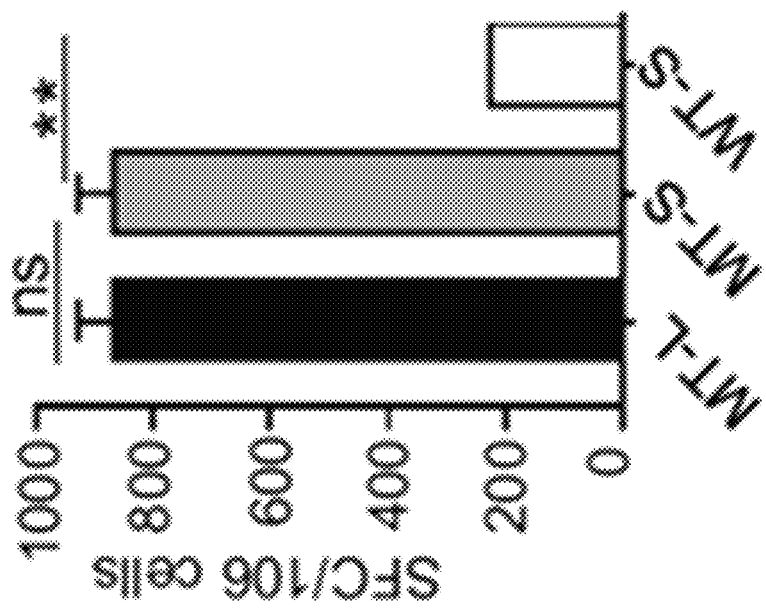
Figure 9C:
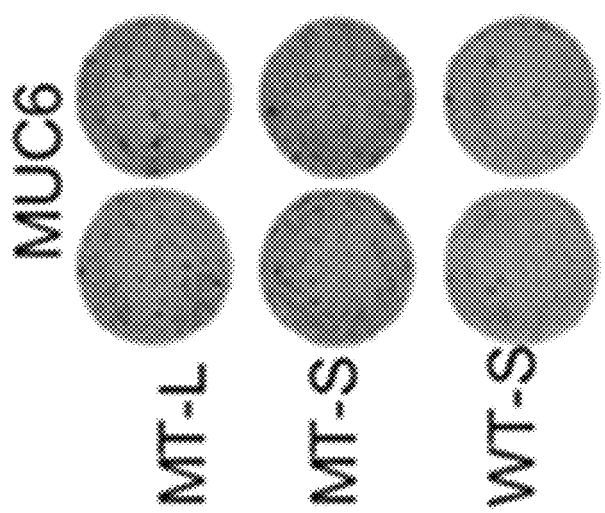
Figure 9D:
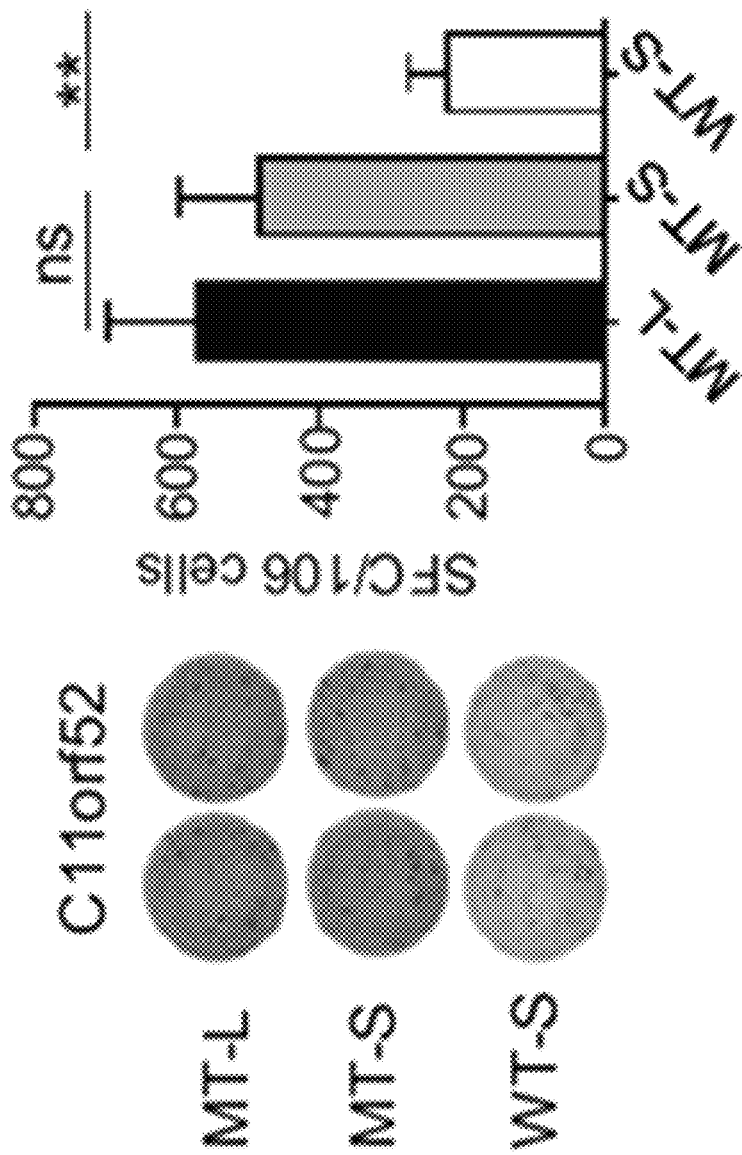

Induction of neoantigen-specific responses. Immune monitoring was performed in vaccinated patients using PBMC collected at baseline and post-vaccination (FIG. 1). Immune monitoring was performed in an unbiased manner by using overlapping peptides corresponding to each neoantigen included in the vaccine (typically peptides 15 to 16 amino acids in length overlapping by 11 amino acids). Neoantigen-specific responses were assessed after in vitro culture for 12 days with the overlapping peptides (OP), followed by IFN-γ ELISPOT assay. Baseline and post-vaccination PBMC were cultured for 12 days with OP, and tested against each individual OP (FIGS. 3A-3L) and FIG. 7). A significant increase in the number of spots following vaccination was considered evidence of a vaccine-induced neoantigen-specific response. Of note, reactivity was typically the highest against the OP that included the entire predicted MHC class I epitope, whereas OP incorporating only part of the predicted epitope were poorly recognized. To confirm the specificity of the neoantigen-specific response, the ELISPOT assays were repeated using short peptides corresponding to the predicted mutant and wildtype MEW class I epitopes. In the majority of cases, the short mutant peptides elicited equal or better reactivity than the OP, whereas the matching wild type peptide generally elicited little to no reactivity (FIGS. 4A-4L and FIGS. 8A-8L). In two patients, BRC16 and BRC80, no response was detected against any of the candidate neoantigens included in the neoantigen DNA vaccine (FIG. 2C).

Analysis of T cell receptor (TCR) usage showed a dramatic expansion of selected TCRβ clonotypes after vaccination and in vitro restimulation, consistent with the observed responses by ELISPOT. In some cases, e.g. EHMT1 and MUC6, multiple clones increased in frequency suggestive of an oligoclonal response, whereas in other cases, e.g. ZNF165 and CPNE3, the response appeared more monoclonal (FIGS. 5A-5E). The increase in TCRβ clonotypes after in vitro restimulation was in agreement with intracellular IFN-γ production after stimulation with long overlapping peptides (FIGS. 9A-9D). Interestingly, analysis of CD4 T cell responses suggested neoantigen-specific CD4 T cells were induced alongside neoantigen-specific CD8 T cells.

Figure 6:
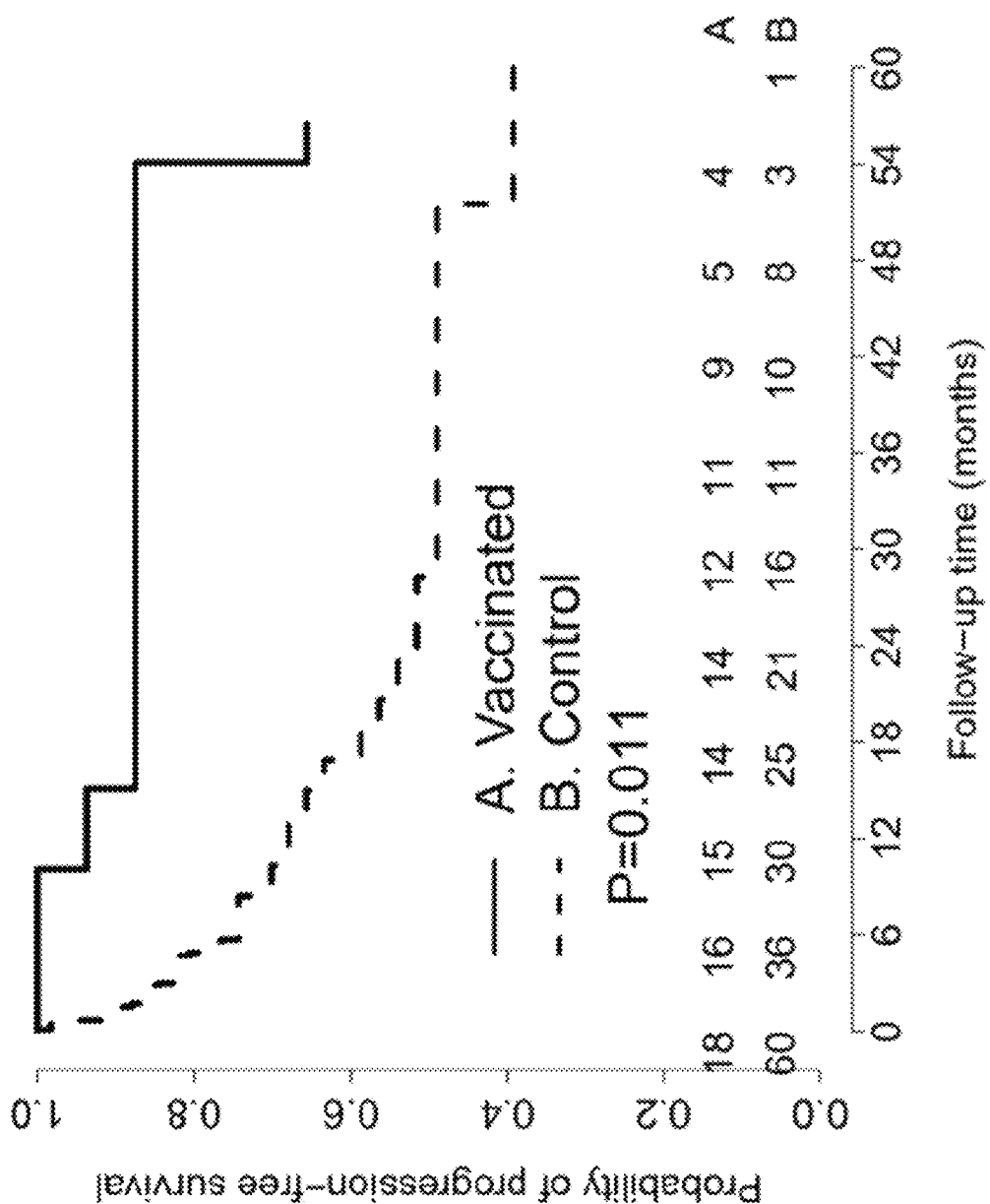
FIG. 6 is an exemplary embodiment of survival cure of patients who received poly-epitope DNA vaccine comparing with general TNBC patients without vaccine in accordance with the present disclosure. Kaplan-Meier Survival Curve of patient progression, free survival of vaccinated cohort compared to historical controls, showed that the vaccine can significantly extend vaccinated patients survival period (p<0.05).

Preliminary evidence of clinical responses after neoantigen DNA vaccination. While strictly not powered to assess clinical responses, vaccination significantly improved progression-free survival (PFS) compared to historical institutional controls of TNBC patients seen at the Washington University Breast Clinic between 2006 and 2010 (FIG. 6). In this previously published series, encompassing 290 patients, 60 patients were selected for control based on Stage II/III disease, and survival greater than 4 months after surgery to match the vaccine cohort. After 36 months follow-up, PFS was 89% (16/18) in vaccinated patients (p=0.033).

Discussion

The embodiments disclosed herein describe preclinical studies and early phase clinical trials establishing the DNA vaccine platform as a safe, flexible and robust vaccine platform. Besides being safe, other advantages of the DNA vaccine platform include low cost, relative ease of manufacture compared to other vaccine platforms, and molecular flexibility which allows genetic manipulations to the antigen and/or to improve vaccine efficacy. Preclinical studies performed to optimize the neoantigen DNA vaccine platform were recently reported, in which it was demonstrated that polyepitope neoantigen constructs expressing multiple long (>20-mer) neoantigen epitopes fused with a mutant form of ubiquitin are able to induce antitumor immune responses in preclinical breast cancer models, as described in Li et al., Genome Med. 13, 56 (2021), which is herein incorporated by reference in its entirety. Disclosed herein is the first phase 1 clinical trial which leverages the optimized neoantigen DNA vaccine platform.

Embodiments of the present disclosure include the first DNA neoantigen vaccine trial conducted for TNBC and demonstrates the feasibility and potential of personalized vaccine therapy aided by in silico prediction. Prior studies have focused on high mutational burden cancers such as melanoma, non-small cell lung cancer, and bladder cancer. The trial described herein is unique in using personalized neoantigen vaccines in a cancer with relatively low tumor mutation burden. Despite this, a minimum of 4 (and up to 20) neoantigens were successfully identified for each patient and produced durable neoantigen-specific immune responses in the majority of patients in the trial. This has produced improved 5 year survival among the cohort compared to institutional historical controls.

There is currently an unmet clinical need for effective treatment, and particularly adjuvant treatment, for TNBC. TNBC is associated with a more aggressive course and has a higher chance of recurrence after surgery. However, there is a paucity of systemic therapies available due to its insensitivity to hormonal therapy and targeted agents. Administration of the vaccine in the adjuvant setting also gives us the opportunity to utilize surgical specimens for sequencing and neoantigen identification. Patient's recovery from surgery gives us time to manufacture the personalized vaccine. Thus, use of personalized DNA neoantigen vaccine in the adjuvant setting not only fulfills a clinical need, but is also technically practical.

The in silico neoantigen prediction algorithm pVAC-Seq used in the trial disclosed herein is a state of the art algorithm using next-generation sequencing data. The recent Tumor Neoantigen Selection Alliance (TESLA), through comparison of 25 prediction algorithms, identified factors such as MHC binding affinity, half-life, neoantigen expression level, and level of foreignness as important predictors of neoantigen immunogenicity. pVAC-Seq's algorithm incorporates many of the key favors identified by the TESLA consortium.

First, variant calling is performed using NetMHC 3.4, where DNA sequences of tumor tissue and a normal specimen are aligned and compared to identify foreignness. Data from variant calling is imputed into pVAC-Seq which then performs three main functions: 1) epitope prediction, 2) integrating sequence-based information, and 3) filtering neoantigen candidates. The epitope prediction phase is primarily driven by MHC-binding affinity. RNA-seq data is then used to determine expression levels of predicted epitopes in integration phase, and those with low frequencies are filtered out. In summary, the predicted neoantigens using pVAC-Seq take into account foreignness, expression level, and MHC binding affinity, reflecting the consensus reached by TESLA. A potential shortcoming of pVAC-Seq is the emphasis on MHC class I binding given the importance of CD4 cells in reprogramming of the tumor microenvironment and promoting antitumor immunity. Furthermore, many tumors have undergone MHC class I loss, but may still be susceptible to CD4 T cell-mediated immunity. Although the neoantigen prediction and prioritization focused on the binding affinity to MHC class I in a previous study, neoantigens-specific CD4 T cell responses were detected in some patients. Long neoantigen peptides (20-30 amino acids) expressed by the DNA vaccine may not only be preferentially processed and presented by antigen presenting cells, but also have the advantage of being able to bind both MHC class I and II molecules, and therefore are capable of activating CD8 and/or CD4 T cells. There is evidence that CD4 T cells can help CD8 T cell priming by licensing cDC1 via the CD40/CD40L interaction, and can help prevent CD8 T exhaustion. CD4 T cells also have effector roles in the tumor microenvironment including direct cytotoxicity, cytokine secretion, and NK cell activation. With recent improved understanding of MHC class II epitopes, future algorithms may utilize this untapped resource and generate even more effective vaccines.

Some embodiments disclosed herein focused on TNBC patients who had residual disease following neoadjuvant chemotherapy, a group with significantly worse survival compared to non-TNBCs. The 18 vaccine recipients had 2 deaths in the 3 year follow up, demonstrating superior survival after surgery compared to the institutional historical control of TNBC patients seen at the Washington University Breast Clinic between 2006 and 2010. In this previously published series, 87 patients had residual disease after neoadjuvant chemotherapy with survival greater than 4 months. The cohort of patients who had received personalized DNA neoantigen vaccines had a 3-year survival of 89% compared to 79% in the control. The significantly improved survival of the cohort of the present disclosure compared to a recent historical cohort treated at the same institution provides strong support for further phase clinical testing of the vaccine embodiments disclosed herein.

With recent insights into the biology of immune checkpoints and the tumor microenvironment, and in order to reach full therapeutic potential, cancer vaccines will need to be combined with other immune therapies, including chemotherapy, radiation therapy, and immune checkpoint inhibition (ICI). A preclinical model demonstrated that anti-PD-L1 treatment is able to augment the antitumor immunity mediated by DNA vaccine-induced neoantigen-specific immune responses, and provides support for testing polyepitope neoantigen DNA vaccines in TNBC+/−anti-PD-L1 antibody Durvalumab (NCT03199040). A phase II clinical trial (NCT03606967) is investigating how well nab-paclitaxel, durvalumab, and tremelimumab (anti-CTLA-4)+/− neoantigen SLP vaccine works in treating patients with metastatic TNBC.

The primary goal of the embodiments disclosed herein tested the safety of polyepitope neoantigen DNA vaccines. The DNA vaccines described herein have been demonstrated as safe and well-tolerated with mostly grade 1 and 2 adverse events. The vaccines were able to elicit neoantigen-specific immune responses in TNBC patients, which are associated with an improved progression free survival. As described herein, these results positively support ongoing and future efforts to integrate the neoantigen vaccines into existing cancer treatment paradigms.

Example B

Optimized Polyepitope Neoantigen DNA Vaccines Elicit Neoantigen-Specific Immune Responses in Preclinical Models and in Clinical Translation.

Preclinical studies and early clinical trials have shown that targeting cancer neoantigens is a promising approach towards the development of personalized cancer immunotherapies. DNA vaccines can be rapidly and efficiently manufactured and can integrate multiple neoantigens simultaneously. At least one aim of the present disclosure was to optimize the design of polyepitope DNA vaccines and test optimized polyepitope neoantigen DNA vaccines in preclinical models and in clinical translation. A DNA vaccine platform was developed and optimized to target multiple neoantigens. The polyepitope DNA vaccine platform was first optimized using model antigens in vitro and in vivo. Neoantigens were then identified in preclinical breast cancer models through genome sequencing and in silico neoantigen prediction pipelines. Optimized polyepitope neoantigen DNA vaccines specific for the murine breast tumor E0771 and 4T1 were designed and their immunogenicity was tested in vivo. An optimized polyepitope neoantigen DNA vaccine was also tested in a patient with metastatic pancreatic neuroendocrine tumor. Embodiments described herein support an optimized polyepitope neoantigen DNA vaccine design encoding long (≥20-mer) epitopes with a mutant form of ubiquitin ($Ub^{mut}$) fused to the N-terminus for antigen processing and presentation. Optimized polyepitope neoantigen DNA vaccines were immunogenic and generated robust neoantigen-specific immune responses in mice. The magnitude of immune responses generated by optimized polyepitope neoantigen DNA vaccines was similar to that of synthetic long peptide vaccines specific for the same neoantigens. When combined with immune checkpoint blockade therapy, optimized polyepitope neoantigen DNA vaccines were capable of inducing antitumor immunity in preclinical models. Immune monitoring data suggest that optimized polyepitope neoantigen DNA vaccines are capable of inducing neoantigen-specific T cell responses in a patient with metastatic pancreatic neuroendocrine tumor. As disclosed herein, a novel polyepitope neoantigen DNA vaccine platform was developed and optimized that can target multiple neoantigens and induce antitumor immune responses in preclinical models and neoantigen-specific responses in clinical translation.

Background Cancer neoantigens are created by somatic DNA alterations resulting in protein sequence changes capable of triggering adaptive immune responses. Next generation sequencing, together with bioinformatics-based computational algorithms, has revolutionized the ability to identify cancer neoantigens. It has been demonstrated that cancer neoantigens are important targets during cancer immunoediting and that cancer sequencing combined with epitope prediction algorithms can be used to identify and prioritize neoantigens for integration into personalized cancer vaccines. Conceptual advantages associated with cancer vaccines targeting cancer neoantigens include the fact that neoantigens are not found in normal tissues, decreasing the risk of autoimmunity and/or central immune tolerance.

According to exemplary embodiments of the present disclosure, neoantigen vaccines based on the synthetic long peptide (SLP), RNA, and dendritic cell (DC) platforms are capable of inducing neoantigen-specific T cell responses, and support favorable clinical outcomes. In order to maximize antitumor immunity and to prevent or curtail tumor immune escape, targeting multiple neoantigens simultaneously is desirable. However, manufacturing neoantigen vaccines based on the SLP, RNA, or DC vaccine platforms under good manufacturing practice (GMP) conditions is both time consuming and resource-intensive. In comparison, one of the strengths of the recombinant DNA vaccine platform is the relative ease of manufacture of plasmid DNA on a scale appropriate for personalized vaccines. As such, the recombinant DNA vaccine platform represents an attractive platform for the clinical development of polyepitope neoantigen cancer vaccines.

Advantages of the DNA vaccine platform include its remarkable safety profile, the relative ease of manufacture, and the molecular flexibility that allows integration of multiple neoantigens using a single polyepitope construct.

Recent advances in the DNA vaccine platform, such as gene/vector optimization, molecular/formulation adjuvants, and DNA delivery by electroporation, have significantly improved the efficacy of DNA vaccines, and numerous early phase clinical trials are ongoing in the infectious disease and cancer fields. Efforts to optimize the polyepitope neoantigen DNA vaccine in preclinical models to maximize neoantigen presentation and vaccine immunogenicity are reported herein. According to the present disclosure, at least the following questions were addressed: (1) are longer epitopes (≥20-mers) processed equally well as minimal epitopes (e.g., 9-mers); (2) will short flanking sequences (spacers) between epitopes enhance antigen processing and reduce creation of junctional epitopes; and (3) will the addition of a mutant form of ubiquitin enhance neoantigen processing and presentation? As demonstrated herein, polyepitope inserts encoding 20-25-mer neoantigen epitopes (with or without spacers) fused with a mutant form of ubiquitin are efficiently processed and presented. Model DNA vaccines designed with this strategy were able to induce immune responses in vivo, and neoantigen DNA vaccines were able to induce antitumor immune responses in preclinical breast cancer models and neoantigen-specific T cell responses in clinical translation.

Methods

Animals. Female C57BL/6J (H-$2^b$) and Balb/cJ (H-$2^d$) mice were purchased from the Jackson Laboratory (Bar Harbor, ME). HHD II transgenic mice were originally obtained from Dr. F. Lemonnier (Institut Pasteur, Paris, France) and were maintained in SPF animal facilities. These mice express the transgene Tg (HLA-A/H2-D/B2M) 1Bpe in a mixed background involving B2M$^{tm1Unc/tm1Unc}$ and H2-D1$^{tm1Bpe/tm1Bpe}$. They express chimeric MHC-I heavy chain with HLA-A*0201 (α1-α2) and H-$2D^b$ (α3-transmembrane and intracytoplasmic domains), allowing the study of HLA-A2-restricted responses in vivo. All animals were used at 7-10 weeks of age. Protocols were approved by the Animal Studies Committee of Washington University School of Medicine (WUSM) and were in accordance with IACUC guidelines and procedures.

Tumors and cell lines. HeLa cells that stably express HLA-A2 (HeLa-A2), murine and human TAP-deficient RMA-S(H-$2^b$) and T2 cells made to express mouse MHC class I molecules were obtained from Dr. T. Hansen (Washington University School of Medicine). E0771 and 4T1.2 are mouse breast cancer cell lines of C57BL/6 (H-$2^b$) and Balb/c (H-$2^d$) origin, respectively. All cells were cultured in RPMI-1640 complete media (Gibco) supplemented with L-glutamine, 10% fetal bovine serum (Atlanta Biologicals, Flowery Branch, GA), sodium pyruvate, non-essential amino acids, and penicillin-streptomycin (Gibco).

Genome sequencing and neoantigen identification. Genomic DNA and RNA were extracted from E0771 and 4T1.2 tumors grown in vivo using commercially available kits (Qiagen). Tails from C57BL/6 and Balb/c mice were used as normal control. Exome and cDNA-capture sequencing were performed as previously described. The pVACseq pipeline, version 1.0.0-beta, was applied to identify genetic alterations and prioritize neoantigens based on the tumor/normal sequencing data. Briefly, each genetic alteration resulting in an amino acid change was evaluated in the context of 10-14 flanking amino acids. All sub-peptides containing the substitution were evaluated using the suite of IEDB-provided HLA class I peptide-binding algorithms (netMHC, NetMHCcons, netMHCpan, PickPocket, SMM, and SMMPMBEC). In order to prioritize neoantigen candidates, results with median predicted binding affinities ($IC_{50}$) less than 500 nm were filtered based on sample purity (both tumor VAF and RNA VAF >30%), gene expression level (FPKM>1), and ranked according to the fold change (MT/WT) of IC50 scores. Neoantigens with MT/WT fold change greater than 2 were incorporated in the polyepitope neoantigen DNA vaccines.

Polyepitope DNA and SLP vaccines. Codon-optimized DNA fragment encoding polyepitope neoantigens were synthesized by Blue Heron Biotech (Bothell, WA) or GenScript (Piscataway, NJ) and subsequently cloned into the mammalian expression plasmid pcDNA 3.1$^{(+)}$ (Invitrogen, Carlsbad, CA) or the pMSV.IR-ES.GFP (pMIG) retroviral expression vector. The sequences of the polyepitope constructs can be found in the Sequence Listing (SEQ ID NOs. 37-46) and are shown herein below.

Where indicated, DNA sequence for Ub$^{mut}$, a mutated (G76V) ubiquitin, was fused to the N-terminus of the polyepitope construct by standard molecular subcloning. Plasmid DNA were amplified in *Escherichia coli* DH5α (Invitrogen) and purified using NucleoBond Maxi Plasmid DNA Purification kits (Macherey-Nagel, Bethlehem, PA). DNA vaccination was performed using a Helios gene gun (Bio-Rad, Hercules, CA) as previously described. Typically, 4 μg of DNA was delivered to non-overlapping shaved and depilated mice abdominal areas at 3-day intervals (days 0, 3, and 6) for a total of three doses. The discharge helium pressure was set to 400 p.s.i. Immune responses were measured 5 days after the last gene gun vaccination (day 11).

SLPs containing the identified neoantigens were custom-made by GenScript and Peptide 2.0 (Chantilly, VA). Lyophilized peptides were first dissolved in $H_2O$ or DMSO and stored at −20° C. One hundred micrograms of each peptide was diluted in PBS and mixed with 50 μg of poly(I:C) (InvivoGen) before subcutaneous injection on day 0 and day 7. Immune responses were measured by ELISpot assay on day 12.

Polyepitope DNA vaccine sequences. Listed below are the DNA sequences (DNA (5'→3')) and translated amino acid sequences (AA (N→C terminus)) of Ub$^{mut}$ and polyepitope vaccine constructs. Of note, when Ub$^{mut}$ was subsequently cloned in front of the polyepitope constructs, the start codon (ATG) and the encoded methionine (M) were removed from each construct, respectively.

For the DNA constructs that encode HLA-A2 epitopes, only P20 containing a C-terminus HA tag (YPYDVPDAY) is listed. Sequences for the related constructs M20, P9, and M9 with or without the AAY spacer are available upon request. DNA constructs were cloned into pMSV.IRES.GFP (in vitro studies) or pcDNA3.1$^{(+)}$ (in vivo studies) under the control of a CMV promoter. Personalized DNA vaccine construct for the cancer patient GTB16 was cloned into pING vector (1). In 4T1.2 polyepitope DNA vaccine, sequence encoding a murine CMV pM84 peptide which contains the H-2K$^d$-restricted epitope AYAGLFTPL (2) was included as a built-in positive control. (Note: * denotes the translational stop.)

Ub$^{mut}$ (G76V)
DNA (5'→3') (SEQ ID NO. 37)
atgcagatctttgtgaaaaccttaactggtaagaccatcaccctggaggtcgagcccagtgacaccattgagaatgtc -continued aaggcaaagatccaggacaaggaggggcatccccctgaccagcagaggctgatctttgcaggcaagcagctggaagatggccgcaccc
tgtcagactacaacatccagaaagagtccaccctgcacctggtccttcgcctcagaggtgtc AA (N→C terminus) (SEQ ID NO. 38)
MQIFVKTLTGKTITLEVEPSDTIENVKAKIQDKEGIPPDQQRLIFAGKQLED
GRTLSDYNIQKESTLHLVLRLRGV P20-HA polyepitope vaccine
DNA (5'→3') (SEQ ID NO. 39)
ggcatcctggccagaaacctggtgcccatggtggccaccgtgcagggccagaacctgaagggccccgtgttcatg
tgcctgggcggcctgctgaccatggtggccggcgccgtgtggctggtgctgtgctgctacgtgctggaggagaccagcgtgatgctggcc
aagagacccctgatcgtggtgacccacacctacctggagcccggccccgtgaccgcccaggtggtgctgcaggccgccatccagaacg
ccggcctgtgcaccctggtggccatgctgctggaggagaccatcttcagcagcgccttcaccatcaccgaccaggtgcccttcagcgtgca
gctgagagccctggacgcctgggacttcggcagcgtgggcggcgtgttcaccagcgtgggcaaggccgtgcaccagagcccctgacc
ggcggcatcctgggcttcgtgttcacccctgaccgtgcccagcgagagacaattgtacccatacgatgttccagattacgcttag AA (N→C terminus) (SEQ ID NO. 40)
GILARNLVPMVATVQGQNLKGPVFMCLGGLLTMVAGAVWLVLCCYVL
EETSVMLAKRPLIVVTHTYLEPGPVTAQVVLQAAIQNAGLCTLVAMLLEETIFSSAFTIT
DQVPFSVQLRALDAWDFGSVGGVFTSVGKAVHQSPLTGGILGFVFTLTVPSER
QLYPYDVPDYA*

E0771 polyepitope vaccine
DNA (5'→3') (SEQ ID NO. 41)
atgcagctggcctctacctacacagcttacatcgtgggctacgtgcactacggagattggctgaagaacgagaagat
caacagggtggtgttcgtgtggaacttctgcgggtgaacaccctgtctatgcgccctggagaagccagacaagggcgccagctacac
accacaggctctgaagaagttccccgccgacctggattttgctagacagtactacgtgatgctgtacaacaccgccgacgagctgctgttca
agggaatcctgcccaacctgcctagcgcctaccagaacaccgtcacgctaacaggatgacagattctgtgatcagactgctgagcgccct
gctgcgggtgtccgaggtggagtctagggctagagtgggcaaggtgtttaacgcccagctctgcccaaggcctccagaaaggctctgg
gcaccctgggaaaggagctgttcatgtactttggacaccggccctgcgcatccactttcggaatgaagctgtttgaggacacaaacctgtgc
gccatcaacgctaagcgggtgaccatcatgcctaaggacgacgtgagcgtgacaaaggccctgcagcacctgtctcactacttcgaggg
gtgctgaagtgtctggtgagcatgccactgtgggctaagcacatgtccgatgagcagatccaggctcgtggaggagcccctttgagaagc
ctgtgatgatctctatgggaaacgagaacgtggtggagatcaagggcctggagatccagggaaccgaccctgtgagcgccgtgaccctg
agcctgctggaccccgagacctga AA (N→C terminus) (SEQ ID NO. 42)
MQLASTYTAYIVGYVHYGDWLKNEKINRVVFVWNFLRVNTLSMRPWE
KPDKGASYTPQALKKFPADLDFARQYYVMLYNTADELLFKGILPNLPSAYQNTVHANR
MTDSVIRLLSALLRVSEVESRARVGKVFNAPALPKASRKALGTLGKELFMYFGHRALRI
HFGMKLFEDTNLCAINAKRVTIMPKDDVSVTKALQHLSHYFEGVLKCLVSMPLWAKH
MSDEQIQGFVEEPFEKPVMISMGNENVVEIKGLEIQGTDPVSAVTLSLLDPET*

4T1.2 polyepitope vaccine
DNA (5'→3') (SEQ ID NO. 43)
atgatttgcgatctgcttcagctgtttattggcgcacgccttgaatctgattaaattagtacgcggccgcaaaccgctgt
cttggcttagccgcgccccgcgtccgaccggccctccagcgtcccgcttagcgagtaagagccacagcagcgttaaacgctgcgtaaaa
tgcatcatgccgccgtgggacaggataaaaccggtctcttatggaggaagtccccctttccgcacacagcccgcattccgggactccggtcatt
ggatgaagtccaaccgcagcagctgccagcaacagatccaaaactgctgaaattgatccgtcaaggctgaaaaagccgaacgtgaatttcgt
aaaaaagcggcgctgttggaaaccccacggggtaaaattcaggcaaaaaatggagcctggtaccgttttctattccggttttcgatattttgc
aagattcgcggccttgatcccgcacaatccacgcgtagcggtcaaaacgacgaacaacctcgttatgaaaacagtgtttgcctggagcg
cgattcgtttaccctgacggccgtcgccgtggttttccgcctgacaacttctgcgccccggggtaggcgtaaccgtagctg
ctttaatggcgatggagctcttccgcgtctgtttggttgtggttacaggaattatcaatcacccttttgctgttcccgcgtgaaaacgcgacccac
cactctaagatggacttagaaaaaccgaactacatcgtgccagattgtatgccggttgtttatgataagctgccacaaccgccgactcatcac
cacggtcgtaaccaggttgtagtggctgcgggtcgtagtagctggggtgcttggctgagtggcgcgctccacgtgtatagcttttcaagtcat
catctgcgcgttgaaaaactgcaactcgagagcgagctgaacgaaagccgtacggaatgcattacccgccacgtcgcagtgacggccca
ccaccatgattctgttaccaagttcaaactgcaaggctcgccggtcccgcgccttcgtcagtccttattgtgggtgaaccggcacgtccgcc
gcatcatattaacgccgaggaatcggaaattcgctacagtacctggaagcgcgcggtaatgaagagcattggctgggttaccacacagagt
ccagttagtatcagctacttttcccgtgcggcgtacgcggggttgtttaccccgttataccgtccgggcctgtcatgccagatttaa AA (N→C terminus) (SEQ ID NO. 44)
MFAICFSCLLAHALNLIKLVRGRKPLSWLSRAPRPTGPPASRLASKSHSSV
KRLRKMHHAAVGQDKPVFMEEVPLPHTARIPGLRSLDEVQPQQLPATDPKLLKIRKAE
KAEREFRKKAALLETPRGKIQAKKWSLVPFSIPVFDILQDCAALIPHNPRVAVKTTNNLV
MKNSVCLERDSFTLTALRRRGFPPDAINNFCARVGVTVAALMAMELFRVCLVVVTGIIN
HPLLFPRENATHHSKMDLEKPNYIVPDCMPVVYDKLPQPPTHHHGRNQVVVAAGRSSW
GAWLSGALHVYSFSSHHLRVEKLQLESELNESRTECITATSQMTAHHHDSVTKFKLQGS
PVPRLRQSLLWGEPARPPHHINAEEESEIRYSTWKRAVMKSIGWVTTQSPVSISYFSRAAY
AGLFTPLYRPGLSCQI* pGTB16 polyepitope vaccine
DNA (5'→3') (SEQ ID NO. 45)
ggcgacaactttcgtgagaccctgaaaaagaagaaacgcacgcttgtaatgttttacgcaccatggtgcccacacca
tcatctgttaatgcgcgaagtgccactgcgttgtacgatcagcctttgggacacctaccagagcgaaccagacggtttccaccacactcgtc
gcctgcgcgaacaacagaaaaccgcagaatgtgatgtgggcgattaccgttgtccgcaggatcagtctgcggcgttgctggtgcgcgtgt
gcagttcacagaaacctttctgatgaacgcgataagcagatgaaatgtctggaatccctggcggctacgaagttttagaacaggagaaa
ggtgcactgtctgatggtgaaattgtgagtctgtctattgaattttacgaaggccatcactgcccgtcacctcaggcagagaaacgcttgccga
aattacacttagaaattatcgataaggactctaagacccgccgcgttaaaactgacagcaccggaacgcattcactctatgctatgtatcagg
attacgaaattatgtttcatgtttcgcaccattgcgcccttggagcagccgcgctggcagtagtcaaaagcacgctggagtgggcgccgaaa
ttccaactgcaactgttccaccacgccgcagtaacgaaagagcctattccggtcctgccgaccgttcgttataatatgggtggcatcccgact

```
aattacaagggcaatacoctggaacaggagcaggaagcgctggtgaatcacttgtggaagcgtatggataaattggaagcagagaaacac
catcattgtccgagtgcttattatgaggcagctctgctgcagctgtgggtcacagaagcgtgcacctaccgcccgtcagcacagcaccatca
tgaccgttttccactgcgtaatgcagaaatggctaaagtcctggaaatttccagcgtgcctgcttcagaccgtatggtgcaccatcacaccgg
agaaaaaccatatcgttgcaaggtttgcgggaccgccttcacgtggcattcacagctggcccgccactaa AA (N→C terminus) (SEQ ID NO. 46)
GDNFRETLKKKKRTLVMFYAPWCPHHHLLMREVPLRCTISLWDTYQSEP
DGFHHTRRLREQQKTAECDVGDYRCPQDQSAALLVRAVQFTETFLMERDKQSKWSGIP
AAYEVLEQEKGALSDGEIVSLSIEFYEGHHCPSPQAEKRLPKLHLEIIDKDSKTRRVKTDS
TGTHSLYAMYQDYEIMFHVSHHCALGAAALAVVKSTLEWAPKFQLQLFHHAAVTKEPI
PVLPTVRYNMGGIPTNYKGNTLEQEQEALVNHLWKRMDKLEAEKHHHCPSAYYEAAL
LQLWVTEACTYRPSAQHHHDRFPLRNAEMAKVLEISSVPASDRMVHHHTGEKPYRCKV
CGTAFTWHSQLARH*
```

Immunoprecipitations and immunoblots. HeLa-A2 cells were transduced with a retroviral vector pMIG encoding polyepitope antigen. GFP+ cells were FACS-sorted and cultured for 24 h with or without 50 μM MG132 (Boston Biochem, Cambridge, MA). Expression of GFP protein was also confirmed by western blot of total cell lysate with anti-GFP antibody (Santa Cruz, Dallas, TX). To detect the production and degradation of polyepitopes, immunoprecipitation and immunoblot were performed as previously described. Briefly, cells were lysed in PBS with 1% Nonidet P-40. Post-nuclear lysates were then incubated with anti-HA-Sepharose (Covance). After washes, precipitated proteins were eluted by boiling in LDS sample buffer (Invitrogen) and separated by SDS-PAGE. Proteins were detected with anti-HA (clone 16B12, Santa Cruz) and visualized by chemiluminescence using the ECL system (ThermoFisher).

Flow cytometry. To measure cell surface expression of neoantigens, a TCR mimic Ab (TCRm) specific for SVG9/HLA-A2 was used to stain HeLa-A2 cells transduced with polyepitope DNA. As a positive control, parental HeLa-A2 cells were incubated with 10 .tM SVG9 peptide for the last hours before cell wash. PE-conjugated goat anti-mouse Ig Ab (BD Biosciences, San Jose, CA) was used as secondary Ab. Data from viable cells, gated by forward and side scatter, were acquired on a FACSCalibur (BD Biosciences) and analyzed using FlowJo v10 software (TreeStar, Ashland, OR).

CTL assay. In vitro CTL assays were performed as previously described. Briefly, target cells (transduced HeLa-A2) were labeled with 0.2 mCi of [$^{51}$Cr] (PerkinElmer, Wellesley, MA) and incubated with SVG9-specific T cells generated from WNV-KUN-immunized HHDII spleen cells. Parental HeLa-A2 cells with or without SVG9 peptide were used as controls. Maximum lysis was achieved by adding 5% Triton-X 100 (Sigma-Aldrich) to the wells. Spontaneous lysis was determined with cultured target cells without CTLs. Supernatants were collected and read by an Isomedic γ-counter (ICN Biomedicals, Huntsville, AL). The specific lysis was calculated by the formula: 100×[(experimental $^{51}$Cr release−control $^{51}$Cr release)/(maximum $^{51}$Cr release−spontaneous $^{51}$Cr release)].

Tumor challenge and TIL analysis. E0771 and 4T1.2 tumor cells were dislodged with Trypsin/EDTA (ThermoFisher) and washed twice with $Ca^{2+}/Mg^{2+}$-free PBS. $10^6$ cells were injected subcutaneously into the flanks of female mice. Tumor sizes were measured using an electronic caliper. For checkpoint blockade, 200 μg of anti-PD-L1 (clone 10F.9G2) or isotype control (clone LTF-2) antibody (both from Bio X Cell, West Lebanon, NH) was administered i.p. at the indicated time points.

To study the neoantigen-specific T cells present in the tumor after DNA vaccination, tumors were harvested and digested with Tumor Dissociation Kit (Miltenyi Bio-tec) following the manufacturer's instruction. Single cell suspensions were prepared by passing through 70-μm cell strainers after cell debris was removed and red blood cells were lysed. Tumor-infiltrating leukocytes were stained with dextramer and analyzed by flow cytometry.

Tetramer/dextramer staining. PE-conjugated SVG9/HLA-A*0201 tetramer was obtained from the National Institute of Allergy and Infectious Diseases tetramer facility (Emory University, Atlanta, GA). APC-conjugated Lrrc27/H-2D$^b$ dextramer was manufactured by Immudex (Copenhagen, Denmark). Cells were stained with tetramer or dextramer for 40 min at 37° C. Fluorophore-labeled antibodies specific for surface markers (CD45, CD3e, and CD8a) were subsequently added and the cells were incubated for an additional 20 min at 4° C. Cells were acquired on a FACSCalibur and data were analyzed with FlowJo v10 software.

Human subject. Patient GTB16 was a 25-year-old male with Lynch Syndrome-associated metastatic pancreatic neuroendocrine tumor that was refractory to standard of care treatment. He was initially diagnosed and treated at Barnes-Jewish Hospital, St. Louis, MO. He received palliative carboplatin/etoposide and concurrent lanreotide with a partial response. Because his tumor demonstrated microsatellite instability, he was also treated with pembrolizumab as maintenance therapy on a compassionate use protocol with a partial response. Repeat surveillance MRI demonstrated mixed response with evidence of on-going progression. Due to the lack of any effective treatment options available, he was treated with a neoantigen DNA vaccine (pGTB16) on a compassionate use basis. The protocol was approved by the Washington University School of Medicine Institutional Review Board, Institutional Biosafety Committee, and the Food and Drug Administration. Written informed consent was signed by the patient for the treatment and associated research studies. A total of three vaccinations with at least 21 days in between injections were administered. pGTB16 vaccine was delivered intramuscularly using an integrated electroporation device (TDS-IM system, Ichor Medical Systems). Blood was drawn pre- and post-vaccination and peripheral blood mononuclear cells (PBMC) were isolated by Ficoll-Paque PLUS (GE Healthcare) density centrifugation and cryopreserved. PBMCs were used in IFN-γ ELISpot assay to evaluate the generation of a neoantigen-specific immune response.

ELISpot assay. IFN-γ ELISpot$^{PLUS}$ Kits (Mabtech, Cincinnati, OH) were used as instructed by the manufacturer to measure the in vivo neoantigen-specific immune response. For pre-clinical studies, mouse spleen or lymph node cells were typically seeded at 2-4×10$^5$ per well in triplicates. Neoantigen (MT) and wildtype (WT) counterparts were synthesized by Peptide 2.0 or GenScript and were used at the indicated final concentration. For clinical studies, cryopreserved PBMCs were thawed and cultured for 12 days in the presence of human IL-2 (50 U/mL) and 25 μM each of the pooled overlapping peptides (each pool contained two mutated genes). After an overnight rest in culture medium without peptides and IL-2, $10^5$ of the in vitro-stimulated cells were co-cultured in the ELI-Spot plate for 20 h with $10^4$ of autologous PBMCs that were pulsed with 100 μM individual long peptide and irradiated (3000 Rad). The ELISpot plates were scanned and analyzed on an Immuno-Spot Reader (CTL, Shanker Heights, OH).

Statistics. Data were analyzed using GraphPad Prism 8 software (GraphPad, La Jolla, CA) and presented mainly as mean±SEM. The Mann-Whitney test or one-way ANOVA test were used to compare between vaccination groups. Paired t-test was performed in some cases when different conditions were compared using the same specimens. A P value equal or less than 0.05 is considered statistically significant. Figures were prepared using Adobe Illustrator CS6 (Adobe, San Jose, CA).

Peptide binding assay. To measure the binding affinity of MT and WT Lrrc27 peptides to H-2Db molecules, RMA-S cells were pulsed with different concentrations of peptides and incubated overnight at 37° C. Cells were then stained with H-2Dd-specific monoclonal antibodies (clone 34-5-8) followed by PE-labeled secondary antibody (BD Biosciences). Monoclonal antibody was provided by Dr. T. Hansen (Washington University School of Medicine) as pre-titrated hybridoma supernatant. Mean Fluorescence index (MFI) was determined on a FACSCalibur flow cytometer (BD Biosciences).

CD4+ T cell purification and ELISpot assay. Spleens were harvested from Balb/c mice vaccinated with SLPs. CD4+ T cells were purified using the EasySep mouse CD4+T cell isolation kit (STEMCELL Technologies, Cambridge, MA) following manufacturer's instruction. Purified CD4+ T cells were used in a modified IFN-γ ELISpot assay in which 105 of irradiated (3000 Rad) naïve spleen cells were added to each well with or without 5 μg/ml of each 29-mer neopeptides.

Results

Figures 11A, 11B:
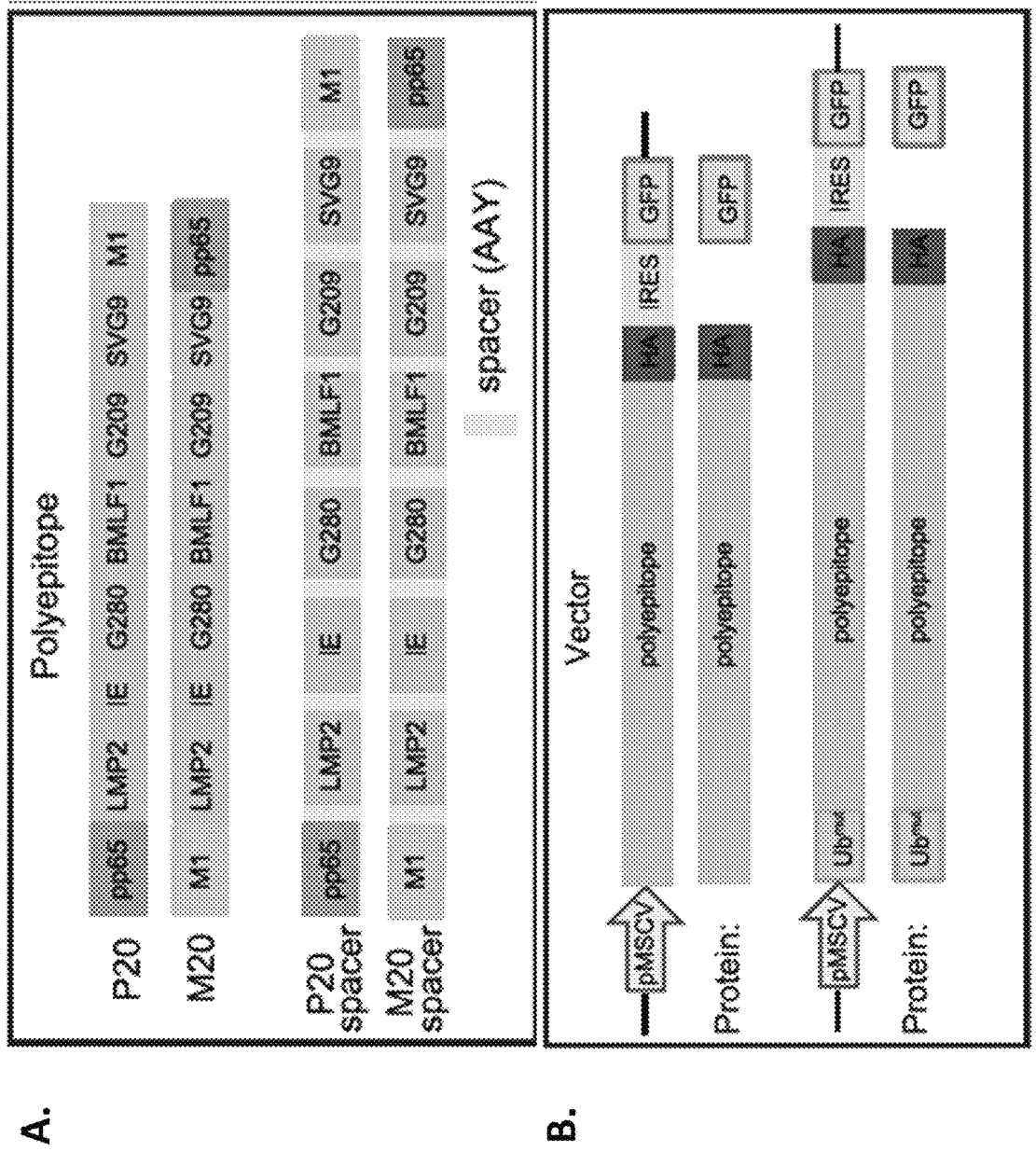
FIGS. 11A-11H. Optimizing the polyepitope DNA vaccine design.

Optimizing the Design of Polyepitope Neoantigen DNA Vaccines for Enhanced Presentation and Recognition A model system was first established to optimize the polyepitope DNA vaccine platform by using eight well-characterized HLA-A2-restricted epitopes. This model system allowed us to address important questions about polyepitope design such as size of the neoantigen epitope, inclusion of spacers, and addition of a ubiquitin tag to enhance antigen processing. The HLA-A2-restricted epitopes included viral (EBV, HCMV, influenza, and West Nile Virus) and tumor-associated antigens (melanoma gp100) (Table 4). With the exception of the CMV (pp65) and influenza (M1) epitopes, the order of the other six epitopes was consistent between the model polyepitope constructs (FIG. 11A). The spacer inserted between epitopes consisted of three amino acids (AAY). To study whether antigen processing efficacy is different for short vs. long epitopes encoded in polyepitope DNA vaccines, polyepitope DNA constructs were created that encode either minimal epitopes (9-10 AA) or longer epitopes (20 AA) with native residues flanking the minimal epitopes. The constructs were designated as P9/P20 (starting with pp65) and M9/M20 (starting with M1). To facilitate in vitro assays, the polyepitope constructs integrated an HA tag at the C-terminus. Co-expression of GFP was made possible through an IRES element and served as control for transduction as measured in immunoblot (IB) analysis or flow cytometry (FIG. 11B).

TABLE 4

List of HLA-A2-restricted epitopes included in the octamers for optimizing polyepitope DNA vaccine design (* underlined indicate minimal epitope sequences).

| Epitope ID | Amino acid sequence* |
|---|---|
| pp65 (CMV) | GILARNLVPMVATVQGQNLK (SEQ ID NO. 47) |
| LMP2 (EBV) | GPVFMCLGGLLTMVAGAVWL (SEQ ID NO. 48) |
| IE (CMV) | VLCCYVLEETSVMLAKRPLI (SEQ ID NO. 49) |
| G280 (gp100) | VVTHTYLEPGPVTAQVVLQA (SEQ ID NO. 50) |
| BMLF1 (EBV) | AIQNAGLCTLVAMLEETIF (SEQ ID NO. 51) |
| G209 (gp100) | SSAFTITDQVPFSVQLRALD (SEQ ID NO. 52) |
| SVG9 (WNV) | AWDFGSVGGVFTSVGKAVHQ (SEQ ID NO. 53) |
| M1 (Flu) | SPLTKGILGFVFTLTVPSER (SEQ ID NO. 54) |

Figure 16A:
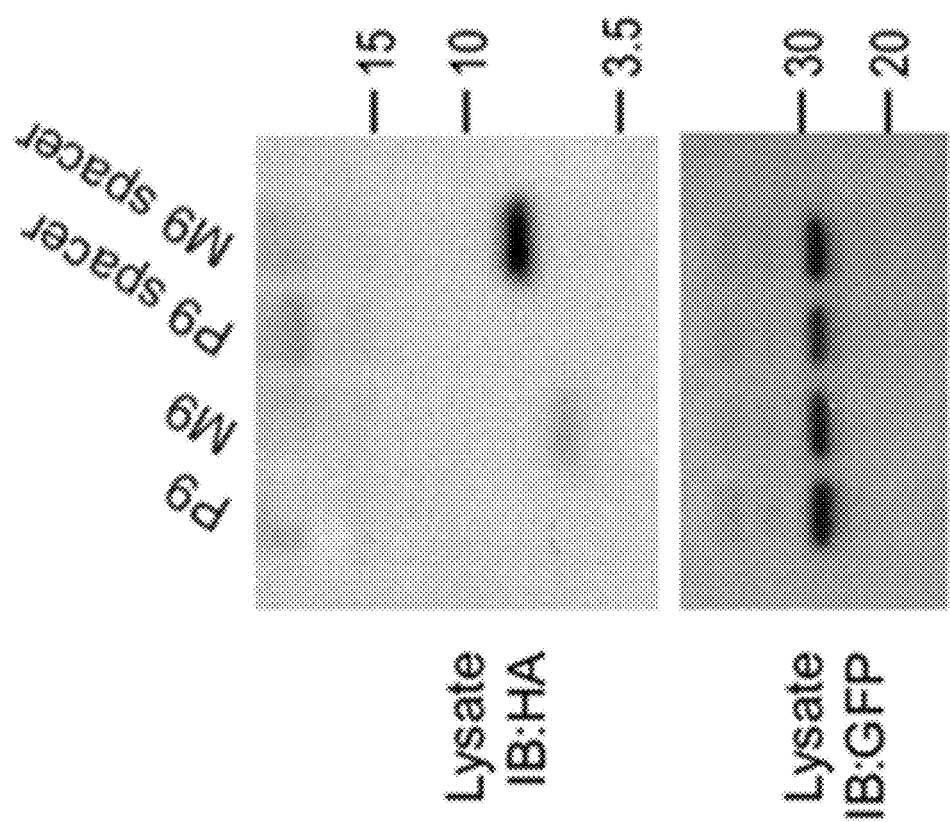
FIGS. 16A-16F. Expression of polyepitope constructs and the presentation of antigens.
Figure 16B:
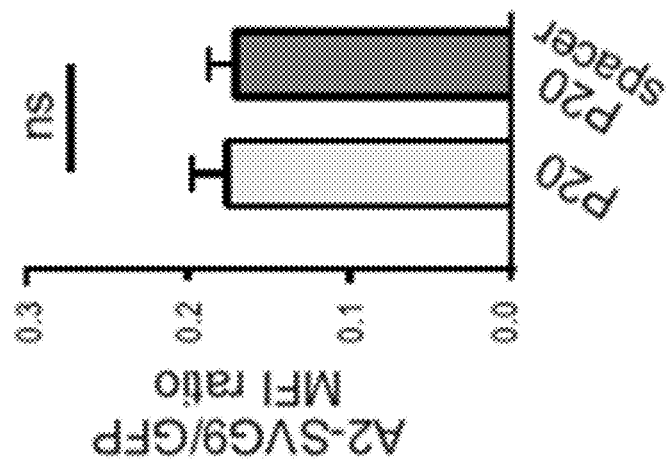
Figure 16C:
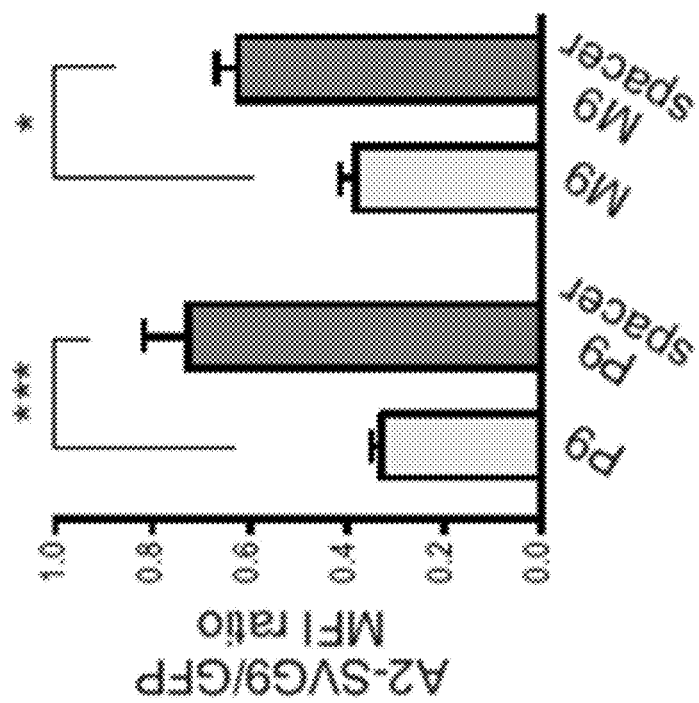

To study the expression and processing of the polyepitope constructs, HeLa-A2 cells were transduced with different constructs. Cell lysates were immunoprecipitated (IP) followed by D3 to detect HA-tagged polyepitopes. It was found that GFP proteins were equally expressed in the transduced cells, as determined by D3. However, the P9 and P9-spacer constructs were undetectable while M9 and M9-spacer constructs were readily detected (FIG. 16A), suggesting that polyepitopes starting with an unstable amino acid (such as N in pp65) degraded more rapidly than constructs starting with a stable residue (such as G in M1). This observation is consistent with the N-end rule of protein degradation. The addition of spacers in both P9 and M9 constructs resulted in increased surface presentation of SVG9 as determined by flow cytometric analysis using a TCR-mimic antibody specific for SVG9/HLA-A2. But in the case of construct P20, the addition of spacers did not increase the presentation of SVG9 (FIGS. 16B & 16C). These data suggest that additional amino acids in the spacers flanking the 9-mer epitopes might help with processing of the intact minimal epitope, but that spacers may not be required if native flanking sequences are present. It was therefore decided to focus on the DNA construct P20, which encodes long epitopes.

Figures 11C, 11D:
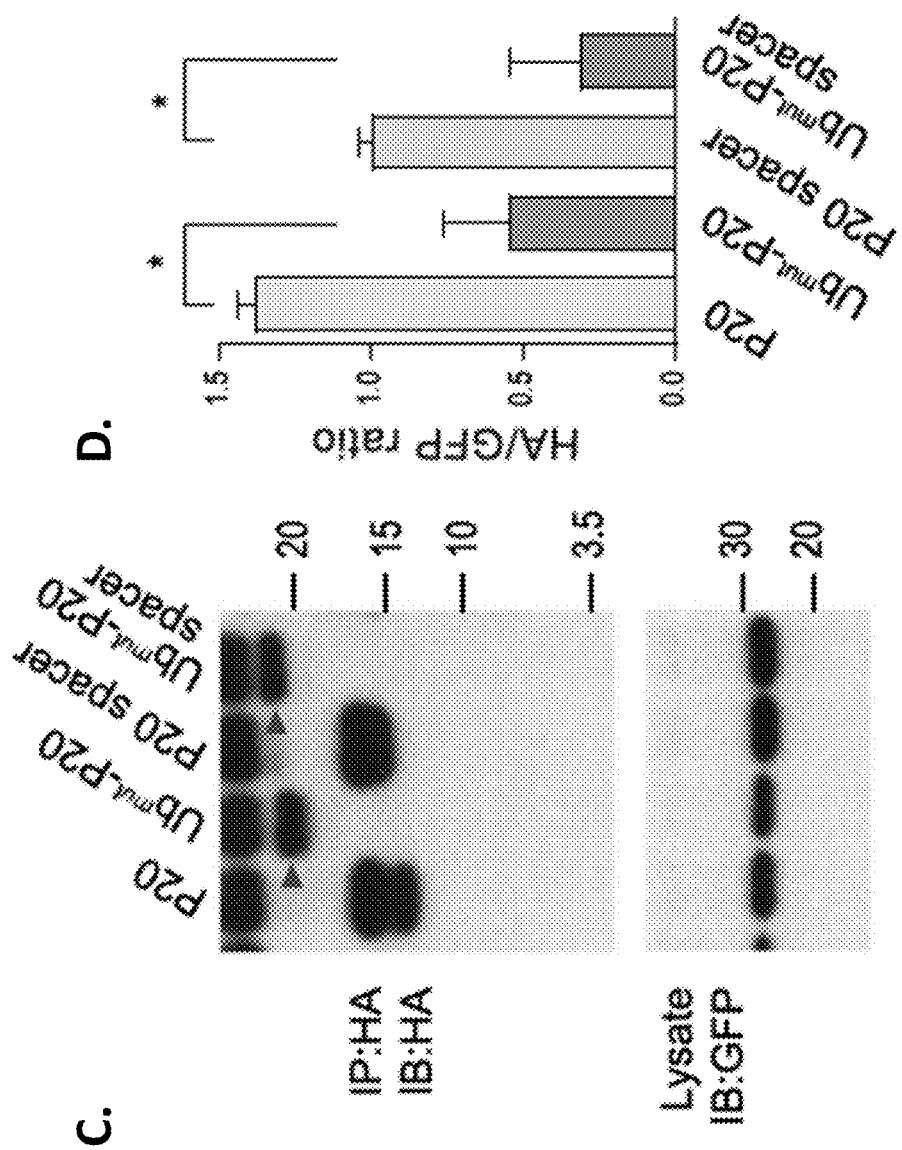
Figures 11E, 11F, 11G:
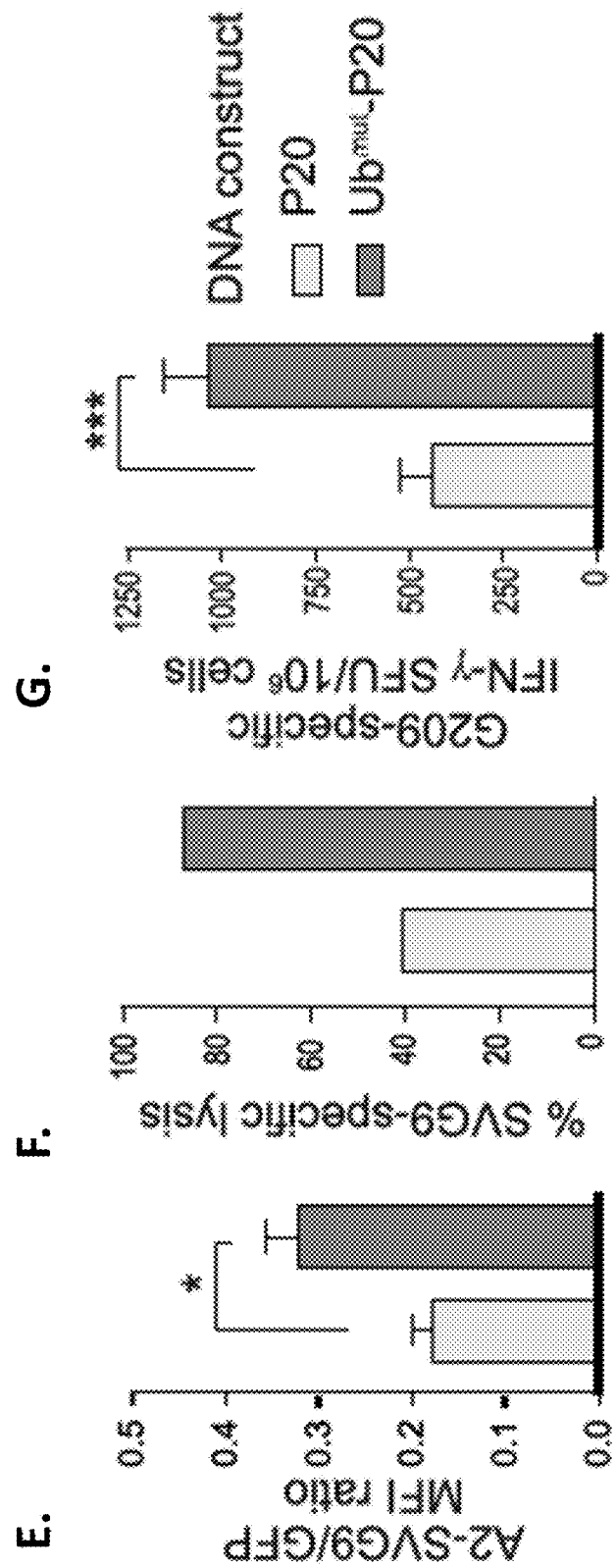
Figure 11H:
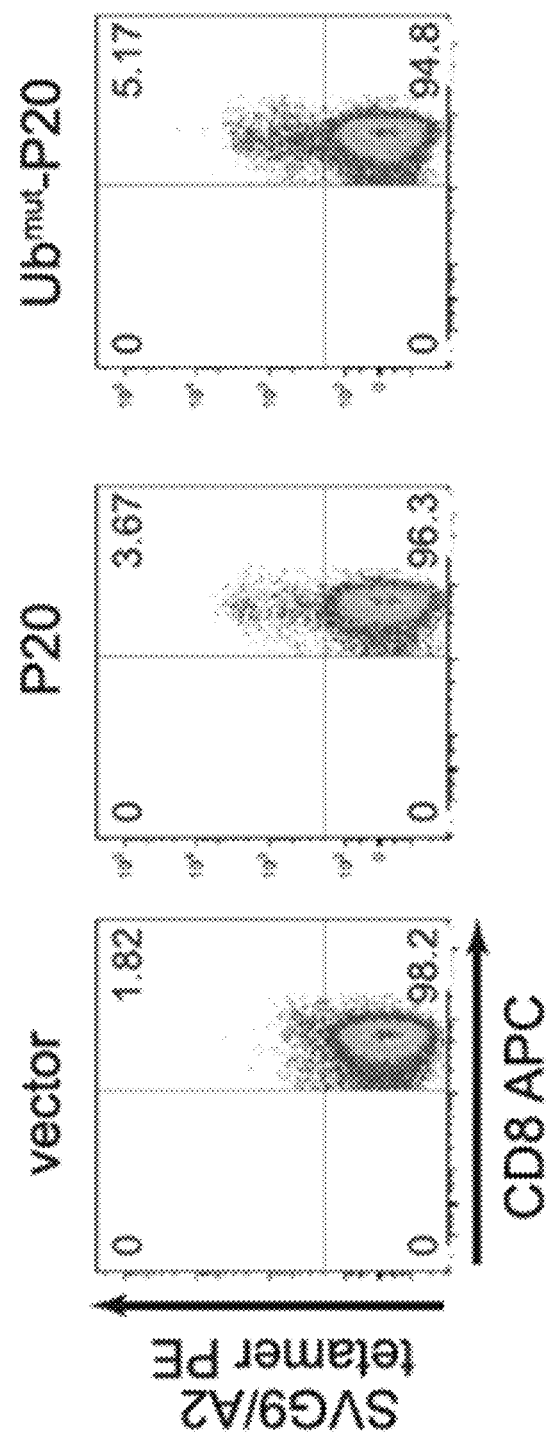
Figure 16D:
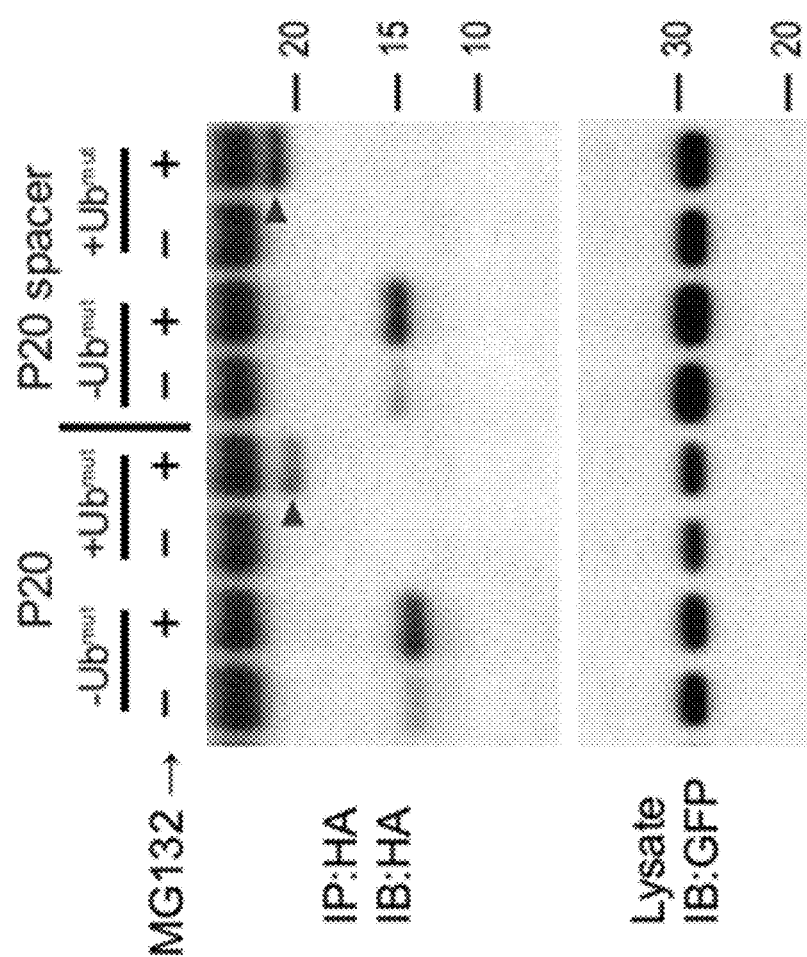
Figure 16E:
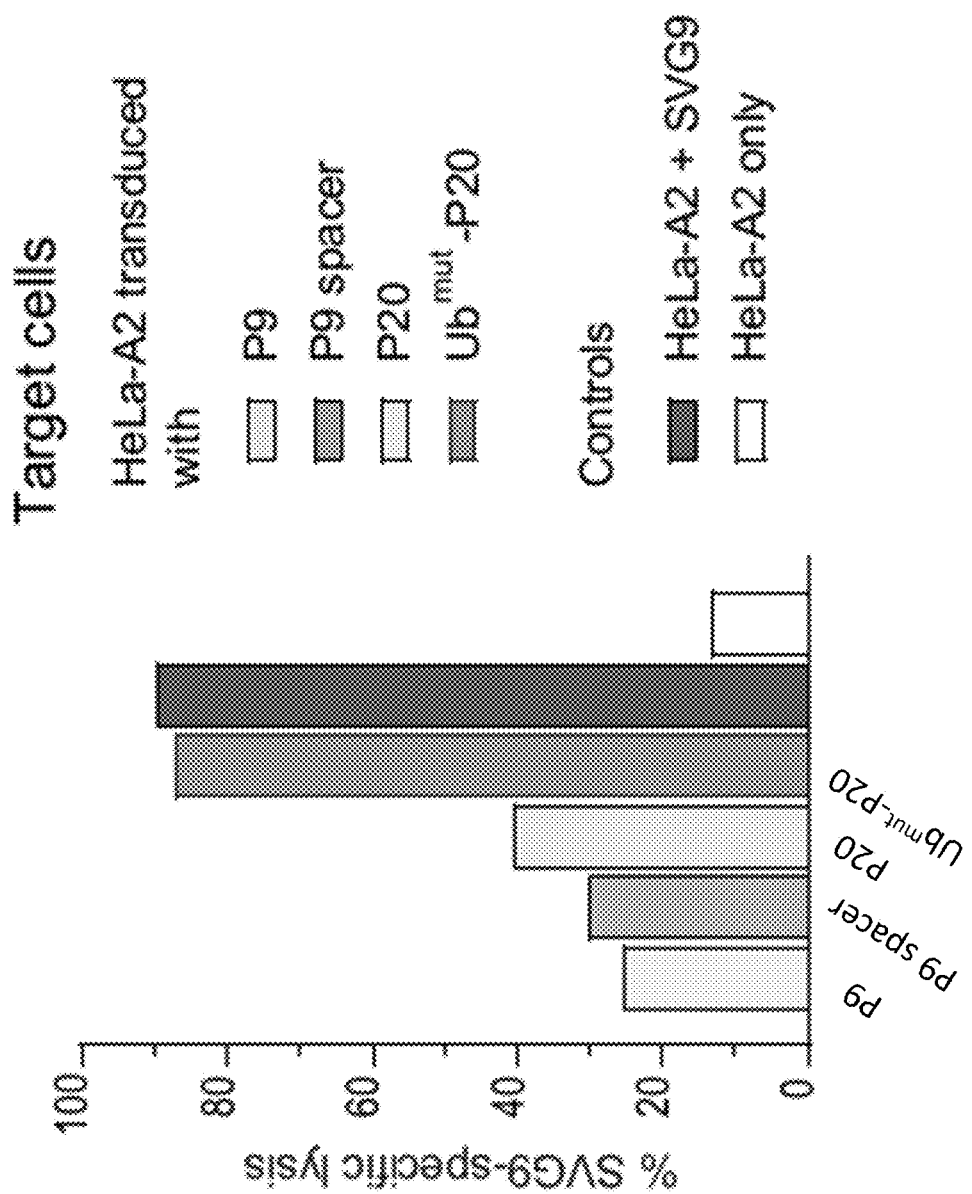
Figure 16F:
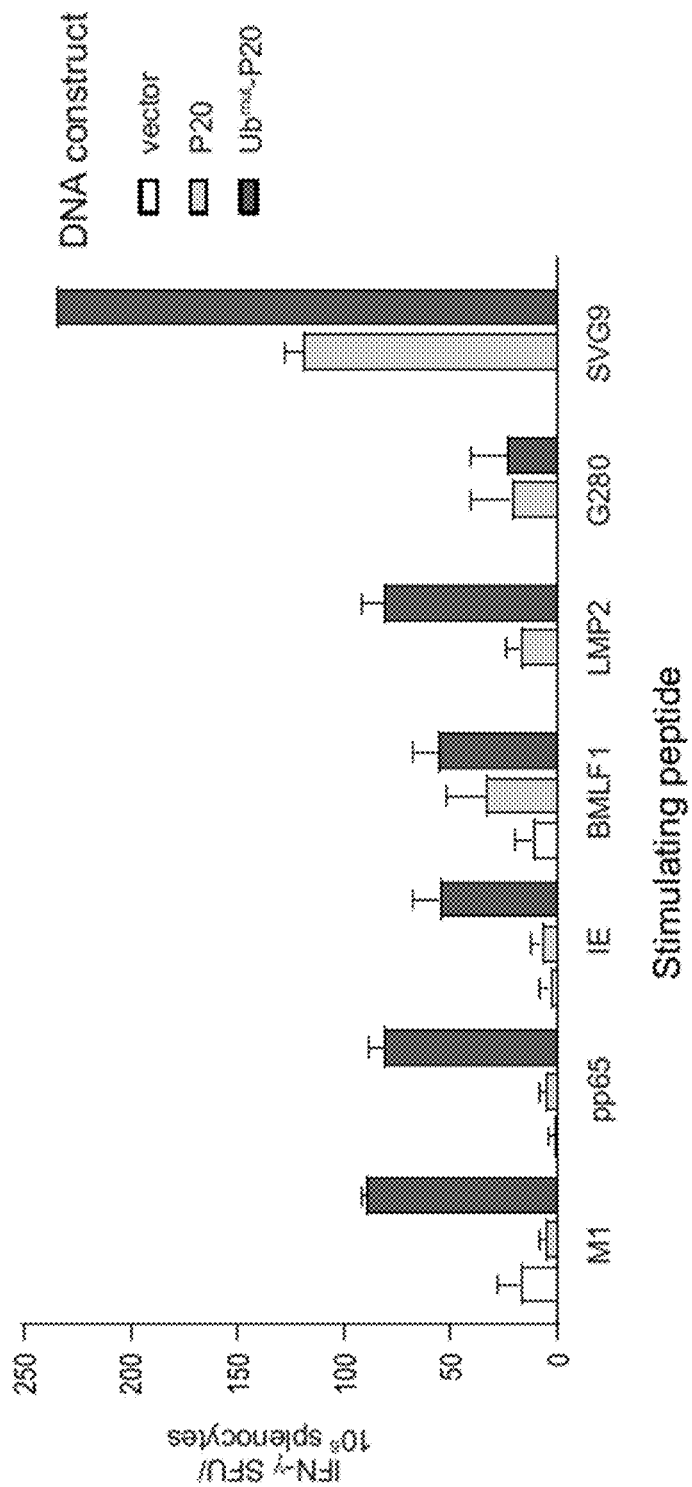

In some embodiments described herein, because MHC I binding peptides are initially processed in the cytosol by the ubiquitin/proteasome pathway, integrating a mutant form of ubiquitin (Ub G76V or $Ub^{mut}$), which is resistant to ubiquitin hydrolysis, to the N-terminus of the polyepitope constructs accelerates ubiquitination-mediated degradation of the polyepitopes and antigen processing. Indeed, integration of $Ub^{mut}$ before the polyepitope construct resulted in faster protein degradation, compared with the same construct without the addition of $Ub^{mut}$, as determined by D3 analysis (FIGS. 11C & 11D). The integration of $Ub^{mut}$ does not impact the transduction efficacy and protein expression, as the GFP levels were similar comparing constructs with or without the Ub$^{mut}$ tag. Notably, this increased polyepitope degradation appeared to be associated with a higher surface presentation of HLA-A2/SVG9 complexes (FIG. 11E). The degradation of polyepitope proteins was proteasome-dependent, as addition of the proteasomal inhibitor MG132 protected the proteins from rapid degradation (FIG. 16D). Consistent with the flow cytometric analysis, in a $^{51}$Cr-releasing cytotoxicity assay using an A2/G209-specific T cell line, HeLa-A2 cells transduced with Ub$^{mut}$-P20 were lysed more efficiently compared to cells transduced with P20 (FIG. 11F; FIG. 16E). Additionally, when the DNA constructs were used to vaccinate HHD II mice, the Ub$^{mut}$-P20 vaccine generated more robust CD8 T cell responses in vivo compared to the P20 vaccine, as determined by an IFN-γ ELISpot assay (FIG. 11G; FIG. 16F) and SVG9/HLA-A2 tetramer staining (FIG. 11H).

Taken together, these results suggested that a polyepitope DNA construct encoding long epitopes (≥20 mers), in tandem with an Ub$^{mut}$ fused to the N-terminus, is optimal for processing and presentation of epitopes among the constructs tested. This design was therefore used for subsequent studies. Of note, although in exemplary embodiments the optimized vaccine is superior for the majority of the encoded antigens, in some embodiments it is not superior for all antigens compared to the control vaccine (FIG. 16E).

Figure 12A:
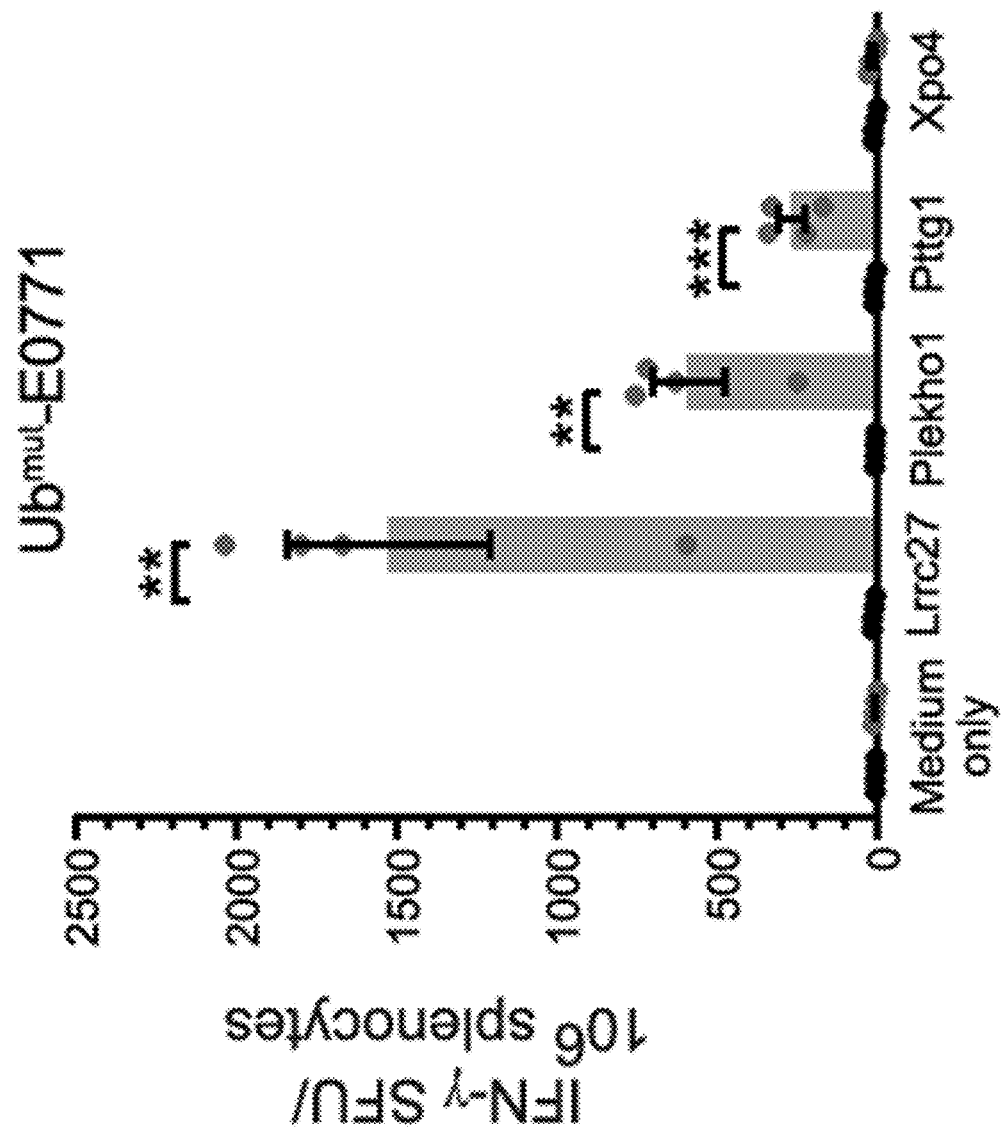
FIGS. 12A & 12B neoantigen DNA vaccine elicit neoantigen-specific T cell responses in vivo. Neoantigens were identified for E0771 and 4T1.2 breast cancer models. Polyepitope neoantigen DNA vaccines were created for each and were used to immunize mice by gene gun. Spleen cells from mice vaccinated with polyepitope DNA vaccines (red) and control empty vector DNA (black) were harvested and used in IFN-γ ELISpot assay. T cell responses to selected neoantigens were shown (mean±SEM) for Ub$^{mut}$-E0771 (FIG. 12A) and Ub$^{mut}$-4T1.2 (FIG. 12B). Of note, 8- to 10-mer minimal peptides were used in the assays for Ub$^{mut}$-E0771 (FIG. 12A), but 29-mer long peptides were used for Ub$^{mut}$-4T1.2 (FIG. 12B). Experiments were repeated at least two more times for panel a, and similar results were obtained. P<0.01, *P<0.001, t-test.
Figure 12B:
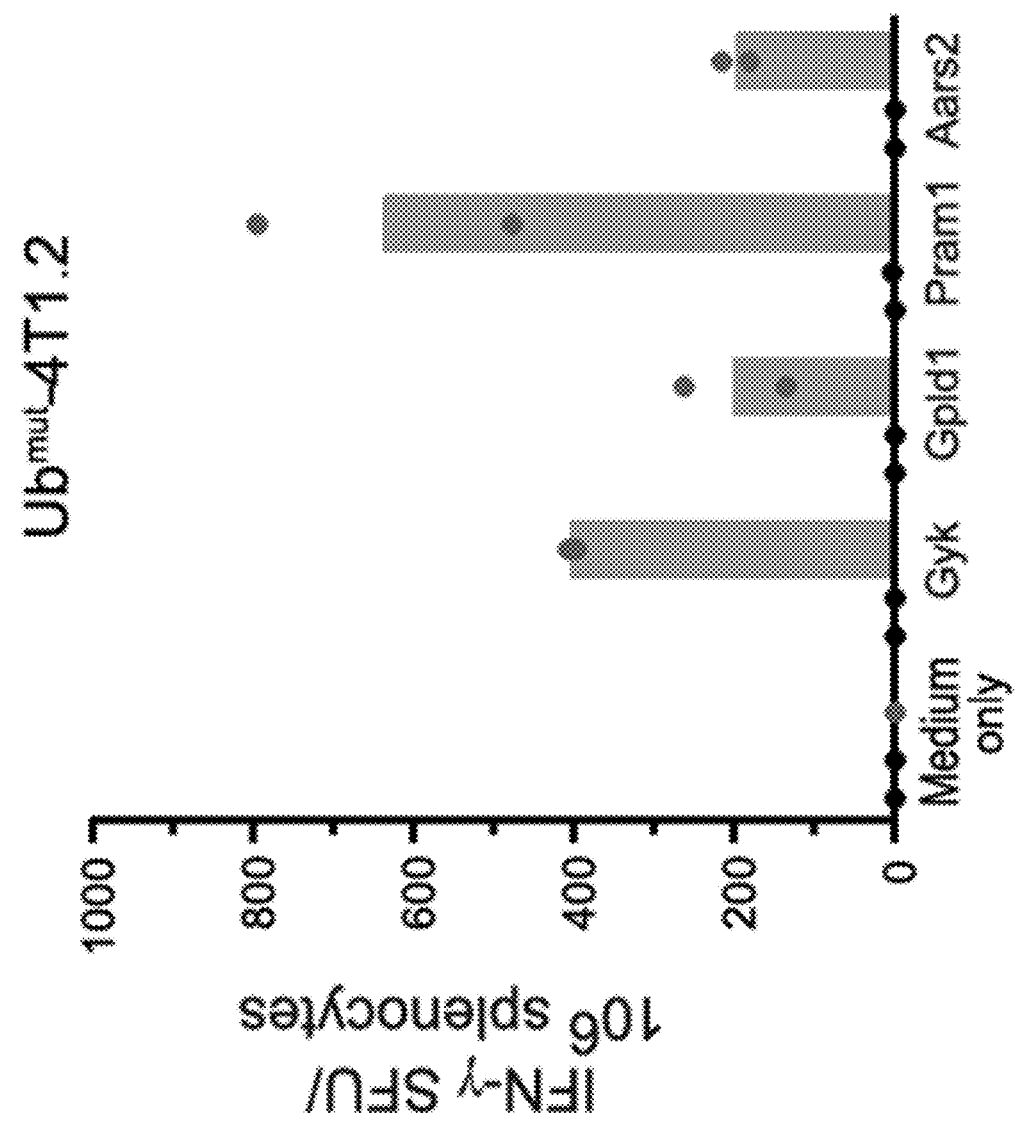
Figure 17:
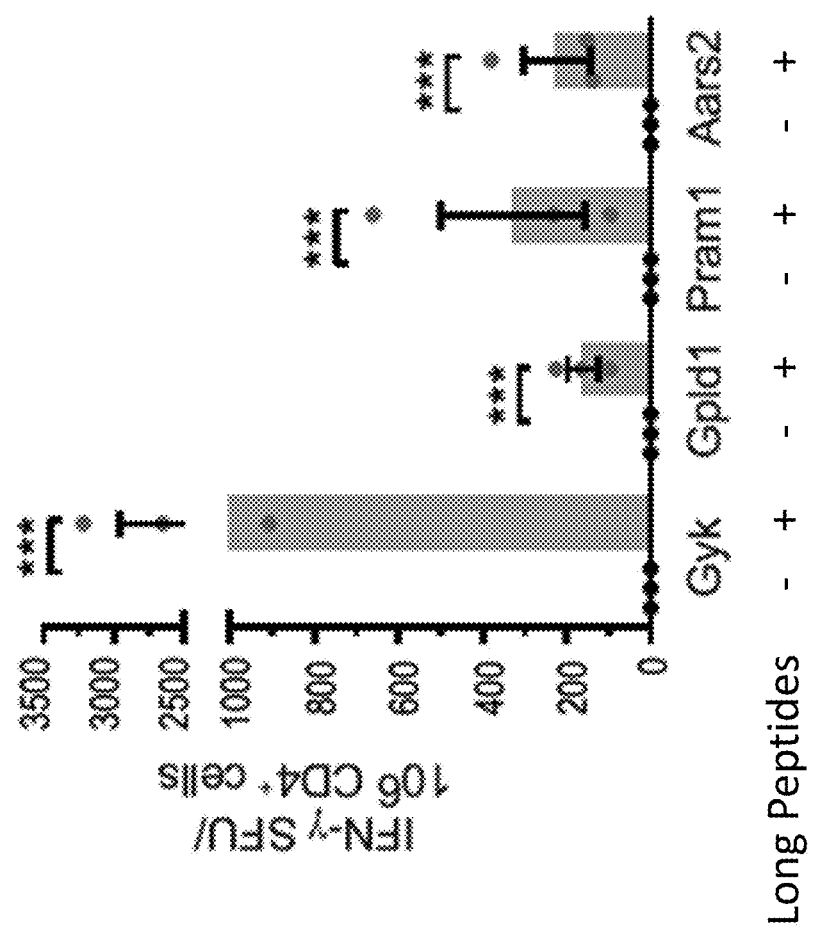
FIG. 17 shows SLP vaccines generated neoepitope-specific CD4 T cell responses. Female Balb/c mice were vaccinated with individual SLP/poly(I:C) as described in the Methods. Spleen cells were harvested and purified CD4+ T cells were used in an IFNγ ELISpot assay. Irradiated spleen cells from naïve mice were added into each well as feeder cells with (red) or without (black) corresponding long peptides. The experiment was repeated once and similar result was obtained. Error bars, SEM. *** P<0.001, t-test.

Optimized Polyepitope Neoantigen DNA Vaccines Elicit Immune Responses in Preclinical Mouse Breast Cancer Models Proof-of-concept studies were carried out using E0771 and 4T1.2, two syngeneic murine mammary tumors. E0771 and 4T1.2 recapitulate many of the biologic features of human breast cancer, including the dynamic tumor and immune system interactions restraining endogenous immune responses and serve as models of estrogen receptor-positive (ER$^+$) and triple-negative breast cancer (TNBC), respectively. Both 4T1.2 and E0771 were sequenced and successfully identified candidate neoantigens with strong predicted binding affinity to the corresponding MHC class I alleles using pVACseq, a computational pipeline (Table 1 and Table 2). Polyepitope Ub$^{mut}$-E0771 and Ub$^{mut}$-4T1.2 neoantigen DNA vaccines were created and used to vaccinate C57BL/6 or Balb/c mice, respectively. Neoantigen-specific T cell responses were detected by IFN-γ ELISpot assay for three neoantigens (Lrrc27 G330A, Plekho1 P251S, and Pttg1 V53L) encoded in the Ub$^{mut}$-E0771 polyepitope DNA vaccine (FIG. 12A). Of note, short peptides corresponding to the minimal MHC class I epitopes were used in these assays, suggesting a CD8 T cell response. Neoantigen-specific T cell responses were also detected by IFN-γ ELISpot assay for four neoantigens (Gyk K505R, Gpld1 R829W, Pram1 Q572L and Aars2 A697P) encoded in the Ub$^{mut}$-4T1.2 polyepitope DNA vaccine (FIG. 12B). All four 4T1.2 neoantigens are known to contain CD4 epitopes as spleen CD4$^+$ T cells isolated from mice vaccinated with peptides responded to peptide restimulation ex vivo (FIG. 17). These results confirmed the ability of neoantigen DNA vaccines incorporating Ub$^{mut}$-polyepitope inserts to generate robust immune responses in clinically relevant preclinical models.

TABLE 1

Selective neoantigens identified in E0771 mouse breast cancer.
(* Amino acids that differ from wildtype sequences are indicated in bolded font. The minimal epitope with the highest predicted affinity is underlined.)

| Mutation | MT 21-mer seq* | MT score | WT score | Fold change | H-2 allele | Normal VAF | Tumor VAF | RNA VAF | Gene FPK | ELI SPOT |
|---|---|---|---|---|---|---|---|---|---|---|
| Tmem101. G96V | QLASTYTAYIVGYVH YGDWLK (SEQ ID NO. 55) | 109.00 | 11934.00 | 109.49 | Kb | 0.78 | 36.80 | 45.78 | 7.83 | - |
| Pank3. G321W | NEKINRVVFVWNFLR VNTLSM (SEQ ID NO. 56) | 58.00 | 2292.00 | 39.52 | Kb | 0.55 | 38.33 | 50.63 | 25.00 | - |
| Plekho1. P251S | RPWEKPDKGASYTPQ ALKKFP (SEQ ID NO. 57) | 53.00 | 2070.00 | 39.06 | Kb | 0.37 | 68.82 | 58.93 | 27.36 | +++ |
| Exoc4. E901V | ADLDFARQYYVMLY NTADELL (SEQ ID NO. 58) | 91.44 | 1250.89 | 13.68 | Db | 0.00 | 66.67 | 85.54 | 18.80 | - |
| Lrrc27. G330A | FKGILPNLPSAYQNTV HANRM (SEQ ID NO. 59) | 90.00 | 1219.00 | 13.54 | Db | 0.00 | 55.80 | 95.45 | 2.98 | ++++ |
| Xpo4. V611L | TDSVIRLLSALLRVSE VESRA (SEQ ID NO. 60) | 65.00 | 579.00 | 8.91 | Kb | 0.00 | 41.10 | 60.11 | 17.60 | - |
| Pttg1. V53L | RVGKVFNAPALPKAS RKALGT (SEQ ID NO. 61) | 227.00 | 1141.00 | 5.03 | Kb | 0.00 | 36.36 | 31.77 | 64.10 | ++ |
| Neil3. P90H | LGKELFMYFGHRALR IHFGMK (SEQ ID NO. 62) | 166.57 | 475.14 | 2.85 | Kb | 0.00 | 57.80 | 87.04 | 3.34 | - |
| Hist1h3e. H114N | LFEDTNLCAINAKRV TIMPKD (SEQ ID NO. 63) | 296.29 | 829.35 | 2.80 | Kb | 0.57 | 31.79 | 57.78 | 195.92 | - |

TABLE 1-continued

Selective neoantigens identified in E0771 mouse breast cancer.
(* Amino acids that differ from wildtype sequences are indicated in bolded font. The minimal epitope with the highest predicted affinity is underlined.)

| Mutation | MT 21-mer seq* | MT score | WT score | Fold change | H-2 allele | Normal VAF | Tumor VAF | RNA VAF | Gene FPK | ELI SPOT |
|---|---|---|---|---|---|---|---|---|---|---|
| Prkag1. R268L | DVSVTKALQHLSHYF EGVLKC (SEQ ID NO. 64) | 187.00 | 443.00 | 2.37 | Kb | 0.00 | 30.51 | 47.07 | 25.43 | - |
| BC057079. V1474M | LVSMPLWAKHMSDE QIQGFVE (SEQ ID NO. 65) | 138.00 | 322.00 | 2.33 | Kb | 0.00 | 55.77 | 95.74 | 5.68 | - |
| Met. I851M | EPFEKPVMISMGNEN VVEIKG (SEQ ID NO. 66) | 73.84 | 166.10 | 2.25 | Db | 0.00 | 72.00 | 98.09 | 36.48 | - |
| Map3k6. T552A | LEIOGTDPVSAVTLSL LDPET (SEQ ID NO. 67) | 97.00 | 213.00 | 2.20 | Kb | 0.00 | 53.06 | 40.00 | 2.33 | - |

TABLE 2

Neoantigens identified in mouse breast cancer cell line 4T1.2. (* Amino acids that differ from wildtype sequences are indicated in bolded font. The minimal epitope with the highest predicted affinity is underlined.)

| Mutation | MT-27/29-mer seq* | MT score | WT score | Fold change | H-2 allele | Normal VAF | Tumor VAF | RNA VAF | Gene FPK | ELI SPOT |
|---|---|---|---|---|---|---|---|---|---|---|
| Aars2. A697P | VGQDKPVFMEEVPLPHT ARIPGLRSLDEV (SEQ ID NO. 68) | 17 | 1237 | 72.76 | Ld | 0 | 21.49 | 23.38 | 12.61 | - |
| Dync1h1. Y3123C | SKMDLEKPNYIVPDCMP VVYDKLPQPPTH (SEQ ID NO. 69) | 135 | 446 | 3.30 | Ld | 0 | 30.23 | 31.88 | 2.81 | + |
| Dtx2. P365L | LSRAPRPTGPPASRLASK SHSSVKRLRKM (SEQ ID NO. 70) | 290 | 877 | 3.02 | Kd | 0 | 80 | 76.88 | 10.50 | + |
| Pram1. Q572L | QPQQLPATDPKLLKLIRK AEKAEREFRKK (SEQ ID NO. 71) | 2413 | 4232 | 1.75 | Kd | 0 | 65.22 | 51.04 | 4.27 | ++++ |
| Cenpf. D1327E | RVEKLQLESELNESRTECI TATSQMTA (SEQ ID NO. 72) | 2390 | 4115 | 1.72 | Kd | 0 | 17.33 | 9.09 | 0.56 | - |
| Gyk. K505R | INAEESEIRYSTWKRAVM KSIGWVTTQSP (SEQ ID NO. 73) | 257 | 418 | 1.63 | Kd | 1.54 | 63.24 | 44.12 | 1.07 | +++ |
| Gprc5a. F119L | FAICFSCLLAHALNLIKLV RGRKPLSW (SEQ ID NO. 74) | 418 | 414 | 0.99 | Kd | 0 | 19.25 | 9.99 | 17.51 | - |
| Itprip.A 15G | MAMELFRVCLVVVTGIIN HPLLFPRENAT (SEQ ID NO. 75) | 293 | 263 | 0.90 | Ld | 0.32 | 20.13 | 30.43 | 46.91 | - |
| Zfp142. R1119C | EGCRGGRGQKRKRGCPQ THAVVLPLNNGD (SEQ ID NO. 76) | 162 | 138 | 0.85 | Ld | 0 | 36 | 62.07 | 20.63 | - |
| Dhx58. R654L | LETPRGKIQAKKWSLVPF SIPVFDILQDC (SEQ ID NO. 77) | 286 | 218 | 0.76 | Kd | 0 | 70.47 | 92.45 | 2.66 | - |
| Isoc2a. S195G | FKEIQKIIKEPVPDSGLLG LFQGQSPLTS (SEQ ID NO. 78) | 471 | 302 | 0.64 | Kd | 1.59 | 46.01 | 55.95 | 41.61 | - |

TABLE 2-continued

Neoantigens identified in mouse breast cancer cell line 4T1.2. (* Amino acids that differ from wildtype sequences are indicated in bolded font. The minimal epitope with the highest predicted affinity is underlined.)

| Mutation | MT-27/29-mer seq* | MT score | WT score | Fold change | H-2 allele | Normal VAF | Tumor VAF | RNA VAF | Gene FPK | ELI SPOT |
|---|---|---|---|---|---|---|---|---|---|---|
| Gen1. K707N | IPHNPRVAVKTTNNLVM KNSVCLERDS (SEQ ID NO. 79) | 543 | 306 | 0.56 | Kd | 0 | 76.62 | 87.78 | 3.01 | + |
| Gpld1. R829W | GRNQVVVAAGRSSWGA WLSGALHVYSFSS (SEQ ID NO. 80) | 1817 | 904 | 0.50 | Kd | 0 | 68.63 | 74.64 | 17.96 | − |
| Igsf9. S813R | DSVTKFKLQGSPVPRLRQ SLLWGEPARP (SEQ ID NO. 81) | 77 | 30 | 0.39 | Ld | 0 | 14.75 | 24.19 | 6.79 | − |
| Lta4h. V420I | GFLKAYVKKFSYQSITTD DWKSFLYSHFK (SEQ ID NO. 82) | 246 | 95 | 0.39 | Kd | 0 | 32.91 | 51.81 | 3.94 | − |
| Qars. E530D | FTLTALRRRGFPPDAINNF CARVGVTV (SEQ ID NO. 83) | 27 | 8 | 0.30 | Ld | 0.65 | 23.26 | 33.33 | 0.16 | +++ |

Additional constructs were created that did not integrate the mutant ubiquitin tag in the E0771 model system. E0771 polyepitope DNA vaccines with or without the Ub' tag were used to vaccinate C57BL/6 mice. Results from IFN-γ ELISpot assays demonstrated no statistically significant difference in the ability to induce neoantigen-specific immune responses (data not shown).

Figure 13A:
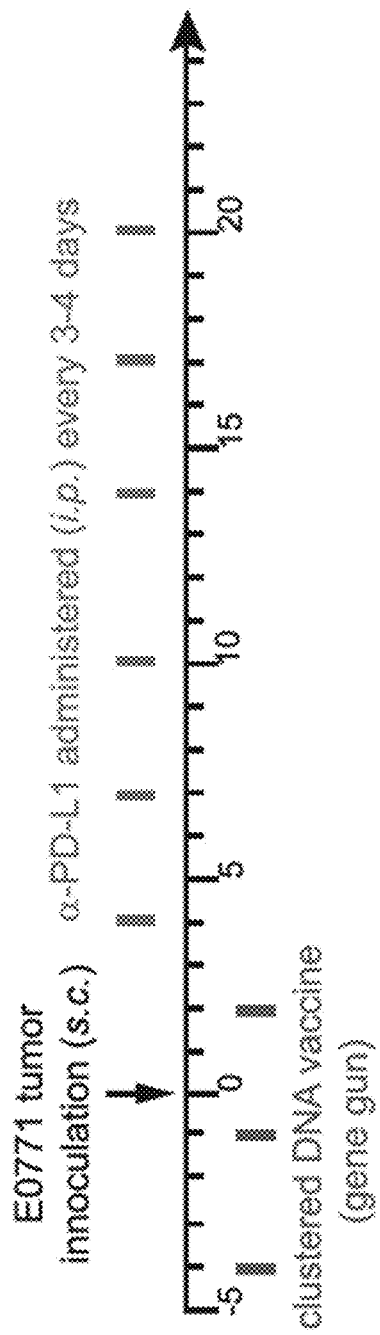
FIGS. 13A-13E. Polyepitope E0771 neoantigen DNA vaccines combined with anti-PD-L1 immunotherapy suppressed tumor growth in vivo.
Figure 13B:
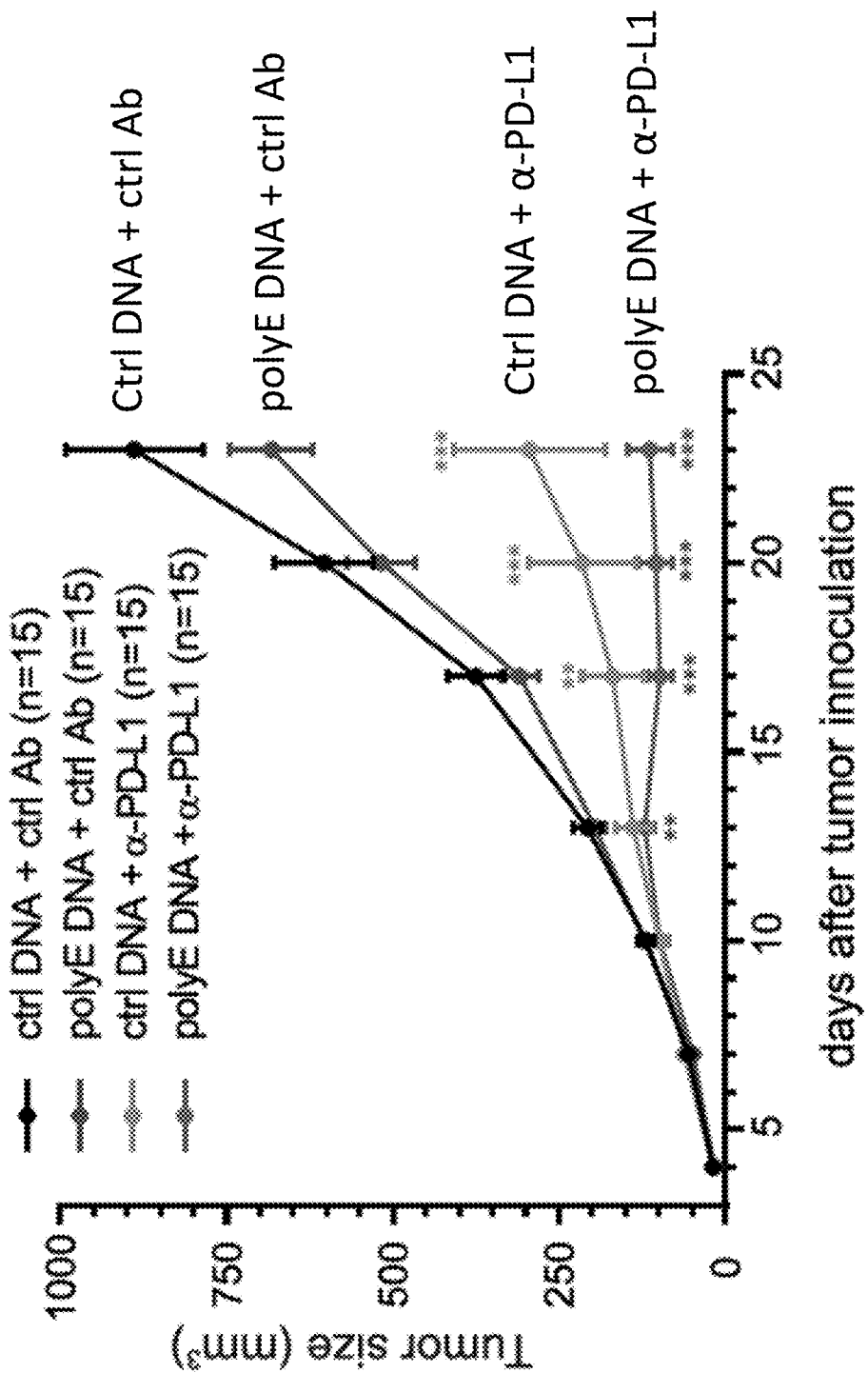
Figure 13C:
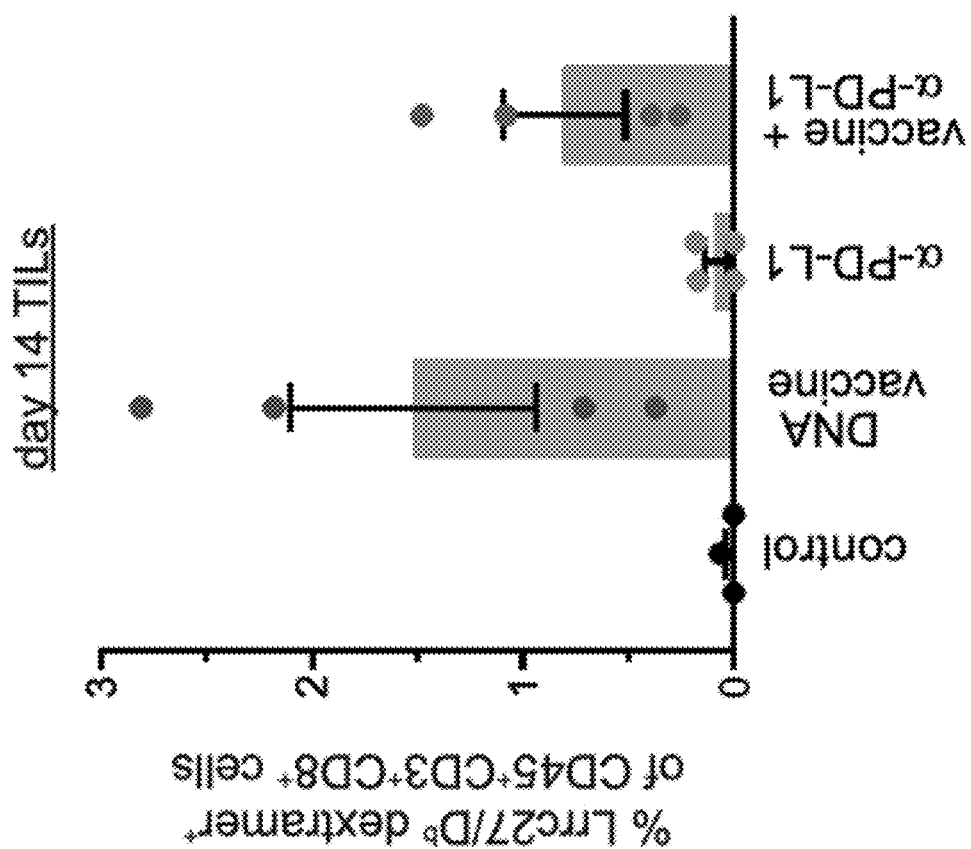
Figure 13D:
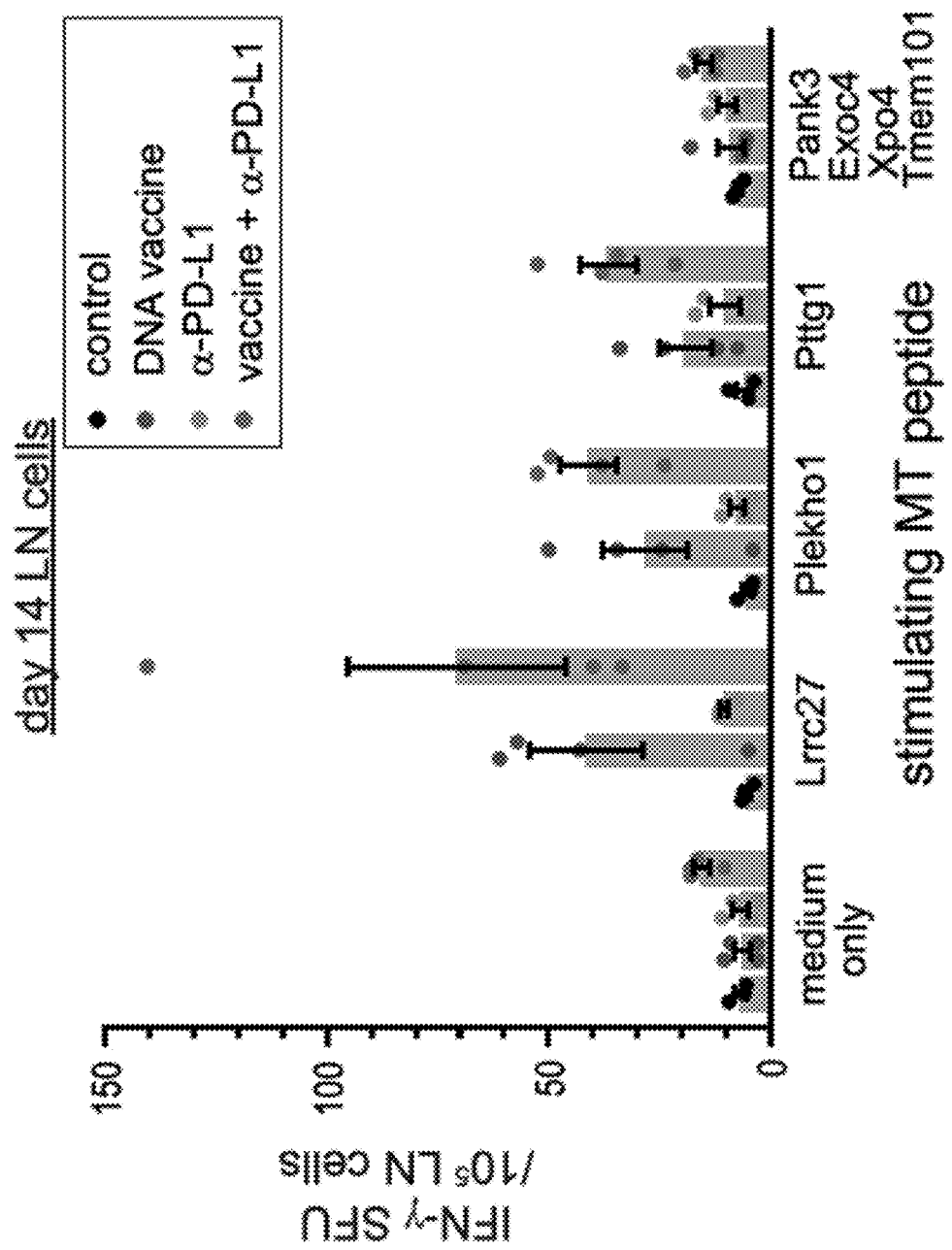
Figure 13E:
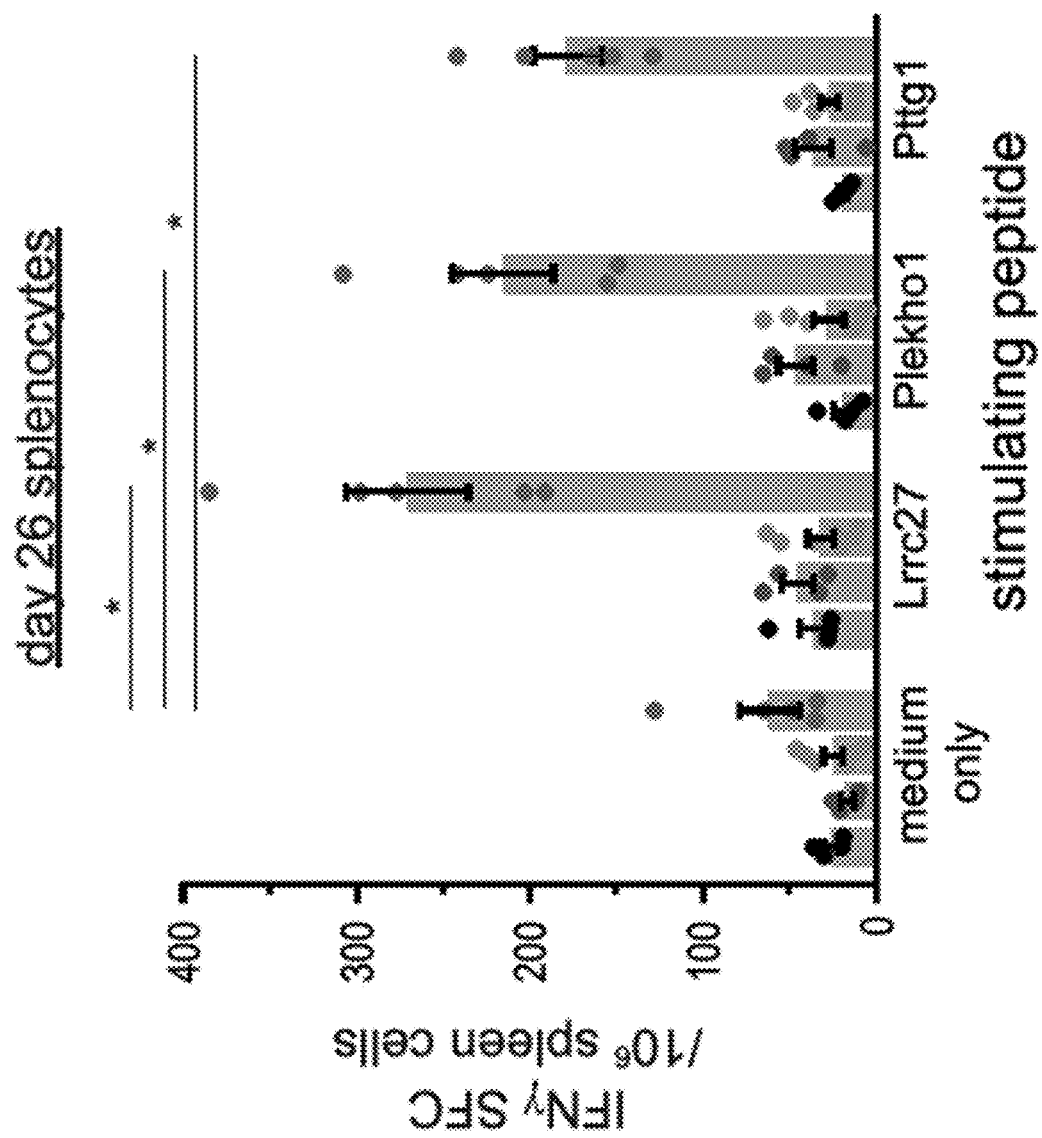

Optimized Polyepitope Neoantigen DNA Vaccines in Combination with Checkpoint Blockade Inhibit Tumor Growth in Preclinical Models Next investigated was whether antitumor immunity can be generated by polyepitope neoantigen DNA vaccines. Initially, polyepitope $Ub^{mut}$-E0771 DNA vaccine alone, in either prophylactic or therapeutic settings, had only a marginal impact on subcutaneously transplanted E0771 tumor growth (data not shown). However, when combined with anti-PD-L1 ICB therapy, the polyepitope $Ub^{mut}$-E0771 neoantigen DNA vaccine was able to enhance the antitumor response and suppress E0771 tumor growth for the duration of the experiment (FIGS. 13A & 13B). At day 14, robust neoantigen-specific T cell responses were detected in tumors (FIG. 13C) and tumor-draining lymph nodes (FIG. 13D) following treatment with neoantigen DNA vaccines alone, or neoantigen DNA vaccines plus anti-PD-L1 antibody. At day 26, neoantigen-specific T cell responses persisted only in mice treated with neoantigen DNA vaccines plus anti-PD-L1 antibody (FIG. 13E). In mice that received neoantigen DNA vaccines but not anti-PD-L1 antibody, neoantigen-specific T cell responses returned to baseline. These data suggest that in the setting of a tumor-bearing mouse, addition of anti-PD-L1 is required for persistent antitumor immunity following neoantigen DNA vaccine treatment.

Figure 18A:
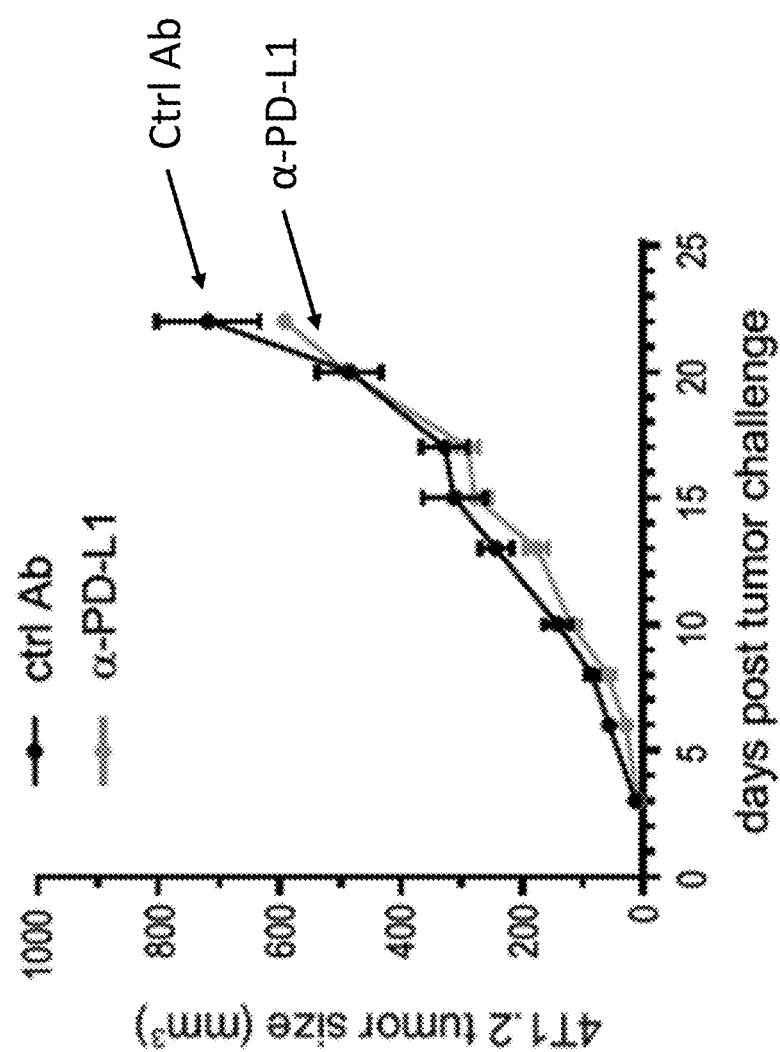
FIGS. 18A & 18B. $Ub^{mut}$-4T1.2 Polyepitope neoantigen DNA vaccine inhibited tumor growth in vivo.
Figure 18B:
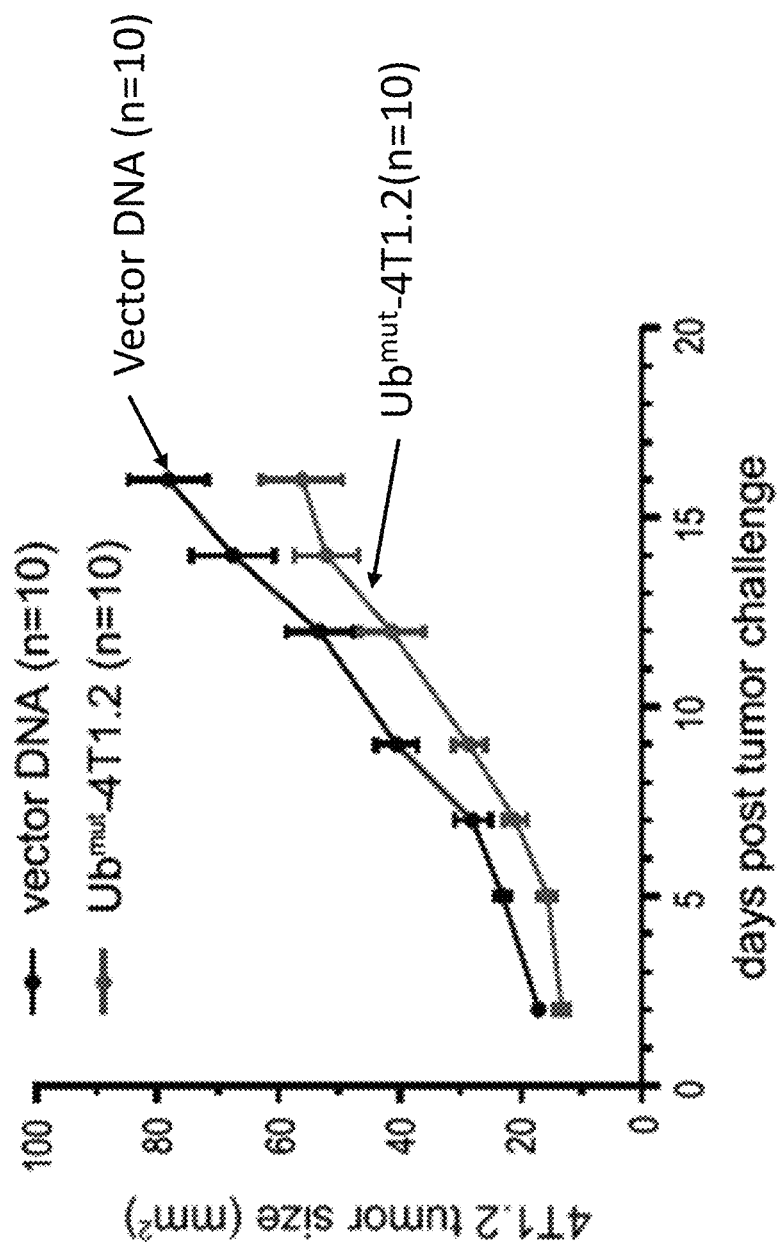

Unlike E0771, which is responsive to anti-PD-L1 treatment, 4T1.2 is resistant to anti-PD-L1 monotherapy (FIG. 18A). In a pilot study it was found that $Ub^{mut}$-4T1.2 polyepitope DNA vaccine alone was able to partially inhibit tumor growth in vivo (FIG. 18B). Further investigation is needed to understand the changes in immune system and whether ICB treatment will enhance the antitumor immunity induced by $Ub^{mut}$-4T1.2 polyepitope DNA vaccine.

Figure 14A:
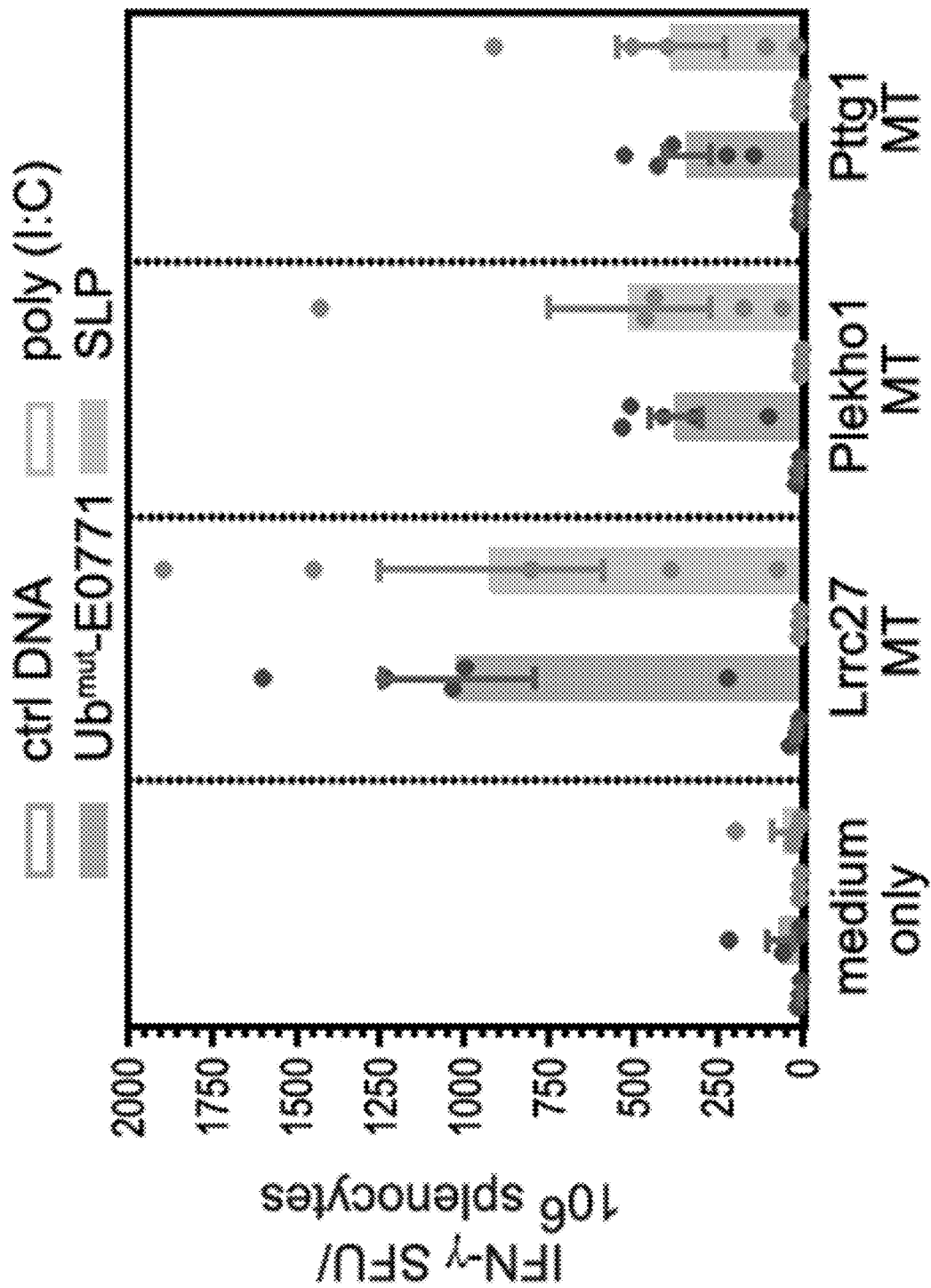
FIGS. 14A & 14B show that a polyepitope DNA vaccine generated similar magnitude of immune responses as synthetic long peptide vaccines.

Optimized Polyepitope DNA Vaccines Induce Similar Magnitude of Immune Responses as Synthetic Long Peptides The efficacy of polyepitope neoantigen DNA vaccines was compared with that of neoantigen SLP vaccines. Vaccine schedules were optimized for each platform by testing different doses and vaccination time points (DNA vaccine), or different doses, vaccination time points and molecular adjuvants (SLP vaccine) (data not shown). IFN-γ ELISpot assays performed on the same day indicated that the $Ub^{mut}$-E0771 polyepitope neoantigen DNA vaccine and the neoantigen SLP vaccine generated similar levels of T cell responses specific to the three neoantigens (FIG. 14A). Likewise, polyepitope $Ub^{mut}$-4T1.2 DNA vaccine and SLP vaccine generated similar levels of T cell responses specific to the four neoantigens (data not shown).

Figure 14B:
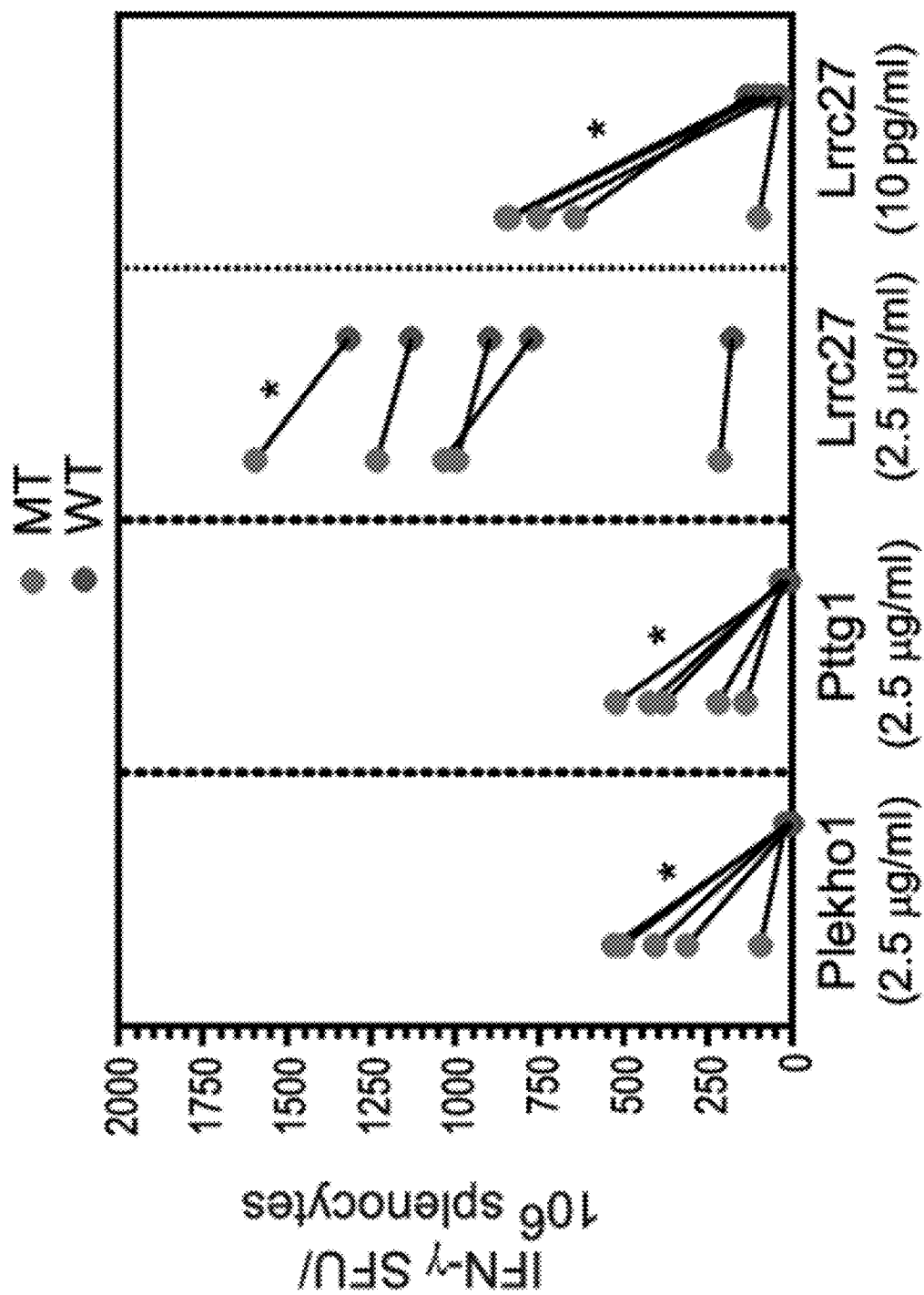
Figure 19A:
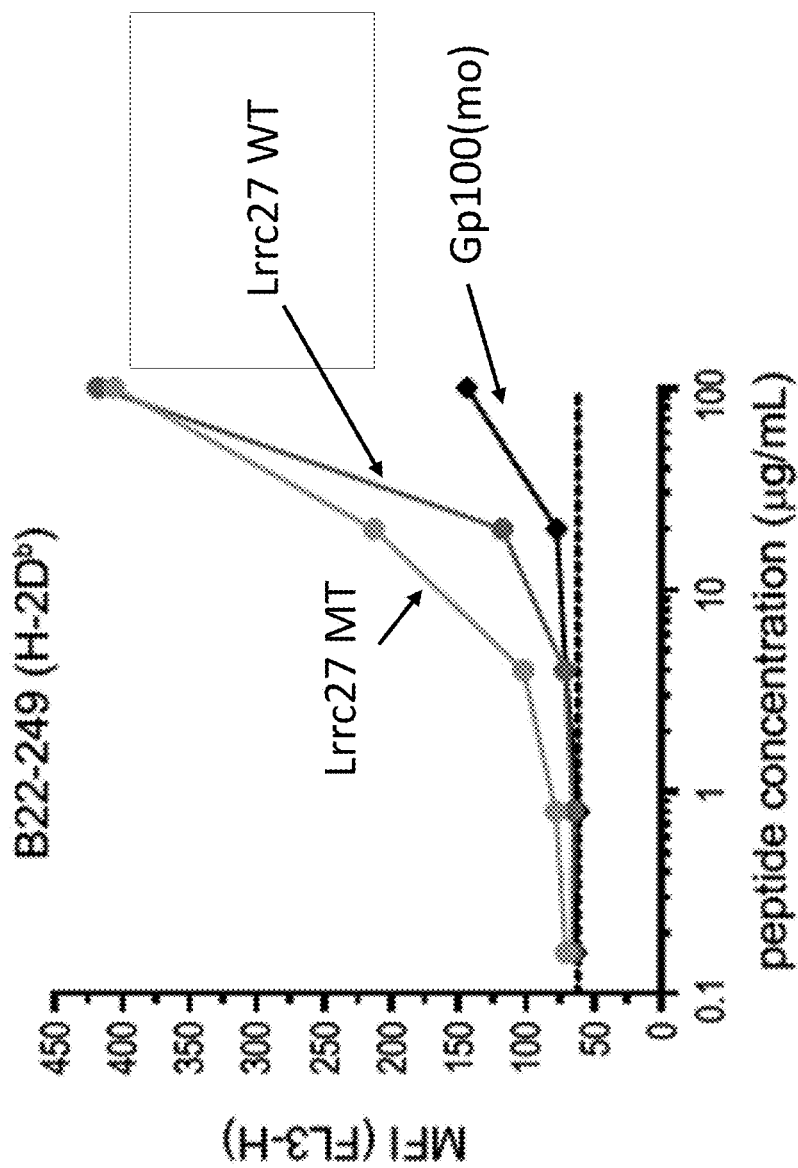
FIGS. 19A & 19B). Both MT and WT Lrrc27 peptides bind well to H-2Db.
Figure 19B:
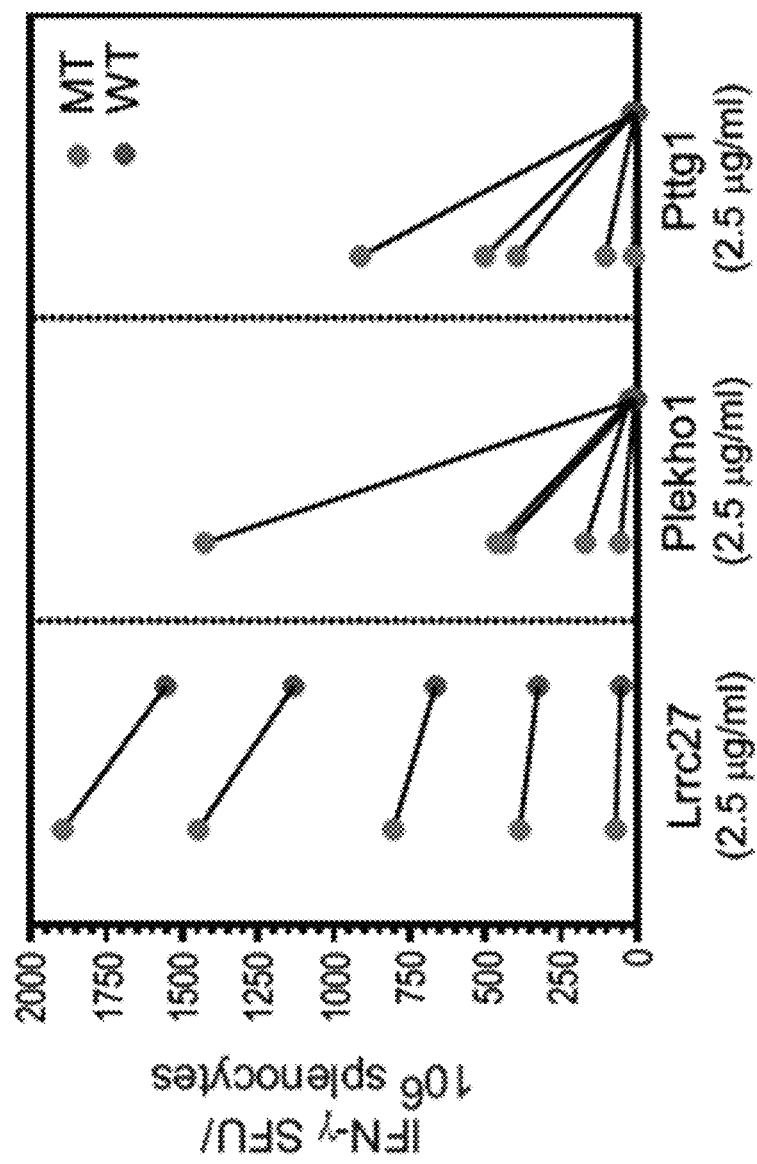

Specificity of the immune response was further investigated by means of cross-reactivity against corresponding germline (wildtype) Lrrc27, Plekho1, and Pttg1 epitopes over a range of concentrations. At physiologic concentrations, no reactivity was detected against all three WT epitopes (FIG. 14B and data not shown). Of note, one of the wild-type peptides (Lrrc27) was predicted to be a strong binder, with a predicted binding affinity of 408.48 nM to H-2D$^b$ [netMHC 4.0, http://www.cbs.dtu.dk/services/NetMHC]. Additional analysis revealed that both MT and WT Lrrc27 peptides bind equally well to H-2D$^b$ (FIG. 19A). At relatively high concentration, some cross-reactivity was observed against WT Lrrc27 peptide following vaccination with either polyepitope DNA or SLP vaccines (FIG. 14B and FIG. 19B). These data suggest that T cells induced by polyepitope $Ub^{mut}$-E0771 DNA vaccines preferably recognize MT neoantigens over WT counterparts when the density of peptide-MHC complexes is low. Such specificity to neoepitopes is critical as tumor cells typically only display relatively few neoantigen-MHC complexes.

Figure 15:
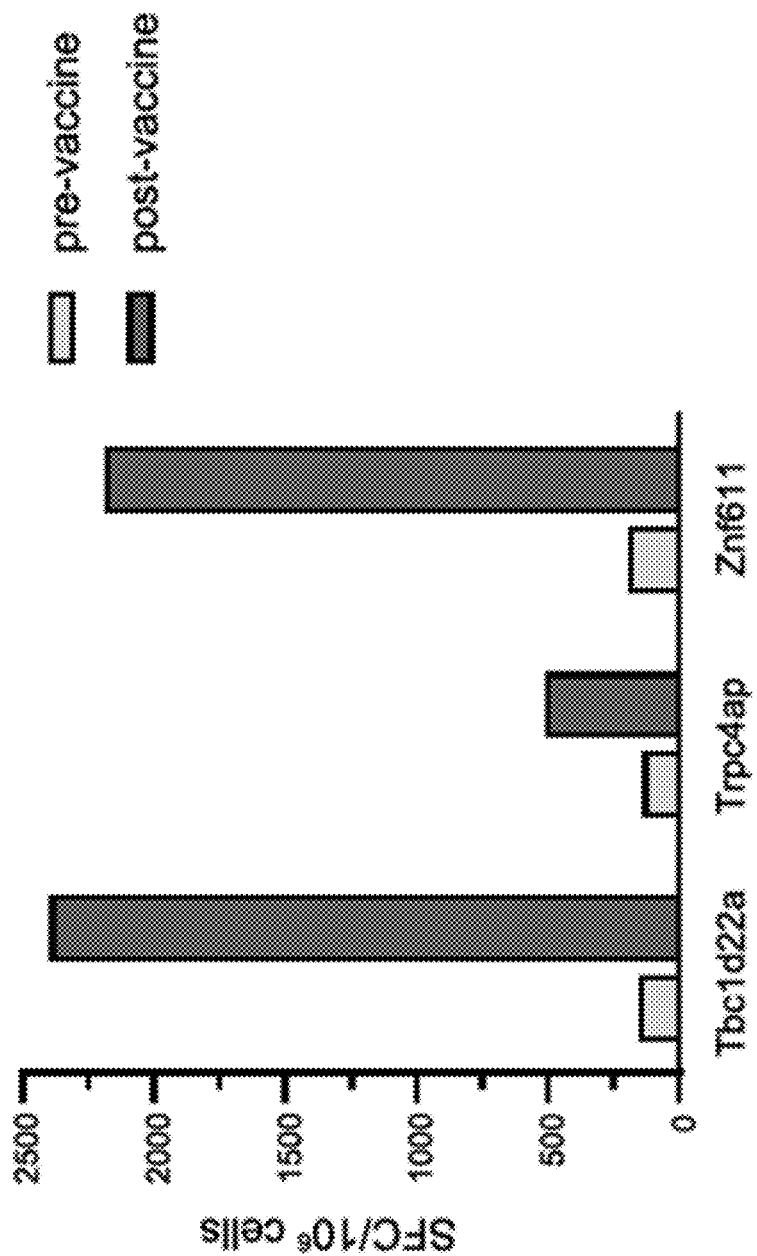
FIG. 15. An optimized polyepitope neoantigen DNA vaccine is capable of inducing neoantigen-specific T cell responses in a patient with metastatic pancreatic neuroendocrine cancer. PBMC from patient GTB16 were obtained before (pre-vaccine) and after (postvaccine) vaccination with an optimized polyepitope neoantigen DNA vaccine. PBMC were stimulated in vitro for 12 days with peptides corresponding to the indicated neoantigens and then an IFNγ ELISpot assay was performed. The number of spot forming cells (SFC) specific for each neoantigen is indicated. Nonspecific background counts, assessed by incubating cells without peptide during the ELISpot assay, were subtracted. The assays were repeated twice and similar results were obtained. Please note that the vaccine incorporated 13 neoantigens. A robust response was observed to 3/13 neoantigens. The other neoantigens did not induce a response.

An Optimized Polyepitope Neoantigen DNA Vaccine Induced Neoantigen-Specific T Cell Responses in a Patient with Metastatic Neuroendocrine Tumor Cancer patient GTB16 was treated with an optimized polyepitope neoantigen DNA vaccine. The pGTB16 vaccine was constructed as described for the preclinical studies and was manufactured in the GMP facility at WUSM. The DNA sequence of the pGTB16 construct and a list of targeted neoantigens can be found in the Sequence Listing and Table 3. IFNγ ELISpot assay performed after in vitro stimulation indicated that the polyepitope neoantigen DNA vaccine was able to induce T cell responses against select neoantigens. For this patient, 13 neoantigens were targeted by the DNA vaccine. Specific responses above background were demonstrated against three neoantigens (TBC1D22A:p.R437S, TRPC4AP:p.T63M, and ZNF611: p.D404G, FIG. 15).

against viral and conventional tumor antigens. Polyepitope proteins require additional intracellular processing in order to be loaded onto MHC molecules. Studies of peptide vaccination in incomplete Freund's adjuvant (IFA) showed that longer peptides (25-mers) in IFA can generate sustained CD8 T cell reactivity while shorter peptides (8-10-mers) corresponding to minimal epitopes induced only short-lived CD8 T cell responses. This may result from altered antigen processing with minimal epitopes, or the inclusion of both CD4 and CD8 epitopes in the longer epitopes. Since the goal

TABLE 3

Neoantigens identified in cancer patient GTB16. (* Amino acids that differ from wildtype sequences are indicated in bolded font. The minimal epitope with the highest predicted affinity is underlined.)

| Mutation | MT-25-mer seq* | MT score | WT score | Fold change | HLA allele |
|---|---|---|---|---|---|
| PDIA5:p.H416R | GDNFRETLKKKKRTLVMFYAPWCPH (SEQ ID NO. 84) | 5.5 | 8.7 | 1.58 | B57*01 |
| TBC1D22A:p.R437S | LLMREVPLRCTISLWDTYQSEPDGF (SEQ ID NO. 85) | 147.2 | 196 | 1.33 | A01*01 |
| GZF1:p.G253C | TRRLREQQKTAECDVGDYRCPQDQS (SEQ ID NO. 86) | 31 | 34 | 1.10 | B44*03 |
| TRPC4AP:p.T63M | LVRAVQFTETFLMERDKQSKWSGIP (SEQ ID NO. 87) | 147.2 | 196 | 1.33 | B44*03 |
| PCGF2:p.D128G | EVLEQEKGALSDGEIVSLSIEFYEG (SEQ ID NO. 88) | 66.9 | 308 | 4.60 | B44*03 |
| CLPB:p.R679H | PSPQAEKRLPKLHLEIIDKDSKTRR (SEQ ID NO. 89) | 162.5 | 264.8 | 1.63 | A32*01 |
| SIPAIL3:p.T687A | VKTDSTGTHSLYAMYQDYEIMFHVS (SEQ ID NO. 90) | 69.1 | 153.6 | 2.22 | A32*01 |
| TBC1D20:p.M90T | ALGAAALAVVKSTLEWAPKFQLQLF (SEQIDNO. 91) | 20.8 | 179.1 | 8.61 | A32*01 |
| SDHA:p.H407R | VTKEPIPVLPTVRYNMGGIPTNYKG (SEQ ID NO. 92) | 113 | 262 | 2.32 | C06*02 |
| CCDC6:p.R216H | NTLEQEQEALVNHLWKRMDKLEAEK (SEQ ID NO. 93) | 19.1 | 27.2 | 1.42 | B44*03 |
| LAMA5:p.R1026W | PSAYYEAALLQLWVTEACTYRPSAQ (SEQ ID NO. 94) | 6.9 | 3738.6 | 541.83 | B44*03 |
| SACS:p.S2711L | RFPLRNAEMAKVLEISSVPASDRMV (SEQ ID NO. 95) | 19.6 | 45.4 | 2.32 | B44*03 |
| ZNF611:p.D404G | HTGEKPYRCKVCGTAFTWHSQLARH (SEQ ID NO. 96) | 9 | 17 | 1.89 | A32*01 |

Discussion

Recombinant DNA vaccines are capable of generating potent immune responses and have progressed into clinical trials targeting infectious disease agents and cancer. DNA vaccines are stable, relatively easy to design and manufacture, and less expensive than synthetic long peptide, viral or cell-based vaccine platforms. More importantly, the molecular flexibility of the DNA vaccine platform allows genetic modification of encoded antigens, and/or incorporation of immune modulators to improve immunogenicity. As disclosed herein, polyepitope DNA vaccines encoding multiple cancer neoantigens were constructed and evaluated multiple parameters of the vaccine design including the length of neoepitopes, inclusion of spacers, and/or inclusion of a mutant ubiquitin construct to enhance antigen presentation.

The polyepitope approach has been studied previously and proved to be effective in priming T cell responses against viral and conventional tumor antigens. Polyepitope of neoantigen cancer vaccines is to generate a robust and long-lasting cancer-specific immune response, both short and long neoepitopes were evaluated in the DNA vaccines, with the understanding that maximizing presentation of long neoepitopes would be preferred. Accordingly as described herein, in some embodiments, long neoantigens contain neoantigen-specific CD4 helper T cell epitopes to induce a more balanced CD8/CD4 response. Recent studies demonstrate that CD4 T cell responses were induced by neoantigen vaccines even though neoantigen prioritization was based primarily on the binding affinity to MHC class I. Embodiments and data of the present disclosure confirm that long neoantigens are equally well processed and can induce robust neoantigen-specific CD8 and CD4 T cell responses in vivo.

Amino acids flanking minimal epitopes play an important role in TAP-binding and proteasomal cleavage. Researchers have used artificial linkers and furin cleavage sites to facilitate proteolytic cleavage and antigen presentation. Previous studies indicated a preference of natural flanking sequences in TAP-dependent antigen presentation. Some peptides are efficiently presented by MHC I molecules but are poorly transported by TAP as minimal epitopes. Research suggested that they can be more efficiently transported by TAP as larger fragments with natural flanking amino acids, which can be further trimmed in the endoplasmic reticulum (ER) and bind to MHC class I molecules. In embodiments of the present disclosure, it was found that epitopes flanked by natural sequences can be processed and presented effectively and adding a linker does not further enhance antigen presentation. In order to minimize the risk of junctional neoepitopes, a robust tool (pVACvector) was developed to assess for the presence of junctional epitopes. pVACvector starts with the list of prioritized neoantigens and uses the pVACseq software to predict the binding score for each possible junctional peptide. This information is used to order the neoantigen sequences in a way that minimizes junctional epitopes. Current version of the pVACtools suite, which contains pVACseq and pVACvector, is available at Github.

To enhance antigen presentation, integration of a mutant ubiquitin tag was explored as part of the polyepitope DNA vaccine to facilitate protein degradation and maximize antigen presentation. Early studies in the yeast *Saccharomyces cerevisiae* demonstrated that a monoubiquitin conjugate can function as protein degradation signal. Fusion of a ubiquitin molecule to a polyepitope DNA vaccine was able to enhance CTL priming and improve antitumor immune responses in an HPV-induced preclinical model. However, natural ubiquitin fusions are unstable and prone to deubiquitination under physiological conditions. The modification at the C-terminal portion of ubiquitin, replacing the glycine with a valine (G76V), metabolically stabilizes the fusion as revealed by pulse-chase analysis. This "uncleavable" $Ub^{mut}$ has been a useful tool in studying cell cycle and apoptosis, as wells as autophagy. The present disclosure demonstrates that the $Ub^{mut}$ tag does indeed improve antigen processing and presentation, which in turn results in an enhanced immune response in vitro.

Polyepitope DNA vaccines were created encoding neoantigens identified in mouse breast cancer models and tested these vaccines in vivo. Polyepitope DNA vaccines were able to induce robust T cell responses to some but not all neoantigens. This underscores the need for further improvement of neoantigen prediction algorithms. As disclosed herein, the finding that a polyepitope neoantigen DNA vaccine can induce robust T cell responses and antitumor immunity is consistent with a recent report. However, the polyepitope DNA vaccine designs evaluated here are distinct. Previously constructed polyepitope DNA vaccines encoding 33-mer neoantigens were separated by furin cleavage sites. In embodiments of the present disclosure, it is demonstrated that furin cleavage sites are not required for robust neoantigen presentation, and the software tool pVACvector is leveraged to optimize the order of neoantigens so that the risk of introducing junctional epitopes is minimized. In addition, the $Ub^{mut}$ tag was integrated into the constructs, which clearly improved antigen processing and presentation, and in some embodiments improved the downstream immune responses. Of note, the optimized polyepitope vaccine is not superior for every neoantigen/model tested. For instance, a side-by-side comparison of polyepitope DNA vaccines with or without the $Ub^{mut}$ tag targeting the same neoantigens identified in E0771 showed no statistically significant difference in magnitude of neoantigen-specific responses. Some neoantigens are efficiently processed and may not require targeting to the ubiquitin pathway for presentation, while others are less efficiently processed and benefit from targeting to the ubiquitin pathway.

In some embodiments, neoantigen DNA vaccines alone were not able to protect animals from transplanted E0771 and 4T1.2 tumors in spite of the ability to generate neoantigen-specific T cell responses. In some embodiments disclosed herein, combinatorial immunotherapy of neoantigen DNA vaccine plus anti-PD-L1 checkpoint blockade is capable of suppressing E0771 tumor growth. Detailed study of the mechanism(s) of the antitumor immunity rendered by the optimized polyepitope neoantigen DNA vaccine+/−ICB immuno-therapy is ongoing. Research into the cellular and molecular changes occurring in the tumor microenvironment following combination therapy with ICB and neoantigen DNA vaccine is currently underway in novel genetic models. Preliminary data suggest that tumor growth inhibition by combination immunotherapy is associated with sustained neoantigen-specific T cell responses and CD8 T cell infiltration into the tumor (FIG. 13C-13E). The recent clinical success of ICB in treating various types of cancer has pushed it towards the forefront of cancer therapy. a randomized phase 1 clinical trial that tests the efficacy of a polyepitope neoantigen DNA vaccine+/— anti-PD-L1 in patients with triple negative breast cancer (NCT03199040) has been initiated, as disclosed herein. This trial represents unique bench-to-bedside-to-bench opportunities to enhance the efficacy of neoantigen vaccines and checkpoint blockade therapy.

Finally, a patient with metastatic neuroendocrine tumor was treated with a polyepitope neoantigen DNA vaccine. This is the first report of the use of a neoantigen DNA vaccine in humans. The tumor of this patient was refractory to standard of care treatment and showed evidence of ongoing progression at the time when the vaccination started on a compassionate use basis. Embodiments and data of the present disclosure demonstrates that polyepitope neoantigen DNA vaccines are capable of inducing neoantigen-specific T cell responses. Depending on the embodiment, successful clinical translation of polyepitope neoantigen DNA vaccines may depend on refinement of neoantigen prediction algorithms, combination therapies targeting the tumor microenvironment, and an improved ability to assess the antitumor potential of neoantigen-specific T cells. Neoantigen-specific T cell responses were observed for 3/13 neoantigens included in the vaccine, highlighting the need to further refine current neoantigen prediction algorithms. In addition, neoantigen-specific T cells may not be effective in mediating antitumor immunity if these T cells are suppressed in the tumor microenvironment. Future use of innovative technologies such as CyTOF, IMC, and CODEX, will enable investigation of the phenotype and function of neoantigen-specific T cells in the tumor, and the impact of combination therapy on the tumor microenvironment. These technologies will allow a better understanding of the antitumor potential of neoantigen-specific T cells.

CONCLUSIONS

A polyepitope DNA vaccine design was optimized to encode multiple neoantigens. Tumor/normal whole exome sequencing and RNA sequencing were used to identify and prioritize neoantigens in the E0771 and 4T1.2 preclinical breast cancer models, as well as a patient with metastatic pancreatic neuroendocrine tumor. E0771 and 4T1.2-specific polyepitope neoantigen DNA vaccines were able to induce robust immune responses and inhibit tumor growth when combined with anti-PD-L1 checkpoint blockade immunotherapy. Similarly, neoantigen-specific immune responses were detected after vaccination in a patient with metastatic neuroendocrine tumor. The results provide strong evidence to support clinical translation of a polyepitope neoantigen DNA vaccine strategy. The polyepitope neoantigen DNA vaccine platform are currently being evaluated in phase 1 clinical trials in breast and pancreas cancer (NCT03199040 and NCT03122106).

All methods described herein are performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member is referred to and claimed individually or in any combination with other members of the group or other elements found herein. One or more members of a group are included in, or deleted from, a group for reasons of convenience or patentability. When any such inclusion or deletion occurs, the specification is herein deemed to contain the group as modified thus fulfilling the written description of all Markush groups used in the appended claims.

All of the compositions and/or methods disclosed and claimed herein may be made and/or executed without undue experimentation in light of the present disclosure. While the compositions and methods of this disclosure have been described in terms of the embodiments included herein, it will be apparent to those of ordinary skill in the art that variations may be applied to the compositions and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A fusion protein comprising at least one triple negative breast cancer (TNBC)-associated neoantigen epitope joined to a mutant ubiquitin protein, wherein the at least one TNBC-associated neoantigen epitope is LRRC27, and wherein the mutant ubiquitin protein is selected from SEQ ID NO: 1, SEQ ID NO: 1 comprising substitution of a leucine at position 76, and SEQ ID NO: 1 comprising substitution of an isoleucine at position 76.

2. The fusion protein of claim 1, further comprising at least one additional TNBC-associated neoantigen epitope.

3. A nucleic acid molecule encoding a fusion protein comprising at least one TNBC-associated neoantigen epitope joined to a mutant ubiquitin protein, wherein the at least one TNBC-associated neoantigen epitope is LRRC27, and wherein the mutant ubiquitin protein is selected from SEQ ID NO: 1, SEQ ID NO: 1 comprising substitution of a leucine at position 76, and SEQ ID NO: 1 comprising substitution of an isoleucine at position 76.

4. A method of treating Triple Negative Breast Cancer (TNBC) in an individual, the method comprising administering a therapeutically effective amount of a fusion protein, comprising at least one TNBC-associated neoantigen epitope joined to a mutant ubiquitin protein, wherein the at least one TNBC-associated neoantigen epitope is LRRC27, and wherein the mutant ubiquitin protein is selected from SEQ ID NO: 1, SEQ ID NO: 1 comprising substitution of a leucine at position 76, and SEQ ID NO: 1 comprising substitution of an isoleucine at position 76.

* * * * *

SEQUENCE LISTING

```
Sequence total quantity: 96
SEQ ID NO: 1            moltype = AA  length = 76
FEATURE                 Location/Qualifiers
source                  1..76
                        mol_type = protein
                        organism = Synthetic construct
SEQUENCE: 1
MQIFVKTLTG KTITLEVEPS DTIENVKAKI QDKEGIPPDQ QRLIFAGKQL EDGRTLSDYN   60
IQKESTLHLV LRLRGV                                                  76

SEQ ID NO: 2            moltype = AA  length = 16
FEATURE                 Location/Qualifiers
source                  1..16
                        mol_type = protein
                        organism = Homo sapiens
SEQUENCE: 2
HQTGDFLCPV CSHCYP                                                  16

SEQ ID NO: 3            moltype = AA  length = 16
FEATURE                 Location/Qualifiers
source                  1..16
                        mol_type = protein
                        organism = Homo sapiens
SEQUENCE: 3
DFLCPVCSHC YPNLAA                                                  16

SEQ ID NO: 4            moltype = AA  length = 16
FEATURE                 Location/Qualifiers
source                  1..16
                        mol_type = protein
                        organism = Homo sapiens
SEQUENCE: 4
VCSHCYPNLA AYRNHL                                                  16

SEQ ID NO: 5            moltype = AA  length = 16
FEATURE                 Location/Qualifiers
source                  1..16
                        mol_type = protein
                        organism = Homo sapiens
SEQUENCE: 5
PREDEKDGQA YKSVSR                                                  16
```

```
SEQ ID NO: 6              moltype = AA  length = 16
FEATURE                   Location/Qualifiers
source                    1..16
                          mol_type = protein
                          organism = Homo sapiens
SEQUENCE: 6
EKDGQAYKSV SRSEME                                                                16

SEQ ID NO: 7              moltype = AA  length = 16
FEATURE                   Location/Qualifiers
source                    1..16
                          mol_type = protein
                          organism = Homo sapiens
SEQUENCE: 7
AYKSVSRSEM EADIKA                                                                16

SEQ ID NO: 8              moltype = AA  length = 16
FEATURE                   Location/Qualifiers
source                    1..16
                          mol_type = protein
                          organism = Homo sapiens
SEQUENCE: 8
KGANQHNMPN LIYTMM                                                                16

SEQ ID NO: 9              moltype = AA  length = 16
FEATURE                   Location/Qualifiers
source                    1..16
                          mol_type = protein
                          organism = Homo sapiens
SEQUENCE: 9
HNMPNLIYTM MELRKC                                                                16

SEQ ID NO: 10             moltype = AA  length = 16
FEATURE                   Location/Qualifiers
source                    1..16
                          mol_type = protein
                          organism = Homo sapiens
SEQUENCE: 10
NLIYTMMELR KCCNHP                                                                16

SEQ ID NO: 11             moltype = AA  length = 16
FEATURE                   Location/Qualifiers
source                    1..16
                          mol_type = protein
                          organism = Homo sapiens
SEQUENCE: 11
FGELFEKAKQ NNKNRK                                                                16

SEQ ID NO: 12             moltype = AA  length = 16
FEATURE                   Location/Qualifiers
source                    1..16
                          mol_type = protein
                          organism = Homo sapiens
SEQUENCE: 12
EKAKQNNKNR KTSNGD                                                                16

SEQ ID NO: 13             moltype = AA  length = 16
FEATURE                   Location/Qualifiers
source                    1..16
                          mol_type = protein
                          organism = Homo sapiens
SEQUENCE: 13
QNNKNRKTSN GDDSLF                                                                16

SEQ ID NO: 14             moltype = AA  length = 16
FEATURE                   Location/Qualifiers
source                    1..16
                          mol_type = protein
                          organism = Homo sapiens
SEQUENCE: 14
FVPFRQFQNA PKAALA                                                                16

SEQ ID NO: 15             moltype = AA  length = 16
FEATURE                   Location/Qualifiers
source                    1..16
                          mol_type = protein
                          organism = Homo sapiens
SEQUENCE: 15
```

-continued

```
QFQNAPKAAL AQCVLA                                                          16

SEQ ID NO: 16           moltype = AA   length = 15
FEATURE                 Location/Qualifiers
source                  1..15
                        mol_type = protein
                        organism = Homo sapiens SEQUENCE: 16
PKAALAQCVL AEIPQ                                                           15

SEQ ID NO: 17           moltype = AA   length = 16
FEATURE                 Location/Qualifiers
source                  1..16
                        mol_type = protein
                        organism = Homo sapiens SEQUENCE: 17
PVERIVSRDI ARCYER                                                          16

SEQ ID NO: 18           moltype = AA   length = 16
FEATURE                 Location/Qualifiers
source                  1..16
                        mol_type = protein
                        organism = Homo sapiens SEQUENCE: 18
VSRDIARCYE RIPIPC                                                          16

SEQ ID NO: 19           moltype = AA   length = 15
FEATURE                 Location/Qualifiers
source                  1..15
                        mol_type = protein
                        organism = Homo sapiens SEQUENCE: 19
ARCYERIPIP CVNAV                                                           15

SEQ ID NO: 20           moltype = AA   length = 16
FEATURE                 Location/Qualifiers
source                  1..16
                        mol_type = protein
                        organism = Homo sapiens SEQUENCE: 20
CASSLERGGG NYEQYF                                                          16

SEQ ID NO: 21           moltype = AA   length = 13
FEATURE                 Location/Qualifiers
source                  1..13
                        mol_type = protein
                        organism = Homo sapiens SEQUENCE: 21
CASNNQVGDE QYF                                                             13

SEQ ID NO: 22           moltype = AA   length = 17
FEATURE                 Location/Qualifiers
source                  1..17
                        mol_type = protein
                        organism = Homo sapiens SEQUENCE: 22
CASSQENWGS SYNEQFF                                                         17

SEQ ID NO: 23           moltype = AA   length = 14
FEATURE                 Location/Qualifiers
source                  1..14
                        mol_type = protein
                        organism = Homo sapiens SEQUENCE: 23
CSVARDTNSY EQYF                                                            14

SEQ ID NO: 24           moltype = AA   length = 16
FEATURE                 Location/Qualifiers
source                  1..16
                        mol_type = protein
                        organism = Homo sapiens SEQUENCE: 24
CASSTNGQHS GNTIYF                                                          16

SEQ ID NO: 25           moltype = AA   length = 16
FEATURE                 Location/Qualifiers
source                  1..16
                        mol_type = protein
                        organism = Homo sapiens
```

```
SEQUENCE: 25
EKIESQRIIS GRMSGY                                                        16

SEQ ID NO: 26           moltype = AA  length = 16
FEATURE                 Location/Qualifiers
source                  1..16
                        mol_type = protein
                        organism = Homo sapiens
SEQUENCE: 26
QRIISGRMSG YISEAS                                                        16

SEQ ID NO: 27           moltype = AA  length = 15
FEATURE                 Location/Qualifiers
source                  1..15
                        mol_type = protein
                        organism = Homo sapiens
SEQUENCE: 27
GRMSGYISEA SGESQ                                                         15

SEQ ID NO: 28           moltype = AA  length = 16
FEATURE                 Location/Qualifiers
source                  1..16
                        mol_type = protein
                        organism = Homo sapiens
SEQUENCE: 28
DEELYSRQLY VLCSPA                                                        16

SEQ ID NO: 29           moltype = AA  length = 16
FEATURE                 Location/Qualifiers
source                  1..16
                        mol_type = protein
                        organism = Homo sapiens
SEQUENCE: 29
SRQLYVLCSP AMQRIQ                                                        16

SEQ ID NO: 30           moltype = AA  length = 15
FEATURE                 Location/Qualifiers
source                  1..15
                        mol_type = protein
                        organism = Homo sapiens
SEQUENCE: 30
VLCSPAMQRI QGARV                                                         15

SEQ ID NO: 31           moltype = AA  length = 16
FEATURE                 Location/Qualifiers
source                  1..16
                        mol_type = protein
                        organism = Homo sapiens
SEQUENCE: 31
DCECLCDAVA AYTQAC                                                        16

SEQ ID NO: 32           moltype = AA  length = 16
FEATURE                 Location/Qualifiers
source                  1..16
                        mol_type = protein
                        organism = Homo sapiens
SEQUENCE: 32
CDAVAAYTQA CLDKGV                                                        16

SEQ ID NO: 33           moltype = AA  length = 15
FEATURE                 Location/Qualifiers
source                  1..15
                        mol_type = protein
                        organism = Homo sapiens
SEQUENCE: 33
AYTQACLDKG VCVDW                                                         15

SEQ ID NO: 34           moltype = AA  length = 16
FEATURE                 Location/Qualifiers
source                  1..16
                        mol_type = protein
                        organism = Homo sapiens
SEQUENCE: 34
KKTGSQTRRT LKLQPQ                                                        16

SEQ ID NO: 35           moltype = AA  length = 16
FEATURE                 Location/Qualifiers
source                  1..16
                        mol_type = protein
```

```
                        organism = Homo sapiens
SEQUENCE: 35
QTRRTLKLQP QQLQQN                                                       16

SEQ ID NO: 36           moltype = AA   length = 15
FEATURE                 Location/Qualifiers
source                  1..15
                        mol_type = protein
                        organism = Homo sapiens
SEQUENCE: 36
LKLQPQQLQQ NLPKG                                                        15

SEQ ID NO: 37           moltype = DNA  length = 228
FEATURE                 Location/Qualifiers
source                  1..228
                        mol_type = other DNA
                        organism = Synthetic construct
SEQUENCE: 37
atgcagatct tgtgaaaac  cttaactggt aagaccatca ccctggaggt cgagcccagt        60
gacaccattg agaatgtcaa ggcaaagatc caggacaagg agggcatccc ccctgaccag       120
cagaggctga tctttgcagg caagcagctg gaagatggcc gcaccctgtc agactacaac       180
atccagaaag agtccaccct gcacctggtc cttcgcctga gaggtgtc                    228

SEQ ID NO: 38           moltype = AA   length = 76
FEATURE                 Location/Qualifiers
source                  1..76
                        mol_type = protein
                        organism = Synthetic construct
SEQUENCE: 38
MQIFVKTLTG KTITLEVEPS DTIENVKAKI QDKEGIPPDQ QRLIFAGKQL EDGRTLSDYN        60
IQKESTLHLV LRLRGV                                                       76

SEQ ID NO: 39           moltype = DNA  length = 516
FEATURE                 Location/Qualifiers
source                  1..516
                        mol_type = other DNA
                        organism = Synthetic construct
SEQUENCE: 39
ggcatcctgg ccagaaacct ggtgcccatg gtggccaccg tgcagggcca gaacctgaag        60
ggccccgtgt tcatgtgcct gggcggcctg ctgaccatgg tggccggcgc cgtgtggctg       120
gtgctgtgct gctacgtgct ggaggagacc agcgtgatgc tggccaagag acccctgatc       180
gtggtgaccc acacctacct ggagcccggc cccgtgaccg cccaggtggt gctgcaggcc       240
gccatccaga acgccggcct gtgcaccctg gtggccatgc tgctggagga gaccatcttc       300
agcagcgcct tcaccatcac cgaccaggtg cccttcagcg tgcagctgag agccctggac       360
gcctgggact cggcagcgt gggcggcgtg ttcaccagcg tgggcaaggc cgtgcaccag        420
agcccccctga ccggcggcat cctgggcttc gtgttcaccc tgaccgtgcc cagcgagaga      480
caattgtacc catacgatgt tccagattac gcttag                                 516

SEQ ID NO: 40           moltype = AA   length = 171
FEATURE                 Location/Qualifiers
source                  1..171
                        mol_type = protein
                        organism = Synthetic construct
SEQUENCE: 40
GILARNLVPM VATVQGQNLK GPVFMCLGGL LTMVAGAVWL VLCCYVLEET SVMLAKRPLI        60
VVTHTYLEPG PVTAQVVLQA AIQNAGLCTL VAMLLEETIF SSAFTITDQV PFSVQLRALD       120
AWDFGSVGGV FTSVGKAVHQ SPLTGGILGF VFTLTVPSER QLYPYDVPDY A                171

SEQ ID NO: 41           moltype = DNA  length = 825
FEATURE                 Location/Qualifiers
source                  1..825
                        mol_type = other DNA
                        organism = Synthetic construct
SEQUENCE: 41
atgcagctgg cctctaccta cacagcttac atcgtgggct acgtgcacta cggagattgg        60
ctgaagaacg agaagatcaa cagggtggtg ttcgtgtgga ctttctgcgg ggtgaacacc       120
ctgtctatgc gccttggga gaagccgac aagggcgcca gctacacacc acaggctctg        180
aagaagttcc ccgccgacct ggattttgct agacagtact acgtgatgct gtacaacacc       240
gccgacgagc tgctgttcaa gggaatcctg cccaacctgc ctagcgccta ccagaacacc       300
gtgcacgcta acaggatgac agattctgtg atcagactgc tgagcgccct gctgcgggtg       360
tccgaggtgg agtctaggc tagagtgggc aagtgtttta cgccccagc tctgcccaag        420
gcctccagaa aggctctggg caccctggga aaggagctgt tcatgtactt tggacaccgg       480
gccctgcgca tccacttcgg aatgaagctg tttgaggaca caaacctgtg cgccatcaac       540
gctaagcggg tgaccatcat gcctaaggac gacgtagcg tgacaaaggc cctgcagcac        600
ctgtctcact acttcgaggg cgtgctgaag tgtctggtga gcatgccact gtgggctaag       660
cacatgtccg atgagcagat ccagggcttc gtgaggagc cctttgagaa gcctgtgatg       720
atctctatgg gaaacgagaa cgtggtggag atcaagggcc tggagatcca gggaaccgac       780
cctgtgagcg ccgtgaccct gagcctgctg gaccccgaga cctga                       825
```

```
SEQ ID NO: 42            moltype = AA   length = 274
FEATURE                  Location/Qualifiers
source                   1..274
                         mol_type = protein
                         organism = Synthetic construct
SEQUENCE: 42
MQLASTYTAY IVGYVHYGDW LKNEKINRVV FVWNFLRVNT LSMRPWEKPD KGASYTPQAL    60
KKFPADLDFA RQYYVMLYNT ADELLFKGIL PNLPSAYQNT VHANRMTDSV IRLLSALLRV   120
SEVESRARVG KVFNAPALPK ASRKALGTLG KELFMYFGHR ALRIHFGMKL FEDTNLCAIN   180
AKRVTIMPKD DVSVTKALQH LSHYFEGVLK CLVSMPLWAK HMSDEQIQGF VEEPFEKPVM   240
ISMGNENVVE IKGLEIQGTD PVSAVTLSLL DPET                              274

SEQ ID NO: 43            moltype = DNA   length = 1270
FEATURE                  Location/Qualifiers
source                   1..1270
                         mol_type = other DNA
                         organism = Synthetic construct
SEQUENCE: 43
atgatttgcg atctgcttca gctgttattg gcgcacgcc ttgaatctga ttaaattagt     60
acgcggccgc aaaccgctgt cttggcttag ccgcgcccg cgtccgaccg gccctccagc    120
gtcccgctta gcgagtaaga gccacagcag cgttaaacgc ctgcgtaaaa tgcatcatgc   180
cgccgtggga caggataaac cggtcttat ggaggaagtc cccttccgc acacagcccg     240
cattccggga ctccggtcat tggatgaagt ccaaccgcag cagctgccag caacagatcc   300
aaaactgctg aaattgatcc gtaaggctga aaaagccgaa cgtgaatttc gtaaaaaagc   360
ggcgctgttg gaaccccac ggggtaaaat tcaggccaaa aaatggagcc tggtaccgtt    420
ttctattccg gttttcgata ttttgcaaga ttgcgcgcc ttgatcccgc acaatccacg    480
cgtagcggtc aaaacgacga acaacctcgt tatgaaaaac agtgtttgcc tggagcgcga   540
ttcgtttacc ctgacggccc tgcgtcgccg tggttttccg cctgacgcca tcaacaactt   600
ctgcgcccgg gtaggcgtaa ccgtagctgc tttaatggcg atggagctct ccgcgtctg    660
tttggtgtgg gttacaggaa ttatcaatca ccctttgctg ttcccgcgtg aaaacgcgac   720
ccaccactct aagatggact agaaaaacc gaactacatc gtgccagatt gtatgccggt    780
tgtttatgat aagctgccac aaccgccgac tcatcaccac ggtcgtaacc aggttgtagt   840
ggctgcgggt cgtagtagct ggggtgcttg gctgagtggc gcgctccacg tgtatagctt   900
ttcaagtcat catctgcgcg ttgaaaaact gcaactcgag agcgagctga acgaaagccg   960
tacggaatgc atcaccgcca cgtcgcagat gacggcccac caccatgatt ctgttaccaa  1020
gttcaaactg caaggctcgc cggtcccgcg ccttcgtcag tccttattgt ggggtgaacc  1080
ggcacgtccg ccgcatcata ttaacgccga ggaatcggaa attcgctaca gtacctgaa   1140
gcgcgcggta atgaagagca ttggctgggt taccacacag agtccagtta gtatcagcta  1200
cttttcccgt gcggcgtacg cggggttgtt taccccgtta taccgtccgg gcctgtcatg  1260
ccagatttaa                                                        1270

SEQ ID NO: 44            moltype = AA   length = 422
FEATURE                  Location/Qualifiers
source                   1..422
                         mol_type = protein
                         organism = Synthetic construct
SEQUENCE: 44
MFAICFSCLL AHALNLIKLV RGRKPLSWLS RAPRPTGPPA SRLASKSHSS VKRLRKMHHA    60
AVGQDKPVFM EEVPLPHTAR IPGLRSLDEV QPQQLPATDP KLLKLIRKAE KAEREFRKKA   120
ALLETPRGKI QAKKWSLVPF SIPVFDILQD CAALIPHNPR VAVKTTNNLV MKNSVCLERD   180
SFTLTALRRR GFPPDAINNF CARVGVTVAA LMAMELFRVC LVVVTGIINH PLLFPRENAT   240
HHSKMDLEKP NYIVPDCMPV VYDKLPQPPT HHHGRNQVVV AAGRSSWGAW LSGALHVYSF   300
SSHHLRVEKL QLESELNESR TECITATSQM TAHHHDSVTK FKLQGSPVPR LRQSLLWGEP   360
ARPPHHINAE ESEIRYSTWK RAVMKSIGWV TTQSPVSISY FSRAAYAGLF TPLYRPGLSC   420
QI                                                                 422

SEQ ID NO: 45            moltype = DNA   length = 1068
FEATURE                  Location/Qualifiers
source                   1..1068
                         mol_type = other DNA
                         organism = Synthetic construct
SEQUENCE: 45
ggcgacaact ttcgtgagac cctgaaaaag aagaaacgca cgcttgtaat gttttacgca    60
ccatggtgcc cacaccatca tctgttaatg cgcgaagtgc cactgcgttg tacgatcagc   120
ctttgggaca cctaccagag cgaaccagac ggtttccacc acactcgtcg cctgcgcgaa   180
caacagaaaa ccgcagaatg tgatgtgggc gattaccgtt gtccgcagga tcagtctgcg   240
gcgttgctgg tgcgcgctgt gcagttcaca gaaacctttc tgatggaacg cgataagcag   300
agtaaatggt ctggaatccc tgcggcgtac gaagttttag aacaggagaa aggtgcactg   360
tctgatggtg aaattgtgag tctgtctatt gaatttacg aaggccatca ctgcccgtca    420
cctcaggcag agaaacgctt gccgaaatta cacttagaaa ttatcgataa ggactcctaag  480
accccgccgcg ttaaaactga cagcaccgga acgcattcac tctatgctat gtatcaggat  540
tacgaaatta tgtttcatgt ttcgcaccat gcgcccttg agcagccgc gctggcagta    600
gtcaaaagca cgctggagtg ggcgccgaaa ttccaactgc aactgttcca ccacgccgca   660
gtaacgaaga agctattcc ggtctgccg accgttcgtt ataatatggg ttgcatccgc    720
actaattaca agggcaatac cctgaacag gagcaggaca gctggtgaa tcacttgtgg    780
aagcgtatgg ataaattgga agcagagaaa caccatcatt gtccgagtgc ttattatgag   840
gcagctctgc tgcagctgtg ggtcacagaa gcgtgcacct accgcccgtc agcacagcac   900
catcatgacc gttttccact gcgtaatgca gaaatggcta agtcctggaa atttccagc    960
gtgcctgctt cagaccgtat ggtgcaccat cacaccggag aaaaaccata tcgttgcaag  1020
```

-continued

```
gtttgcggga ccgccttcac gtggcattca cagctggccc gccactaa         1068

SEQ ID NO: 46           moltype = AA  length = 355
FEATURE                 Location/Qualifiers
source                  1..355
                        mol_type = protein
                        organism = Synthetic construct
SEQUENCE: 46
GDNFRETLKK KKRTLVMFYA PWCPHHHLLM REVPLRCTIS LWDTYQSEPD GFHHTRRLRE    60
QQKTAECDVG DYRCPQDQSA ALLVRAVQFT ETFLMERDKQ SKWSGIPAAY EVLEQEKGAL   120
SDGEIVSLSI EFYEGHHCPS PQAEKRLPKL HLEIIDKDSK TRRVKTDSTG THSLYAMYQD   180
YEIMPHVSHH CALGAAALAV VKSTLEWAPK FQLQLFHHAA VTKEPIPVLP TVRYNMGGIP   240
TNYKGNTLEQ EQEALVNHLW KRMDKLEAEK HHHCPSAYYE AALLQLWVTE ACTYRPSAQH   300
HHDRFPLRNA EMAKVLEISS VPASDRMVHH HTGEKPYRCK VCGTAFTWHS QLARH        355

SEQ ID NO: 47           moltype = AA  length = 20
FEATURE                 Location/Qualifiers
source                  1..20
                        mol_type = protein
                        organism = Cytomegalovirus
SEQUENCE: 47
GILARNLVPM VATVQGQNLK                                                20

SEQ ID NO: 48           moltype = AA  length = 20
FEATURE                 Location/Qualifiers
source                  1..20
                        mol_type = protein
                        organism = Human herpesvirus 4
SEQUENCE: 48
GPVFMCLGGL LTMVAGAVWL                                                20

SEQ ID NO: 49           moltype = AA  length = 20
FEATURE                 Location/Qualifiers
source                  1..20
                        mol_type = protein
                        organism = Cytomegalovirus
SEQUENCE: 49
VLCCYVLEET SVMLAKRPLI                                                20

SEQ ID NO: 50           moltype = AA  length = 20
FEATURE                 Location/Qualifiers
source                  1..20
                        mol_type = protein
                        organism = Macaca nemestrina
SEQUENCE: 50
VVTHTYLEPG PVTAQVVLQA                                                20

SEQ ID NO: 51           moltype = AA  length = 19
FEATURE                 Location/Qualifiers
source                  1..19
                        mol_type = protein
                        organism = Human herpesvirus 4
SEQUENCE: 51
AIQNAGLCTL VAMLEETIF                                                 19

SEQ ID NO: 52           moltype = AA  length = 20
FEATURE                 Location/Qualifiers
source                  1..20
                        mol_type = protein
                        organism = Macaca nemestrina
SEQUENCE: 52
SSAFTITDQV PFSVQLRALD                                                20

SEQ ID NO: 53           moltype = AA  length = 20
FEATURE                 Location/Qualifiers
source                  1..20
                        mol_type = protein
                        organism = West Nile virus
SEQUENCE: 53
AWDFGSVGGV FTSVGKAVHQ                                                20

SEQ ID NO: 54           moltype = AA  length = 20
FEATURE                 Location/Qualifiers
source                  1..20
                        mol_type = protein
                        organism = Influenza A virus
SEQUENCE: 54
SPLTKGILGF VFTLTVPSER                                                20
```

-continued

```
SEQ ID NO: 55          moltype = AA   length = 21
FEATURE                Location/Qualifiers
source                 1..21
                       mol_type = protein
                       organism = Mus musculus
SEQUENCE: 55
QLASTYTAYI VGYVHYGDWL K                                                21

SEQ ID NO: 56          moltype = AA   length = 21
FEATURE                Location/Qualifiers
source                 1..21
                       mol_type = protein
                       organism = Mus musculus
SEQUENCE: 56
NEKINRVVFV WNFLRVNTLS M                                                21

SEQ ID NO: 57          moltype = AA   length = 21
FEATURE                Location/Qualifiers
source                 1..21
                       mol_type = protein
                       organism = Mus musculus
SEQUENCE: 57
RPWEKPDKGA SYTPQALKKF P                                                21

SEQ ID NO: 58          moltype = AA   length = 21
FEATURE                Location/Qualifiers
source                 1..21
                       mol_type = protein
                       organism = Mus musculus
SEQUENCE: 58
ADLDFARQYY VMLYNTADEL L                                                21

SEQ ID NO: 59          moltype = AA   length = 21
FEATURE                Location/Qualifiers
source                 1..21
                       mol_type = protein
                       organism = Mus musculus
SEQUENCE: 59
FKGILPNLPS AYQNTVHANR M                                                21

SEQ ID NO: 60          moltype = AA   length = 21
FEATURE                Location/Qualifiers
source                 1..21
                       mol_type = protein
                       organism = Mus musculus
SEQUENCE: 60
TDSVIRLLSA LLRVSEVESR A                                                21

SEQ ID NO: 61          moltype = AA   length = 21
FEATURE                Location/Qualifiers
source                 1..21
                       mol_type = protein
                       organism = Mus musculus
SEQUENCE: 61
RVGKVFNAPA LPKASRKALG T                                                21

SEQ ID NO: 62          moltype = AA   length = 21
FEATURE                Location/Qualifiers
source                 1..21
                       mol_type = protein
                       organism = Mus musculus
SEQUENCE: 62
LGKELFMYFG HRALRIHFGM K                                                21

SEQ ID NO: 63          moltype = AA   length = 21
FEATURE                Location/Qualifiers
source                 1..21
                       mol_type = protein
                       organism = Mus musculus
SEQUENCE: 63
LFEDTNLCAI NAKRVTIMPK D                                                21

SEQ ID NO: 64          moltype = AA   length = 21
FEATURE                Location/Qualifiers
source                 1..21
                       mol_type = protein
                       organism = Mus musculus
SEQUENCE: 64
DVSVTKALQH LSHYFEGVLK C                                                21
```

```
SEQ ID NO: 65          moltype = AA   length = 21
FEATURE                Location/Qualifiers
source                 1..21
                       mol_type = protein
                       organism = Mus musculus
SEQUENCE: 65
LVSMPLWAKH MSDEQIQGFV E                                              21

SEQ ID NO: 66          moltype = AA   length = 21
FEATURE                Location/Qualifiers
source                 1..21
                       mol_type = protein
                       organism = Mus musculus
SEQUENCE: 66
EPFEKPVMIS MGNENVVEIK G                                              21

SEQ ID NO: 67          moltype = AA   length = 21
FEATURE                Location/Qualifiers
source                 1..21
                       mol_type = protein
                       organism = Mus musculus
SEQUENCE: 67
LEIQGTDPVS AVTLSLLDPE T                                              21

SEQ ID NO: 68          moltype = AA   length = 29
FEATURE                Location/Qualifiers
source                 1..29
                       mol_type = protein
                       organism = Mus musculus
SEQUENCE: 68
VGQDKPVFME EVPLPHTARI PGLRSLDEV                                      29

SEQ ID NO: 69          moltype = AA   length = 29
FEATURE                Location/Qualifiers
source                 1..29
                       mol_type = protein
                       organism = Mus musculus
SEQUENCE: 69
SKMDLEKPNY IVPDCMPVVY DKLPQPPTH                                      29

SEQ ID NO: 70          moltype = AA   length = 29
FEATURE                Location/Qualifiers
source                 1..29
                       mol_type = protein
                       organism = Mus musculus
SEQUENCE: 70
LSRAPRPTGP PASRLASKSH SSVKRLRKM                                      29

SEQ ID NO: 71          moltype = AA   length = 29
FEATURE                Location/Qualifiers
source                 1..29
                       mol_type = protein
                       organism = Mus musculus
SEQUENCE: 71
QPQQLPATDP KLLKLIRKAE KAEREFRKK                                      29

SEQ ID NO: 72          moltype = AA   length = 27
FEATURE                Location/Qualifiers
source                 1..27
                       mol_type = protein
                       organism = Mus musculus
SEQUENCE: 72
RVEKLQLESE LNESRTECIT ATSQMTA                                        27

SEQ ID NO: 73          moltype = AA   length = 29
FEATURE                Location/Qualifiers
source                 1..29
                       mol_type = protein
                       organism = Mus musculus
SEQUENCE: 73
INAEESEIRY STWKRAVMKS IGWVTTQSP                                      29

SEQ ID NO: 74          moltype = AA   length = 27
FEATURE                Location/Qualifiers
source                 1..27
                       mol_type = protein
                       organism = Mus musculus
SEQUENCE: 74
```

FAICFSCLLA HALNLIKLVR GRKPLSW                                                27

SEQ ID NO: 75           moltype = AA  length = 29
FEATURE                 Location/Qualifiers
source                  1..29
                        mol_type = protein
                        organism = Mus musculus
SEQUENCE: 75
MAMELFRVCL VVVTGIINHP LLFPRENAT                                              29

SEQ ID NO: 76           moltype = AA  length = 29
FEATURE                 Location/Qualifiers
source                  1..29
                        mol_type = protein
                        organism = Mus musculus
SEQUENCE: 76
EGCRGGRGQK RKRGCPQTHA VVLPLNNGD                                              29

SEQ ID NO: 77           moltype = AA  length = 29
FEATURE                 Location/Qualifiers
source                  1..29
                        mol_type = protein
                        organism = Mus musculus
SEQUENCE: 77
LETPRGKIQA KKWSLVPFSI PVFDILQDC                                              29

SEQ ID NO: 78           moltype = AA  length = 29
FEATURE                 Location/Qualifiers
source                  1..29
                        mol_type = protein
                        organism = Mus musculus
SEQUENCE: 78
FKEIQKIIKE PVPDSGLLGL FQGQSPLTS                                              29

SEQ ID NO: 79           moltype = AA  length = 27
FEATURE                 Location/Qualifiers
source                  1..27
                        mol_type = protein
                        organism = Mus musculus
SEQUENCE: 79
IPHNPRVAVK TTNNLVMKNS VCLERDS                                                27

SEQ ID NO: 80           moltype = AA  length = 29
FEATURE                 Location/Qualifiers
source                  1..29
                        mol_type = protein
                        organism = Mus musculus
SEQUENCE: 80
GRNQVVVAAG RSSWGAWLSG ALHVYSFSS                                              29

SEQ ID NO: 81           moltype = AA  length = 28
FEATURE                 Location/Qualifiers
source                  1..28
                        mol_type = protein
                        organism = Mus musculus
SEQUENCE: 81
DSVTKFKLQG SPVPRLRQSL LWGEPARP                                               28

SEQ ID NO: 82           moltype = AA  length = 29
FEATURE                 Location/Qualifiers
source                  1..29
                        mol_type = protein
                        organism = Mus musculus
SEQUENCE: 82
GFLKAYVKKF SYQSITTDDW KSFLYSHFK                                              29

SEQ ID NO: 83           moltype = AA  length = 27
FEATURE                 Location/Qualifiers
source                  1..27
                        mol_type = protein
                        organism = Mus musculus
SEQUENCE: 83
FTLTALRRRG FPPDAINNFC ARVGVTV                                                27

SEQ ID NO: 84           moltype = AA  length = 25
FEATURE                 Location/Qualifiers
source                  1..25
                        mol_type = protein
                        organism = Homo sapiens

```
SEQUENCE: 84
GDNFRETLKK KKRTLVMFYA PWCPH                                             25

SEQ ID NO: 85           moltype = AA   length = 25
FEATURE                 Location/Qualifiers
source                  1..25
                        mol_type = protein
                        organism = Homo sapiens
SEQUENCE: 85
LLMREVPLRC TISLWDTYQS EPDGF                                             25

SEQ ID NO: 86           moltype = AA   length = 25
FEATURE                 Location/Qualifiers
source                  1..25
                        mol_type = protein
                        organism = Homo sapiens
SEQUENCE: 86
TRRLREQQKT AECDVGDYRC PQDQS                                             25

SEQ ID NO: 87           moltype = AA   length = 25
FEATURE                 Location/Qualifiers
source                  1..25
                        mol_type = protein
                        organism = Homo sapiens
SEQUENCE: 87
LVRAVQFTET FLMERDKQSK WSGIP                                             25

SEQ ID NO: 88           moltype = AA   length = 25
FEATURE                 Location/Qualifiers
source                  1..25
                        mol_type = protein
                        organism = Homo sapiens
SEQUENCE: 88
EVLEQEKGAL SDGEIVSLSI EFYEG                                             25

SEQ ID NO: 89           moltype = AA   length = 25
FEATURE                 Location/Qualifiers
source                  1..25
                        mol_type = protein
                        organism = Homo sapiens
SEQUENCE: 89
PSPQAEKRLP KLHLEIIDKD SKTRR                                             25

SEQ ID NO: 90           moltype = AA   length = 25
FEATURE                 Location/Qualifiers
source                  1..25
                        mol_type = protein
                        organism = Homo sapiens
SEQUENCE: 90
VKTDSTGTHS LYAMYQDYEI MFHVS                                             25

SEQ ID NO: 91           moltype = AA   length = 25
FEATURE                 Location/Qualifiers
source                  1..25
                        mol_type = protein
                        organism = Homo sapiens
SEQUENCE: 91
ALGAAALAVV KSTLEWAPKF QLQLF                                             25

SEQ ID NO: 92           moltype = AA   length = 25
FEATURE                 Location/Qualifiers
source                  1..25
                        mol_type = protein
                        organism = Homo sapiens
SEQUENCE: 92
VTKEPIPVLP TVRYNMGGIP TNYKG                                             25

SEQ ID NO: 93           moltype = AA   length = 25
FEATURE                 Location/Qualifiers
source                  1..25
                        mol_type = protein
                        organism = Homo sapiens
SEQUENCE: 93
NTLEQEQEAL VNHLWKRMDK LEAEK                                             25

SEQ ID NO: 94           moltype = AA   length = 25
FEATURE                 Location/Qualifiers
source                  1..25
                        mol_type = protein
```

```
                        organism = Homo sapiens
SEQUENCE: 94
PSAYYEAALL QLWVTEACTY RPSAQ                                                 25

SEQ ID NO: 95           moltype = AA  length = 25
FEATURE                 Location/Qualifiers
source                  1..25
                        mol_type = protein
                        organism = Homo sapiens
SEQUENCE: 95
RFPLRNAEMA KVLEISSVPA SDRMV                                                 25

SEQ ID NO: 96           moltype = AA  length = 25
FEATURE                 Location/Qualifiers
source                  1..25
                        mol_type = protein
                        organism = Homo sapiens
SEQUENCE: 96
HTGEKPYRCK VCGTAFTWHS QLARH                                                 25
```